US005858713A

United States Patent [19]
Soderlund et al.

[11] Patent Number: 5,858,713
[45] Date of Patent: Jan. 12, 1999

[54] CALCIUM PERMEABLE INSECT SODIUM CHANNELS AND USE THEREOF

[75] Inventors: David M. Soderlund; Patricia J. Ingles, both of Geneva, N.Y.

[73] Assignee: Cornell Research Foundation, Inc., Ithaca, N.Y.

[21] Appl. No.: 808,793

[22] Filed: Feb. 28, 1997

Related U.S. Application Data

[60] Provisional application No. 60/034,361 Dec. 24, 1996 and provisional application No. 60/012,649 Mar. 1, 1996.

[51] Int. Cl.[6] .............................. C12P 21/02; C12N 5/10; C12N 15/85; C07H 21/04

[52] U.S. Cl. .......................... 435/69.1; 435/325; 435/348; 435/320.1; 536/23.5

[58] Field of Search .................................. 435/69.1, 172.1, 435/172.3, 320.1, 325, 348, 352, 366; 536/23.1, 23.5

[56] References Cited

U.S. PATENT DOCUMENTS

| | | | |
|---|---|---|---|
| 5,132,296 | 7/1992 | Cherksey | 514/57 |
| 5,204,239 | 4/1993 | Gitler et al. | 435/7.1 |
| 5,208,145 | 5/1993 | Rogers | 435/6 |
| 5,368,712 | 11/1994 | Tomich et al. | 204/403 |

OTHER PUBLICATIONS

Jacques et al., "Molecular Properties of the Action Potential Na+ Ionophore in Neuroblastoma Cells," *The Journal of Biological Chemistry*, 253:7383–7392 (1978).

Sawicki, "Unusual Response of DDT–Resistant Houseflies to Carbinol Analogues of DDT," *Nature*, 275:443–444 (1978).

Jackson et al., "Two Types of Mutants Affecting Voltage–Sensitive Sodium Channels in Drosophila Melanogaster," *Nature*, 308:189–191 (1984).

Taylor, "The Classification of Amino Acid Conservation," *J. Theor. Biol.* 119:205–218 (1986).

Johansen et al., "Regulated Expression at High Copy Number Allows Production of a Growth–Inhibitory Oncogene Product in Drosophila Schneider Cells," *Genes & Development*, 3:882–889 (1989).

Bordo et al., "Suggestions for Safe Residue Substitutions in Site–Directed Mutagenesis," *J. Mol. Biol.*, 217–721–729 (1991).

Patton et al., "A Voltage–Dependent Gating Transition Induces Use–Dependent Block by Tetrodotoxin of Rat IIA Sodium Channels Expressed in Xenopus Oocytes," *Neuron*, 7:637–647 (1991).

Taglialatela et al., "Novel Voltage Clamp to Record Small, Fast Currents from Ion Channels Expressed in Xenopus Oocytes," *Biophysical Journal*, 61:78–82 (1992).

Heinemann et al., "Clacium Channel Characteristics Conferred on the Sodium Channel by Single Mutations," *Nature*, 356:441–443 (1992).

Stühmer, "Electrophysiological Recording from Xenopus Oocytes," *Methods in Enzymology*, 207:319–339 (1992).

Amichot et al., "Transcription Analysis of the para Gene by In Situ Hybridization and Immunological Characterization of its Expression Product in Wild–type and Mutant Strains of Drosophila," *Insect Biochem. Molec. Biol.*, 23:381–390 (1993).

Mikala et al., "Differential Contribution by Conserved Glutamate Residues to an Ion–Selectivity Site in the L–type $Ca^{2+}$ Channel Pore," *Federation of European Biochemical Societies*, 335:265–269 (1993).

Ingles et al., "Characterization of Sodium Channel Genes From Insecticide–Susceptible and Insecticide–Resistant House Flies," *Society for Neuroscience Abstract*, 21:1824 (1995).

Ganetzky et al., "Analysis of Mutations Affecting Sodium Channels in Drosophila," *Annals New York Academy of Sciences*, pp. 325–337.

*Primary Examiner*—David Guzo
*Attorney, Agent, or Firm*—Nixon, Hargrave, Devans & Doyle LLP

[57] ABSTRACT

The present invention is directed to isolated nucleic acid molecules encoding a voltage-sensitive sodium channel (VSSC) of an insect having a mutation therein which renders the sodium channel permeable to calcium, as well as to the isolated calcium permeable voltage-sensitive sodium channels encoded thereby. Nucleic acid molecules encoding calcium permeable VSSCs of *Musca domestica, Drosophila melanogaster,* and *Heliothis virescens* are specifically provided. These calcium permeable channels can be used to monitor the function of the channel by monitoring calcium transport through the sodium channel, and for screening chemical agents for the ability of the chemical agent to modify sodium channel function, again by monitoring calcium transport through the channel.

39 Claims, 4 Drawing Sheets

५,८५८,७१३

CALCIUM PERMEABLE INSECT SODIUM CHANNELS AND USE THEREOF

This application claims priority of U.S. Provisional patent application Ser. No. 60/034,361, filed Dec. 24, 1996 and Ser. No. 60/012,649, filed Mar. 1, 1996.

FIELD OF THE INVENTION

The present invention relates generally to insect sodium channel proteins, and more particularly to calcium permeable, voltage-sensitive sodium channels of insects.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

Cell membranes must allow passage of various polar molecules, including ions, sugars, amino acids, and nucleotides. Special membrane proteins are responsible for transferring such molecules across cell membranes. These proteins, referred to as membrane transport proteins, occur in many forms and in all types of biological membranes. Each protein is specific in that it transports a particular class of molecules (such as ions, sugars, or amino acids) and often only certain molecular species of the class. All membrane transport proteins that have been studied in detail have been found to be multipass transmembrane proteins. By forming a continuous protein pathway across the membrane, these proteins enable the specific molecules to cross the membrane without coming into direct contact with the hydrophobic interior of the lipid bilayer of the plasma membrane.

There are two major classes of membrane transport proteins: carrier proteins and channel proteins. Carrier proteins bind the specific molecule to be transported and undergo a series of conformational changes in order to transfer the bound molecule across the membrane. Channel proteins, on the other hand, need not bind the molecule. Instead, they form hydrophilic pores that extend across the lipid bilayer; when these pores are open, they allow specific molecules (usually inorganic ions of appropriate size and charge) to pass through them and thereby cross the membrane. Transport through channel proteins occurs at a much faster rate than transport mediated by carrier proteins.

Channel proteins which are concerned specifically with inorganic ion transport are referred to as ion channels, and include ion channels for sodium, potassium, calcium, and chloride ions. Ion channels which open in response to a change in the voltage across the membrane are referred to as voltage-sensitive ion channels.

Voltage-sensitive sodium channels are the molecular target site of a wide variety of naturally-occurring neurotoxins (Catterall 1992). Moreover, the sodium channel is one of only a small number of insecticide target sites that has been exploited successfully to achieve effective insect control (Soderlund and Bloomquist 1989b). Three pharmacologically distinct classes of insecticides (pyrethroids/DDT analogs, N-alkylamides, and dihydropyrazoles) are known to act at three different target domains of the sodium channel (Soderlund and Knipple 1994). Moreover, at least 6 other discrete domains are implicated as sites of action for a variety of naturally-occurring neurotoxins that are known to affect sodium channel function (Soderlund and Knipple 1994); these domains may also serve as useful targets for novel insecticides. As a consequence of both the proven practical significance of the sodium channel as an insecticide target site and the rich pharmacology of its multiple neurotoxin-binding domains, the search for novel agents acting at this target continues to be an important objective of many commercial agrochemical discovery efforts.

Site-directed mutagenesis experiments with vertebrate sodium channel α subunits have identified structural domains involved in ion pore formation, channel inactivation, and the binding of some neurotoxins (reviewed in Catterall 1992). Within the pore-forming domains, two specific mutations have been identified that abolish the normal calcium-dependent blockade of sodium transport and render mutated vertebrate channels permeable to calcium (Heinemann et al. 1992) (FIG. 3).

The use of target-site based biochemical screening assays to identify novel sodium channel ligands as leads for insecticide design would greatly enhance efforts to exploit the sodium channel as a target in insecticide discovery research. However, this strategy is presently hampered by two significant technical limitations. First, the small amounts of nervous tissue that can be obtained by dissecting individual insects make the establishment of high-throughput biochemical screens based on subcellular preparations derived from insect nervous tissue prohibitively labor-intensive. Second, the principal biochemical tools that are currently available to measure ligand-sodium channel interactions are not appropriate for screening on insect sodium channels. Specifically, the radioligand [$^3$H]batrachotoxinin A 20-α-benzoate, which is commonly employed as a direct or allosteric probe of binding at 5 distinct sodium channel domains in mammalian brain preparations (Brown 1988), is not an effective pharmacological probe for insect sodium channels (Soderlund et al. 1989c). Also, radioisotopic ion flux assays with sodium-22 as the tracer, though useful for pharmacological characterization experiments (Bloomquist and Soderlund 1988; Ottea et al. 1989; Deecher and Soderlund 1991), are inappropriate for reasons of safety as routine high-throughput screening assays. The first limitation can be overcome by expressing insect sodium channel genes in cultured cells and employing these cells as a surrogate for native tissue in screening assays. However, overcoming the second limitation will require the development of novel methods for detecting ligand-dependent modifications of sodium channel function.

SUMMARY OF INVENTION

This need for novel assays of sodium channel function is addressed by the subject invention by providing insect sodium channels that are permeable to calcium. This strategy takes advantage of the existence of sensitive and relatively simple assays of changes in intracellular calcium concentrations using either calcium-chelating fluorescent dyes or calcium-binding bioluminescent proteins. Calcium-chelating fluorescent dyes (e.g., quin-2, fura-2, fluo-3) are well-established tools that have been employed in studies of voltage-sensitive calcium channels and the modulation of intracellular calcium by second messenger systems (Tsien 1988). This technique is limited to calcium and a small number of other ions for which suitable fluorescent intracellular probes are known; analogous reagents for the fluorescence-based detection of changes in intracellular sodium lack the dynamic range and signal-to-noise characteristics of calcium-chelating dyes and therefore are of limited use to monitor sodium channel activation. Alternatively, calcium influx may be assessed using the bioluminescent properties of the calcium-binding protein aequorin. Expression of the cloned aequorin gene (Prasher et al. 1985) in *E. coli* (Knight et al. 1991) or cultured human cells (Sheu et al. 1993) has been shown to provide a sensitive luminescent assay for changes in intracellular calcium concentration.

The subject invention thus provides an isolated nucleic acid molecule encoding a voltage-sensitive sodium channel (VSSC) of an insect having a mutation therein which renders the sodium channel encoded by the nucleic acid molecule permeable to calcium. In one embodiment, the VSSC is of the insec *Musca domestica*, and in another embodiment the VSSC is of the insect *Drosophila melanogaster*. In a further embodiment the VSSC is of the insect *Heliothis virescens*.

The isolated nucleic acid molecules of the invention can be inserted into suitable expression vectors and/or host cells. Expression of the nucleic acid molecules encoding the sodium channels results in production of calcium permeable functional sodium channels in a host cell.

The invention further provides a method of screening a chemical agent for the ability of the chemical agent to modify sodium channel function, which relies on the monitoring of calcium transport through the sodium channel which has been rendered permeable to calcium.

Further provided is an isolated nucleic acid molecule encoding a calcium permeable voltage-sensitive sodium channel of an insect, wherein the nucleic acid molecule encodes a first amino acid sequence having at least 95% amino acid identity to a second amino acid sequence. The second amino acid sequence is selected from the group consisting of SEQ ID NO:3 having a mutation at amino acid residue 1497; SEQ ID NO:3 having a mutation at amino acid residue 1790; SEQ ID NO:3 having a mutation at amino acid residue 1497 and a mutation at amino acid residue 1790; SEQ ID NO:4 having a mutation at amino acid residue 1497; SEQ ID NO:1 having a mutation at amino acid residue 1790; SEQ ID No:4 having a mutation at amino acid residue 1497 and a mutation at amino acid residue 1790; SEQ ID NO:23 having a mutation at amino acid residue 1478; SEQ ID NO:23 having a mutation at amino acid residue 1771; SEQ ID NO:23 having a mutation at amino acid residue 1478 and a mutation at amino acid residue 1771; SEQ ID NO:25 having a mutation at amino acid residue 60; SEQ ID NO:25 having a mutation at amino acid residue 353; and SEQ ID NO:25 having a mutation at amino acid residue 60 and a mutation at amino acid residue 353.

The invention also provides an isolated voltage-sensitive sodium channel of an insect having a mutation therein which renders the sodium channel permeable to calcium, and antibodies or antibody fragments specific for the calcium permeable sodium channel. The calcium permeable VSSC can be used to monitor the function of the sodium channel by monitoring calcium transport through the channel.

Further provided is an isolated calcium permeable voltage-sensitive sodium channel of an insect, wherein the calcium permeable voltage-sensitive sodium channel is comprised of a protein having a first amino acid sequence with at least 95% amino acid identity to a second amino acid sequence. The second amino acid sequence is selected from the group consisting of SEQ ID NO:3 having a mutation at amino acid residue 1497; SEQ ID NO:3 having a mutation at amino acid residue 1790; SEQ ID NO:3 having a mutation at amino acid residue 1497 and a mutation at amino acid residue 1790; SEQ ID NO:4 having a mutation at amino acid residue 1497; SEQ ID NO:4 having a mutation at amino acid residue 1790; SEQ ID NO:4 having a mutation at amino acid residue 1497 and a mutation at amino acid residue 1790; SEQ ID NO:23 having a mutation at amino acid residue 1478; SEQ ID NO:23 having a mutation at amino acid residue 1771; SEQ ID NO:23 having a mutation at amino acid residue 1478 and a mutation at amino acid residue 1771; SEQ ID NO:25 having a mutation at amino acid residue 60; SEQ ID NO:25 having a mutation at amino acid residue 353; and SEQ ID NO:25 having a mutation at amino acid residue 60 and a mutation at amino acid residue 353.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION

Figure 1:
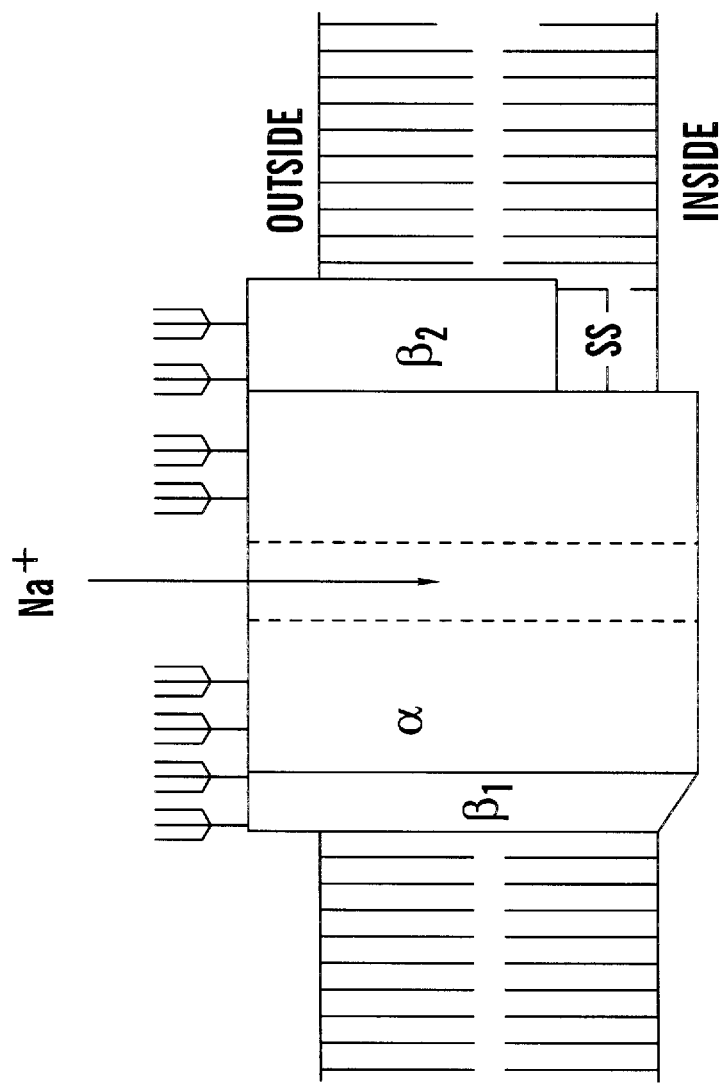
FIG. 1 is a model of a voltage sensitive sodium channel from mammalian brain in the plasma membrane. The alpha and $beta_1$ subunits interact noncovalently; the alpha and $beta_2$ subunits are linked by disulfide bonds. The branched structures at the outer surface of the channel represent oligosaccharides.

The plasmids designated pPJI1 and pPJI2 have each been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 97831 (pPJI1) and ATCC Accession No. 97832 (pPJI2). Both deposits were made on Dec. 20, 1996.

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized nucleic acid molecules). The term "isolated" when used in conjunction with a channel refers to a channel encoded by such an "isolated" nucleic acid molecule, generally expressed in a membrane, such as a plasma membrane within a cell or a synthetic lipid bilayer membrane. The expressed "isolated" channel has the pharmacological properties of a functional sodium channel.

As further used herein, the terms "corresponding to" or "having" or "as shown in" when used in conjunction with a SEQ ID NO for a nucleotide sequence refer to a nucleotide sequence which is substantially the same nucleotide sequence, or derivatives thereof (such as deletion and hybrid variants thereof, splice variants thereof, etc.). Nucleotide additions, deletions, and/or substitutions, such as those which do not affect the translation of the DNA molecule, are within the scope of a nucleotide sequence corresponding to or having or as shown in a particular nucleotide sequence (i.e. the amino acid sequence encoded thereby remains the same). Such additions, deletions, and/or substitutions can be, for example, point mutations made according to methods known to those skilled in the art. It is also possible to substitute a nucleotide which alters the amino acid sequence encoded thereby, where the amino acid substituted is a conservative substitution or where amino acid homology is conserved. It is also possible to have minor nucleotide additions, deletions, and/or substitutions which do not alter the function of the resulting VSSC. Similarly, the term "corresponding to" or "having" or "as shown in" when used in conjunction with a SEQ ID NO for an amino acid sequence refers to an amino acid sequence which is substantially the same amino acid sequence or derivatives thereof. Amino acid additions, deletions, and/or substitutions which do not negate the ability of the resulting protein to form a functional sodium channel are within the scope of an amino acid sequence corresponding to or having or as shown in a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. As used herein, two amino acid residues are conservative substitutions of one another where the two residues are of the same type. In this regard, for purposes of the present invention, proline, alanine, glycine, serine, and threonine, all of which are neutral, weakly hydrophobic residues, are of the same type. Glutamine, glutamic acid, asparagine, and aspartic acid, all of which are acidic, hydrophilic residues, are of the same type. Another type of residue is the basic, hydrophilic amino acid residues, which include histidine, lysine, and arginine. Leucine, isoleucine, valine, and methionine all of which are hydrophobic, aliphatic amino acid residues, form yet another type of residue. Yet another type of residue consists of phenylalanine, tyrosine, and tryptophan, all of which are hydrophobic, aromatic residues. Further descriptions of the concept of conservative substitutions are given by French and Robson 1983, Taylor 1986, and Bordo and Argos 1991.

As further used herein, the term "corresponding to" or "having" or "as shown in" or "consisting of" when used in conjunction with a SEQ ID NO for a nucleotide or amino acid sequence is intended to cover linear or cyclic versions of the recited sequence (cyclic referring to entirely cyclic versions or versions in which only a portion of the molecule is cyclic, including, for example, a single amino acid cyclic upon itself), and is intended to cover derivative or modified nucleotide or amino acids within the recited sequence. For example, those skilled in the art will readily understand that an adenine nucleotide could be replaced with a methyladenine, or a cytosine nucleotide could be replaced with a methylcytosine, if a methyl side chain is desirable. Nucleotide sequences having a given SEQ ID NO are intended to encompass nucleotide sequences containing these and like derivative or modified nucleotides, as well as cyclic variations. As a further example, those skilled in the art will readily understand that an asparagine residue could be replaced with an ethylasparagine if an ethyl side chain is desired, a lysine residue could be replaced with a hydroxylysine if an OH side chain is desired, or a valine residue could be replaced with a methylvaline if a methyl side chain is desired. Amino acid sequences having a given SEQ ID NO are intended to encompass amino acid sequences containing these and like derivative or modified amino acids, as well as cyclic variations. Cyclic, as used herein, also refers to cyclic versions of the derivative or modified nucleotides and amino acids.

The function of the encoded sodium channel can be assayed according to methods known in the art, such as by voltage clamp analysis of the channel following the functional expression of the channel in oocytes of the frog *Xenopus laevis* (see Taglialatela et al. 1992 and Stuhmer 1992 for a general discussion of voltage clamp analysis of receptors and ion channels expressed in Xenopus oocytes). Since the sodium channels of the subject invention are also permeable to calcium, the function of the encoded sodium channels can also be assayed for according to methods known in the art for monitoring calcium transport. This strategy takes advantage of the existence of sensitive and relatively simple assays of changes in intracellular calcium concentrations using either calcium-chelating fluorescent dyes or calcium-binding bioluminescent proteins. Calcium-chelating fluorescent dyes (e.g., quin-2, fura-2, fluo-3) are well-established tools that have been employed in studies of voltage-sensitive calcium channels and the modulation of intracellular calcium by second messenger systems (Tsien 1988). This technique is limited to calcium and a small number of other ions for which suitable fluorescent intracellular probes are known; analogous reagents for the fluorescence-based detection of changes in intracellular sodium lack the dynamic range and signal-to-noise characteristics of calcium-chelating dyes and therefore are of limited use to monitor sodium channel activation. Alternatively, calcium influx may be assessed using the bioluminescent properties of the calcium-binding protein aequorin. Expression of the cloned aequorin gene (Prasher et al. 1985) in *E. coli* (Knight et al. 1991) or cultured human cells (Sheu et al. 1993) has been shown to provide a sensitive luminescent assay for changes in intracellular calcium concentration.

As used herein, "functional expression" refers to the synthesis and any necessary post-translational processing of a sodium channel molecule in a host cell so that the channel is inserted properly in the cell membrane and is capable of conducting sodium ions in response to an experimentally-imposed change in the cell membrane potential or upon exposure to appropriate pharmacological agents.

As further used herein, "sensitivity" and "resistance" refer to the relative responses of genetically-defined insect populations to the paralytic or lethal actions of test insecticide. For example, a dose of DDT [1,1-bis-(4-chlorophenyl)-2,2, 2-trichloroethane] of approximately 0.02 $\mu$g per adult fly will kill approximately 50% of the treated individuals of a susceptible (Cooper-S) house fly strain, whereas doses of approximately 0.5 $\mu$g per adult fly are required to kill approximately 50% of the treated individuals of a resistant (538 ge) house fly strain (Sawicki 1978). The absolute doses that define susceptibility and resistance vary with the insect species and genetically defined populations examined, the test insecticide employed, and the method of exposure. In general, an insect strain or population is considered "resistant" if it exhibits tolerance to a test insecticide (assessed as the dose required to poison 50% of a treated population or group) that is at least 10 times greater than the tolerance of an appropriate reference, or "susceptible" population. Test insecticides include not only DDT but also analogs of DDT (e.g., methoxychlor, perthane) and pyrethroid insecticides (e.g., deltamethrin, fenvalerate, resmethrin, permethrin).

As also used herein, insects include *Musca domestics* (the house fly), the fruit or vinegar fly (*Drosophila melanogaster*), and various other insect species of agricultural, medical or veterinary importance, such as *Heliothis virescens* (the tobacco budworm), *Leptinotarsa decemlineata* (the Colorado potato beetle), *Blattella germanica* (the German cockroach), and Aedes aegypti (the yellow fever mosquito).

The subject invention provides an isolated nucleic acid molecule encoding a voltage-sensitive sodium channel (VSSC) of an insect having a mutation therein which renders the sodium channel encoded by the nucleic acid molecule permeable to calcium. The nucleic acid molecule can be deoxyribonucleic acid (DNA) or ribonucleic acid (RNA, including messenger RNA or mRNA), genomic or recombinant, biologically isolated or synthetic.

The DNA molecule can be a cDNA molecule, which is a DNA copy of a messenger RNA (mRNA) encoding the VSSC.

In one embodiment, the VSSC is of the insect *Musca domestica*. The nucleotide sequence of an insecticide susceptible VSSC of *Musca domestica* is shown in SEQ ID NO:1. The amino acid sequence encoded by this allele is shown in SEQ ID NO:3. This VSSC can be rendered permeable to calcium by mutating SEQ ID NO:1 at one or more of nucleotides 4489–4491, at one or more of nucleotides 5368–5370, or at one or more of nucleotides 4489–4491 and at one or more of nucleotides 5368–5370. Referring to the amino acid sequence (SEQ ID NO:3) the VSSC is rendered permeable to calcium by mutating SEQ ID NO:3 at amino acid residue 1497, or 1790, or 1497 and 1790. Preferably, the one or more mutations each comprises a substitution of glutamate for the amino acid residue.

Another VSSC of *Musca domestica* is encoded by the nucleotide sequence as shown in SEQ ID NO:2, which is an insecticide resistant VSSC. The amino acid sequence encoded by this allele is shown in SEQ ID NO:4. This VSSC can be rendered permeable to calcium by mutating SEQ ID NO:2 at one or more of nucleotides 4489–4491, at one or more of nucleotides 5368–5370, or at one or more of nucleotides 4489–4491 and at one or more of nucleotides 5368–5370. Referring to the amino acid sequence (SEQ ID NO:4), the VSSC is rendered permeable to calcium by mutating SEQ ID NO:4 at amino acid residue 1497, or 1790, or 1497 and 1790. Preferably, the one or more mutations each comprises a substitution of glutamate for the amino acid residue.

In another embodiment the VSSC is of the insect *Drosophila melanogaster*. The nucleotide sequence of a VSSC of *Drosophila melanogaster* is shown in SEQ ID NO:24. The amino acid sequence encoded by this molecule is shown in SEQ ID NO:23. This VSSC can be rendered permeable to calcium by mutating SEQ ID NO:24 at one or more of nucleotides 4432–4434, at one or more of nucleotides 5311–5313, or at one or more of nucleotides 4432–4434 and at one or more of nucleotides 5311–5313. Referring to the amino acid sequence (SEQ ID NO:23) the VSSC is rendered permeable to calcium by mutating SEQ ID NO:23 at amino acid residue 1478, or 1771, or 1478 and 1771. Preferably, the one or more mutations each comprises a substitution of glutamate for the amino acid residue.

In another embodiment the VSSC is of the insect *Heliothis virescens*. The partial nucleotide sequence of a VSSC of *Heliothis virescens* is shown in SEQ ID NO:26. The amino acid sequence encoded by SEQ ID NO:26 is shown in SEQ ID NO:25. This VSSC can be rendered permeable to calcium by mutating SEQ ID NO:26 at one or more of nucleotides 179–181, at one or more of nucleotides 1058–1060, or at one or more of nucleotides 179–181 and at one or more of nucleotides 1058–1060. Referring to the amino acid sequence (SEQ ID NO:25) the VSSC is rendered permeable to calcium by mutating SEQ ID NO:25 at amino acid residue 60, or 353, or 60 and 353. Preferably, the one or more mutations each comprises a substitution of glutamate for the amino acid residue.

These examples provide the sequences of two house fly sodium channel genes and one *Drosophila melanogaster* sodium channel gene, and a partial sequence of one *Heliothis virescens* sodium channel gene. The invention is not limited to these particular examples, however, as mutations according to the subject invention can be made in other insect sodium channels to render those channels permeable to calcium.

The nucleic acid molecules of the subject invention can be expressed in suitable host cells using conventional techniques. Any suitable host and/or vector system can be used to express the VSSCs. These include, but are not limited to, eukaryotic hosts such as mammalian cells (i.e., Hela cells, Cv-1 cells, COS cells), Xenopus oocytes, and insect cells (i.e. insect cell lines such as *Drosophila Schneider* [Johansen et al. 1989], Drosophila $K_c$ [Sang 1981], Sf9 [Smith et al. 1983], and High Five® (i.e., a cell line from the eggs of *Trichoplusia ni* having all the identifying characteristics of BTI-TN-5-B1-4, ATCC CRL 10859). [see U.S. Pat. No. 5,300,435]), as well as prokaryotic cells such as *Escherichia coil* and *Bacillus subtilis*.

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into suitable host cells. For example, sodium channel expression is often studied in Xenopus oocytes. DNA encoding the VSSC can be injected into the oocyte nucleus or transformed into the oocyte using a suitable vector, or mRNA encoding the VSSC can be injected directly into the oocyte, in order to obtain expression of a functional VSSC in the oocyte. It may be beneficial when expressing the sodium channels of the subject invention in Xenopus oocytes to coexpress a nucleic acid molecule encoding a tipE protein (Feng et al. 1995). Tip E has been found to be necessary to obtain expression of some sodium channels in Xenopus oocytes (Feng et al. 1995).

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wrild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicelLular cultures including procaryotic organisms and eucaryotic cells grown in tissue culture. The DNA sequences are cloned into the plasmid vector using standard cloning procedures known in the art, as described by Sambrook et al. (1989).

Host cells into which the nucleic acid encoding the VSSC has been introduced can be used to produce (i.e. to functionally express) the calcium permeable voltage-sensitive sodium channel.

Having identified the nucleic acid molecules encoding VSSCs and methods for expressing functional channels encoded thereby, the invention further provides a method of screening a chemical agent for the ability of the chemical agent to mcdify sodium channel function. The method comprises introducing a nucleic acid molecule encoding the VSSC into a host cell, and expressing the VSSC encoded by the molecule in the host cell. The expression results in the functional expression of a calcium permeable VSSC in the membrane of the host cell. The cell is then exposed to a chemical agent and evaluated to determine if the chemical agent modifies the function of the VSSC. From this evaluation, chemical agents effective in altering the function of the sodium channel can be found. Such agents may be, for example, tetrodotoxin, veratridine, and scorpion venom toxins. Additional agents can be found in Soderlund and Knipple 1994.

Cells transformed to include the calcium permeable VSSC according to the subject invention can be exposed to various potential insecticides and pesticides and evaluated for their susceptibility to the agents to develop and identify insect control agents that will not cause adverse effects to vertebrate species. Exemplary methods of screening are described in Eldefrawi et al. 1987 and Rauh et al. 1990.

The evaluation of the function of the sodium channel can be by any means known in the art for monitoring calcium transport through voltage-sensitive ion channels. Calcium transport can be monitored by voltage clamp or patch clamp analysis of ionic currents in Xenopus oocytes or transformed insect cells (see Taglialatela et al. 1992 and Stüuhmer 1992 for general discussions of these methods) under experimental conditions in which calcium or another divalent cation (e.g., barium) replaces sodium as the available permeant cation (Heinemann et al. 1992). Calcium transport can also be monitored by pre-incubating cells in a medium containing one or more chemical agents, adding a medium containing radioactive calcium ion ($^{45}Ca^{2+}$), incubating the cells further in this medium with or without depolarization by elevated external potassium concentration, and isolating cells by filtration. Calcium transport is detected by the measurement of $^{45}Ca^{2+}$ within the cells by liquid scintillation counting or other radiometric techniques (Daniell et al. 1983). These methods are directly comparable to those employed in the monitoring of sodium transport through sodium channels using $^{22}Na^{+}$ (Bloomquist and Soderlund, 1988), except that $^{45}Ca^{2+}$ is employed as the tracer. In another embodiment, the function of the calcium-permeable VSSC can be evaluated by pre-incubating cells to equlibrium with a calcium-selective fluorescent chelating agent such as fura-2 (Grynckiewicz et al. 1985), washing the cells, exposing the cells to a test agent, and monitoring the increase in intracellular calcium by measuring the fluorescence of the dye-calcium complex using either fluorescence spectrometry or microscopy (see Tsien 1988 for a general discussion of these methods and their application to intracellular calcium measurement and imaging). In another embodiment, cells transformed to express a calcium-permeable VSSC can be further transformed to co-express aequorin, a calcium-binding luminescent protein (Prasher et al. 1985). These cells can be pre-incubated to equilibrium with coelenterazine, the required cofactor for the formation of the aequorin-calcium complex, washed to remove extracellular coelenterazine, and then exposed to a test agent with or without depolarization by elevated external potassium concentration. Calcium transported is detected luminometrically as the result of the formation of the luminescent aequorin-calcium complex within the cell (Sheu et al. 1993).

Various modifications of the nucleic acid and amino acid sequences disclosed herein are covered by the subject invention. These varied sequences still encode a functional calcium permeable VSSC. The invention thus further provides an isolated nucleic acid molecule encoding a calcium permeable voltage-sensitive sodium channel of an insect, the nucleic acid molecule encoding a first amino acid sequence having at least 95% amino acid identity to a second amino acid sequence. The second amino acid sequence is selected from the group consisting of: SEQ ID NO:3 having a mutation at amino acid residue 1497; SEQ ID NO:3 having a mutation at amino acid residue 1790; SEQ ID NO:3 having a mutation at amino acid residue 1497 and a mutation at amino acid residue 1790; SEQ ID NO:4 having a mutation at amino acid residue 1497; SEQ ID NO:4 having a mutation at amino acid residue 1790; SEQ ID NO:4 having a mutation at amino acid residue 1497 and a mutation at amino acid residue 1790; SEQ ID NO:23 having a mutation at amino acid residue 1478; SEQ ID NO:23 having a mutation at amino acid residue 1771; SEQ ID NO:23 having a mutation at amino acid residue 1478 and a mutation at amino acid residue 1771; SEQ ID NO:25 having a mutation at amino acid residue 60; SEQ ID NO:25 having a mutation at amino acid residue 353; and SEQ ID NO:25 having a mutation at amino acid residue 60 and a mutation at amino acid residue 353.

The invention further provides isolated voltage-sensitive sodium channels of an insect having a mutation therein which renders the sodium channel permeable to calcium.

In one embodiment, the VSSC is of the insect *Musca domestica*. The nucleotide sequence of an insecticide susceptible VSSC of *Musca domestics* is shown in SEQ ID NO:1. The amino acid sequence encoded by this allele is shown in SEQ ID NO:3. This VSSC can be rendered permeable to calcium by mutating SEQ ID NO:1 at one or more of nucleotides 4489–4491, at one or more of nucleotides 5368–5370, or at one or more of nucleotides 4489–4491 and at one or more of nucleotides 5368–5370. Referring to the amino acid sequence (SEQ ID NO:3) the VSSC is rendered permeable to calcium by mutating SEQ ID NO:3 at amino acid residue 1497, or 1790, or 1497 and 1790. Preferably, the one or more mutations each comprises a substitution of glutamate for the amino acid residue.

Another VSSC of *Musca domestica* is encoded by the nucleotide sequence as shown in SEQ ID NO:2, which is an insecticide resistant VSSC. The amino acid sequence encoded by this allele is shown in SEQ ID NO:4. This VSSC can be rendered permeable to calcium by mutating SEQ ID NO:2 at one or more of nucleotides 4489–4491, at one or more of nucleotides 5368–5370, or at one or more of nucleotides 4489–4491 and at one or more of nucleotides 5368–5370. Referring to the amino acid sequence (SEQ ID NO:4), the VSSC is rendered permeable to calcium by mutating SEQ ID NO:4 at amino acid residue 1497, or 1790, or 1497 and 1790. Preferably, the one or more mutations each comprises a substitution of glutamate for the amino acid residue.

In another embodiment the VSSC is of the insect *Drosophila melanogaster*. The nucleotide sequence of a VSSC of *Drosophila melanogaster* is shown in SEQ ID NO:24. The amino acid sequence encoded by this molecule is shown in SEQ ID NO:23. This VS,SC can be rendered permeable to calcium by mutating SEQ ID NO:24 at one or more of nucleotides 4432–4434, at one or more of nucleotides 5311–5313, or at one or more of nucleotides 4432–4434 and at one or more of nucleotides 5311–5313. Referring to the amino acid sequence (SEQ ID NO:23) the VSSC is rendered permeable to calcium by mutating SEQ ID NO:23 at amino acid residue 1478, or 1771, or 1478 and 1771. Preferably, the one or more mutations each comprises a substitution of glutamate for the amino acid residue.

In another embodiment the VSSC is of the insect *Heliothis virescens*. The partial nucleotide sequence of a VSSC of *Heliothis virescens* is shown in SEQ ID NO:26. The amino acid sequence encoded by SEQ ID NO:26 is shown in SEQ ID NO:25. This VSSC can be rendered permeable to calcium by mutating SEQ ID NO:26 at one or more of nucleotides 179–181, at one or more of nucleotides 1058–1060, or at one or more of nucleotides 179–181 and at one or more of nucleotides 1058–1060. Referring to the amino acid sequence (SEQ ID NO:25) the VSSC is rendered permeable to calcium by mutating SEQ ID NO:25 at amino acid residue 60, or 353, or 60 and 353. Preferably, the one or more mutations each comprises a substitution of glutamate for the amino acid residue.

Figure 3:
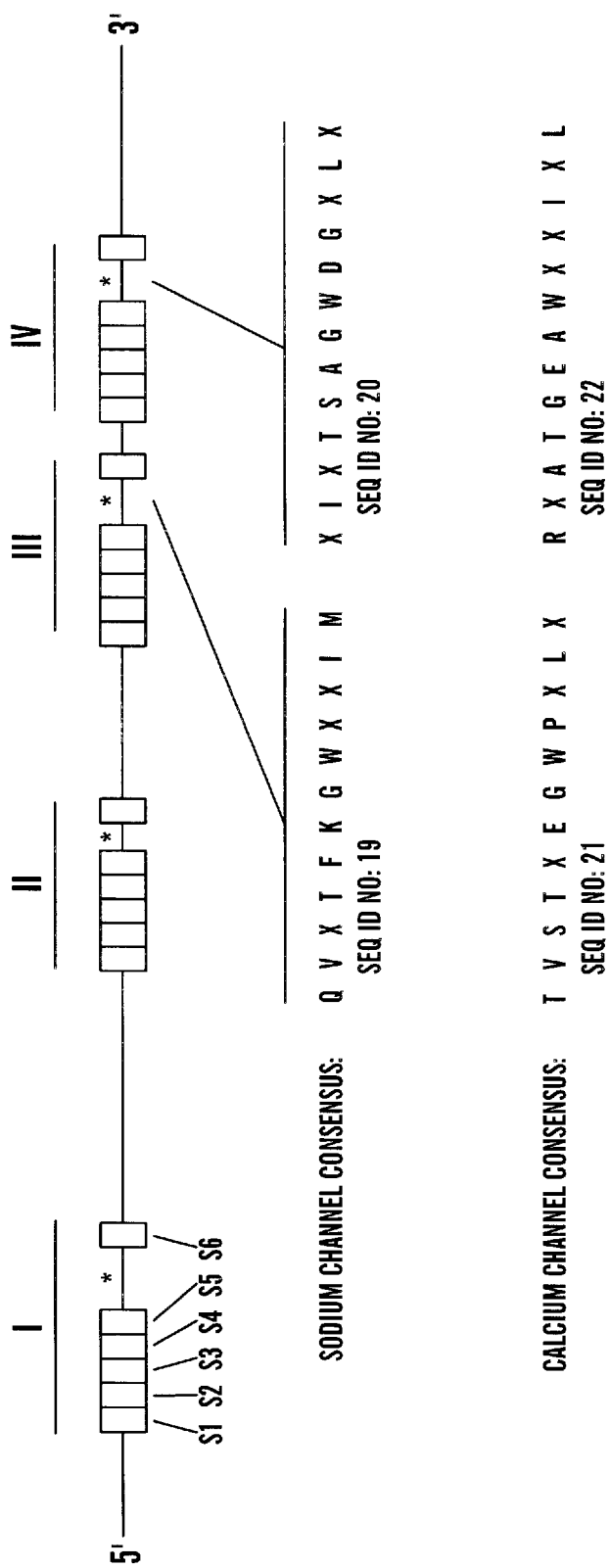
FIG. 3 shows the generalized structure of sodium channel and calcium channel α subunit genes, showing repeated homology domains I–IV, transmembrane regions S1–S6 (labeled in domain I only) and putative pore-forming regions (asterisks) (top). The bottom of FIG. 3 shows the consensus amino acid sequences in the pore-forming regions of domains III and IV of sodium and calcium channels; amino acids mutated to confer calcium permeability are shown in bold type (Heinemann et al. 1992); nonconserved amino acids are indicted as "x"
Figure 4:
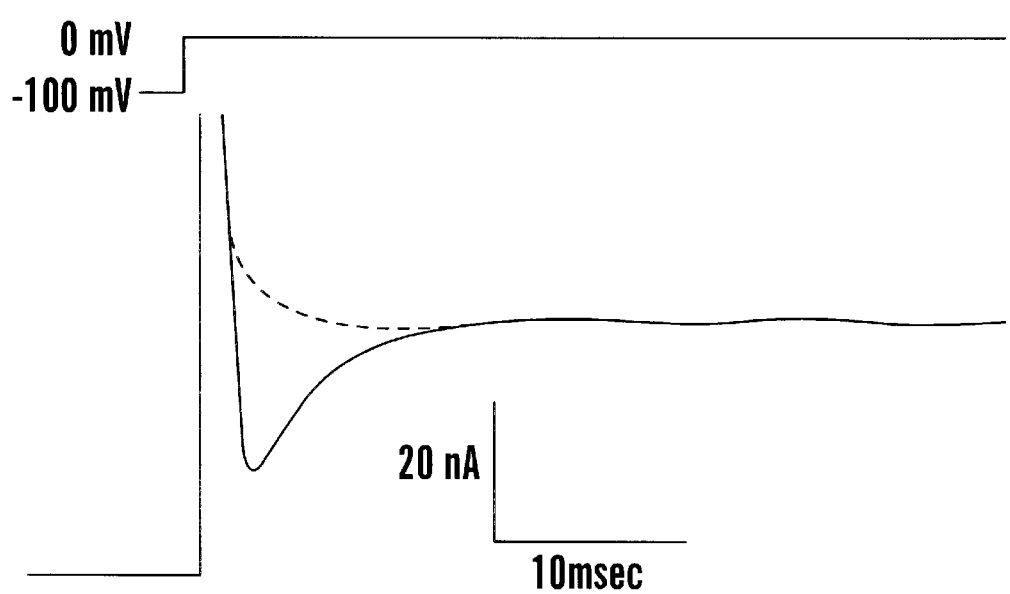
FIG. 4 shows the sodium current recorded following depolarization from −100 mV to 0 mV in a voltage-clamped Stage III Xenopus oocyte 72 hours after injection with hybrid-selected house fly sodium channel mRNA. The dashed line shows the typical shape of leakage currents obtained under these conditions from uninjected oocytes or oocytes in which sodium channels have been blocked by bath application of tetrodotoxin.

Insect sodium channels, other than those specifically exemplified herein, can also be mutated to be permeable to calcium, making the subject invention applicable to all such insect sodium channels. Sites for the introduction of mutations in other sodium channels can be identified on the basis of the optimal alignment of the amino acid sequences of those channels with insect sodium channel sequences such as those shown in SEQ ID NOs. 3, 4, 23, and 25. Such alignments will identify regions of other insect sodium channels that are structurally homologous to the four repeated sodium channel homology domains, each of which contains six putative hydrophobic transmembrane regions and one putative pore-forming region, as shown in FIG. 3. Further, alignments of amino acid sequence within the pore-forming regions of homology domains III and IV will identify conserved amino acid sequence motifs corresponding to the sodium channel consensus sequences for these regions shown in FIG. 3. Specifically, these alignments will reveal a conserved lysine (K) residue within the pore-forming region of homology domain III and a conserved alanine (A) residue within the pore-forming region of homology domain IV. These residues are critical for conferring the natural sodium ion selectivity of sodium channels. Introduction of mutations that convert these residues to glutamate residues, either singly or in combination, will produce other calcium permeable insect sodium channels in addition to those specifically exemplified herein.

The subject application provides the sequences of the insecticide sensitive and insecticide resistant sodium channels of the house fly, and exemplary sites for mutations therein that render the channel permeable to calcium. A plasmid designated pPJI1 has been deposited with the ATCC under Accession No. 97831, and has a KpnI/AatII restriction fragment of about 3620 bp. A plasmid designated pPJI2 has also been deposited with the ATCC, under Accession No. 97832, and has an AatII/SphII restriction fragment of about 2700 bp. When the above two restriction fragments are ligated together at their AatII sites, the resulting nucleic acid molecule encodes a voltage-sensitive sodium channel which confers susceptibility to an insecticide in *Musca domestica*. This resulting nucleic acid molecule can also be mutated as disclosed herein to render the channel permeable to calcium. The sequence of the para gene of *Drosophila melanogaster*, as disclosed herein, is of the $a^+b^-c^-d^+e^-f^-h^-i^+$ splice variant (Loughney et al. 1989, Thackeray and Ganetzky 1994, Thackeray and Ganetzky 1995, O'Dowd et al. 1995). Other para gene sequences could also be mutated as taught herein to render the channels permeable to calcium, such as other exon splice variants of the *Drosophila melanogaster* sequence disclosed by Loughney et al. 1989, Thackeray and Ganetzky 1994, Thackeray and Ganetzky 1995, and O'Dowd et al. 1995. The partial sequence of the *Heliothis virescens* sodium channel, as disclosed herein, is published in European Patent Application Publication No. 0 615 976 A1, published Sep. 21, 1994 on behalf of American Cyanamid Company. These three insects are examples only and the invention is not intended to be limited to these insects. Other insect sodium channels can be mutated as taught herein.

A variety of methodologies known in the art can be utilized to obtain an isolated calcium permeable VSSC according to the subject invention. A member of the calcium permeable VSSC family can be purified from cells which have been altered to express the channel protein. As used herein, a cell is said to be "altered to express the channel protein" when the cell, through genetic manipulation, is made to produce the channel protein which it normally does not produce (i.e., the cell does not normally produce a calcium permeable sodium channel). One skilled in the art can readily adapt procedures for introducing and expressing either genomic, cDNA or synthetic sequences into either eukaryotic or prokaryotic cells in order to generate a cell which produces a member of the calcium permeable VSSC family utilizing the sequences disclosed herein. One skilled in the art can then readily follow known methods for isolating the channel proteins in order to obtain a member of the calcium permeable VSSC protein family, free of natural contaminants. These include, but are not limited to, immunochromatography, HPLC, size-exclusion chromatography, ion-exchange chromatography, and immunoaffinity chromatography.

A VSSC as defined herein includes molecules encoding VSSCs comprised of a protein having a first amino acid sequence with at least 95% amino acid identity to a second amino acid sequence, the second amino acid sequence selected from the group consisting of: SEQ ID NO:3 having a mutation at amino acid residue 1497; SEQ ID NO:3 having a mutation at amino acid residue 1790; SEQ ID NO:3 having a mutation at amino acid residue 1497 and a mutation at amino acid residue 1790; SEQ ID NO:4 having a mutation at amino acid residue 1497; SEQ ID NO:4 having a mutation at amino acid residue 1790; SEQ ID NO:4 having a mutation at amino acid residue 1497 and a mutation at amino acid residue 1790; SEQ ID NO:23 having a mutation at amino acid residue 1478; SEQ ID NO:23 having a mutation at amino acid residue 1771; SEQ ID NO:23 having a mutation at amino acid residue 1478 and a mutation at amino acid residue 1771; SEQ ID NO:25 having a mutation at amino acid residue 60; SEQ ID NO:25 having a mutation at amino acid residue 353; and SEQ ID NO:25 having a mutation at amino acid residue 60 and a mutation at amino acid residue 353.

Antibodies can be raised to the calcium permeable voltage-sensitive sodium channel. Antibodies of the subject invention include polyclonal antibodies and monoclonal antibodies capable of binding to the channel protein, as well as fragments of these antibodies, and humanized forms. Humanized forms of the antibodies of the subject invention may be generated using one of the procedures known in the art such as chimerization. Fragments of the antibodies of the present invention include, but are not limited to, the Fab, the Fab2, and the Fd fragments.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell 1984 and St. Groth et al. 1980). Any animal (mouse, rabbit, etc.) which is known to produce antibodies can be immunized with the antigenic channel protein (or an antigenic fragment thereof). Methods for immunization are well known in the art. Such methods include subcutaneous or intraperitoneal injection of the protein. One skilled in the art will recognize that the amount of the channel protein used for immunization will vary based on the animal which is immunized, the antigenicity of the protein, and the site of injection.

The protein which is used as an immunogen may be modified or administered in an adjuvant in order to increase the protein's antigenicity. Methods of increasing the antigenicity of a protein are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al. 1988).

Hybridomas secreting the desired antibodies are cloned and the class and subclass are determined using procedures known in the art (Campbell 1984).

For polyclonal antibodies, antibody containing antisera is isolated from the immunized animal and is screened for the presence of antibodies with the desired specificity using one of the above-described procedures.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, etc. Procedures for accomplishing such labeling are well known in the art, for example see Sternberger et al. 1970, Bayer et al. 1979, Engval et al. 1972, and Goding 1976.

The labeled antibodies or fragments thereof of the present invention can be used for in vitro, in vivo, and in situ assays to identify cells or tissues which express a calcium permeable VSSC, to identify samples containing the calcium permeable VSSC proteins, or to detect the presence of a calcium permeable VSSC in a sample. More particularly, the antibodies or fragments thereof can thus be used to detect the presence of a calcium permeable VSSC in a sample, by contacting the sample with the antibody or fragment thereof. The antibody or fragment thereof binds to any calcium permeable VSSC present ir the sample, forming a complex therewith. The complex can then be detected, thereby detecting the presence of the calcium permeable VSSC in the sample.

The invention also provides a method of monitoring the functioning of a sodium channel. The method comprises mutating a sodium channel so as to render the channel permeable to calcium, and then expressing the mutated sodium channel in a membrane. The function of the sodium channel is then monitored by monitoring calcium transport through the membrane by way of the sodium channel. Such a mutated sodium channel can be made using various methods known in the art, such as site-directed mutagenesis of a nucleic acid molecule encoding a sodium channel. The membrane in which the mutated sodium channel is expressed can be a synthetic membrane or can be the plasma membrane of a host cell into which the nucleic acid molecule encoding the calcium permeable channel is introduced. As with the above-described expression of calcium permeable sodium channels in various host cells, it may be desirable to coexpress a tip E protein with the sodium channel to obtain functional expression of the channel.

MATERIALS AND METHODS

Heads of newly-emerged adult house flies (NAIDM or 538ge strain) (Knipple et al. 1994) were ground to a fine powder under liquid $N_2$ and extracted with acid guanidinium isothiocyanate/phenol/chloroform to obtain total RNA (Chomczynski and Sacchi 1987), which was fractionated on oligo(dT)-paramagnetic beads (PolyATtract mRNA isolation system; Promega, Madison, Wis.) to obtain poly($A^+$) RNA. Pools of first strand cDNA were synthesized using either random hexamers (Harvey and Darlison 1991) or oligo(dT) adapted for the 3'-RACE procedure (Frohman and Martin 1989). These cDNA pools were employed as templates in the polymerase chain reaction (PCR) (Saiki et al. 1988) to amplify overlapping cDNA segments spanning the entire Vsscl coding sequence. Mixed-sequence oligonucleotide primers employed for these amplifications comprised all possible sequence combinations encoding short (i.e., 6–8 residues) regions of amino acid conservation between the para gene of *D. melanogaster* and rat brain sodium channel I (Loughney et al. 1989; Knipple et al. 1991). In a few cases, mixed-sequence primers were based solely on the *D. melanogaster* sequence. Defined-sequence primers were derived either from the previously described 309-nucleotide exon of the house fly Vsscl gene (Knipple et al. 1994) or from internal sequences of house fly cDNA fragments obtained by amplification with mixed-sequence primers. All primers were synthesized using an Applied Biosystems 392 instrument, deprotected using procedures provided by Applied Biosystems, desalted, and used without further purification. The sequences and designations of these primers are given in Table I (primers A1 to G2). The methods and reagents employed in PCR amplifications are described elsewhere (Knipple et al. 1991; Henderson et al. 1994; Knipple et al. 1994); specific amplification conditions for each cDNA fragment were optimized by varying the annealing temperatures and extension times of the reaction. Following amplification, PCR products were separated from excess primers either by filtration of the reaction mixture through a Centricon-100 concentrator (Amicon, Beverly, Mass.) or by preparative electrophoresis on agarose gels, excision of the desired product, and extraction from the gel matrix (QIAquick spin column; Qiagen, Chatsworth, Calif.) prior to use as templates for DNA sequencing.

The DNA sequences of amplified cDNA fragments were determined by automated sequencing with an Applied Biosystems 373 instrument using fluorescently-labeled dideoxynucleotides and Taq DNA polymerase (PCR/Sequencing Kit; Applied Biosystems, Foster City, Calif.) in a modification of the dideoxynucleotide chain-termination method (Sanger et al. 1977). Sequencing of each amplification product was initiated by using the amplification primers to sequence inward from the termini, and additional primers were synthesized as needed to obtain the complete sequence of each strand. Mixed-sequence amplification primers were employed for sequencing at concentrations 10-fold higher than that used for defined-sequence primers. All sequence ambiguities and apparent polymorphisms were resolved by performing additional multiple sequencing reactions. The full-length Vsscl coding sequences from the NAIDM and 538ge strains were compiled from 239 and 209 individual sequencing reactions, respectively, and were edited using the SeqEd software program (Applied Biosystems). Complete house fly Vsscl sequences were analyzed and compared with published sodium channel sequences using the DNASTAR software package (DNASTAR, Madison, Wis.).

EXAMPLE I

SEQUENCING OF THE INSECTICIDE SENSITIVE VSSC OF HOUSE FLY

Figure 2:
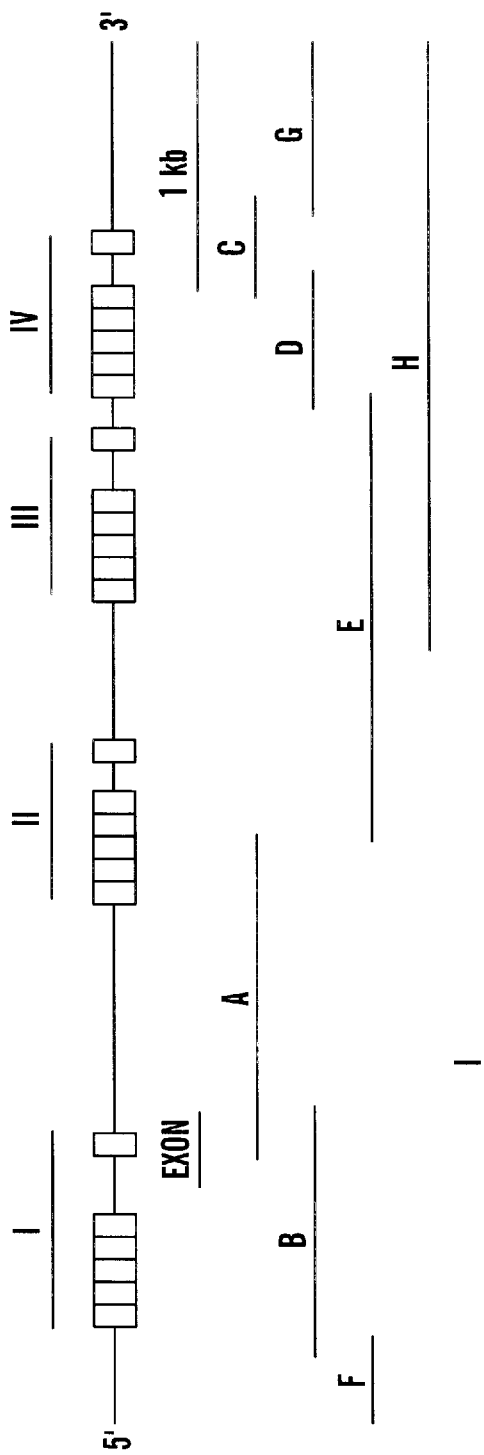
FIG. 2 is a diagram of the structural organization of the voltage-sensitive sodium channel coding sequence of *Musca domestics* (Vsscl) showing repeated homology domains I–IV and putative transmembrane helices (rectangles). Shown below the structural organization are the relative length and location of the previously-described 309-nucleotide exon of Vsscl (Knipple et al. 1994) (exon); seven overlapping PCR-amplified cDNA fragments (A–G) employed as templates for DNA sequencing; and two larger cDNA fragments (H,I) employed for site-directed mutagenesis and the construction of full-length cDNAs.

As an expedient alternative to conventional iterative screenings of cDNA libraries, a sequencing strategy for the house fly Vsscl gene was based on the PCR amplification and direct automated sequencing of overlapping cDNA fragments (FIG. 2). The point of entry for this strategy was the 309-nucleotide exon of the house fly Vsscl gene identified previously from sequencing of cloned genomic DNA (Knipple et al. 1994). The use of defined-sequence primers from this region (Table I, A1 or B2) in combination with mixed-sequence primers encoding conserved amino acid sequences in either region IIS3 (A2) or the extracellular N-terminal domain (B1) gave cDNA fragments A and B. A second point of entry was established in homology domain IV using a pair of mixed-sequence primers (C1 and C2) to obtain fragment C. A primer (D2) designed from the internal sequence of fragment C, together with a mixed-sequence primer (D1) encoding a conserved amino acid motif in the short linker between homology domains III and. IV, gave fragment D. A pair of defined-sequence primers (E1, E2) based on internal sequences of fragments A. and D gave the large fragment E, which spanned most of homology domain II and all of homology domain III. Fragment F, corresponding to the 5' end of the coding sequence, was obtained using a defined-sequence primer (F2) derived from the internal sequence of fragment B and a mixed-sequence primer (F1) derived from a segment of the *D. melanogaster* sequence upstream from the translation start site Loughney et al. 1989). Similarly, fragment G, containing the 3' end of the coding sequence, was obtained using a defined-sequence primer (G1) derived from the internal sequence of fragment C and a mixed-sequence primer (G2) derived from a segment of the *D. melanogaster* sequence downstream from the stop codon (Thackeray and Ganetzky 1994).

The complete coding sequence of the Vsscl$^{NAIDM}$ allele of the house fly, comprising a single open reading frame of 6318 nucleotides (SEQ ID NO:1), was determined by automated DNA sequencing using cDNA fragments A–G as templates. This cDNA coded for a 2105-amino acid polypeptide (SEQ ID NO:3) with a predicted molecular weight of 236,671 Daltons that exhibited all of the common structural landmarks found in sodium channel α subunit genes (Catterall 1992; Kallen et al. 1993), including four large internally homologous subdomains (I–IV), each containing six hydrophobic putative transmembrane helices (S1-S6) and a conserved sequence element between domains S5 and S6 identified as an ion pore-forming domain. The deduced Vsscl$^{NAIDM}$ amino acid sequence also contained a conserved element in the S4 region of each homology domain, characterized by a repeated motif of positively-charged amino acids that are thought to form the voltage-sensing element of the channel, and a short segment of conserved sequence between homology domains III and IV that has been identified as the channel inactivation gate. The deduced Vsscl$^{NAIDM}$ protein contained 10 potential sites for N-linked glycosylation (Kornfeld and Kornfeld 1985), 6 of which occur in putative extracellular regions. These regions of other sodium channel α subunit sequences are also known to contain potential glycosylation sites (Catterall 1992; Kallen et al. 1993).

Vertebrate sodium channels are known to undergo functional regulation as the result of phosphorylation by cAMP-dependent protein kinases at sites in the intracellular linker between homology domains I and II and by protein kinase C at a site in the intracellular linker between homology domains III and IV (Catterall 1992; Kallen et al. 1993). The deduced Vsscl$^{NAIDM}$ protein contained three potential cAMP-dependent protein kinase phosphorylation sites (Kemp and Pearson 1990) (Ser540, Ser557, and Ser628 of SEQ ID NO:3) in the cytoplasmic linker between homology domains I and II. The location of two of these (Ser540 and Ser557 of SEQ ID NO:3) corresponded to the cluster of four sites found in this region of vertebrate brain sodium channels that are implicated in sodium channel regulation (Catterall 1992). The deduced Vsscl$^{NAIDM}$ protein also contained three additional potential phosphorylation sites (Ser1167, Ser1207, and Ser2097 of SEQ ID NO:3) in other putative intracellular domains. The role of these phosphorylation sites in the regulation of insect sodium channels by cAMP-dependent protein kinase is not known. The deduced house fly voltage-sensitive sodium channel protein also contained two potential sites for protein kinase C phosphorylation (Ser1191 and Ser1582 of SEQ ID NO:3) (Kemp and Pearson 1990), the latter of which is the conserved site located within the inactivation gate sequence of the cytoplasmic linker between domains III and IV. Although the conservation of this site implicates a role for protein kinase C in the regulation of insect sodium channels, such an effect has not been demonstrated experimentally.

The deduced Vsscl$^{NAIDM}$ protein was 90.0% identical to the most similar variant of the para gene product of *D. melanogaster* (SEQ ID NO:23) (Loughney et al. 1989; Thackeray and Ganetzky 1994). The level of sequence identity was highest (≤95%) in the N-terminal intracellular domain, the linker between homology domains III and IV, and homology domain IV. The level of sequence identity was lowest (73%) in the intracellular C-terminal domain. Alignment of the Vsscl sequence with 12 other sodium channel α subunit sequences found in the GenBank database showed that the Vsscl and para gene products exhibited approximately the same degree of sequence similarity as homologous sodium channel α subunit isoforms from different vertebrate species. These findings confirm and extend previous observations (Williamson et al. 1993; Knipple et al. 1994), based on fragmentary genomic DNA and cDNA sequences, of the high degree of sequence similarity between this house fly gene and the para gene of *D. melanogaster* and reinforce the conclusion that Vsscl is the homolog of para in the house fly.

In *D. melanogaster* (Thackeray and Ganetzky 1994; O'Dowd et al. 1995) and *Drosophila virilis* (Thackeray and Ganetzky 1995), multiple sodium channel α subunit variants, each under specific developmental regulation, are generated from the para gene by the alternative usage of 8 exons (designated a–f, h, and i) located in homology domain II and portions of the cytoplasmic linker regions on either side of this domain. Given the heterogeneity of sodium channel-encoding sequences found in these Dipteran species, it was surprising to detect only a single sequence variant among the pool of amplified house fly head cDNA fragments. The Vsscl$^{NAIDM}$ sequence contained segments identical to exon a and homologous (21 identical amino acids out of 24) to exon i of *D. melanogaster*. Recent studies suggest that both of these exons are required for the expression of high sodium current densities in embryonic *D. melanogaster* neurons (O'Dowd et al. 1995). In the region encoded by either exon c or exon d, the house fly sequence differs from both *D. melanogaster* sequences but is slightly more similar to exon d (50 identical amino acids out of 55) than to exon c (49 identical amino acids out of 55). The house fly sequence lacked segments homologous to *D. melanogaster* exons b, e, and f but contained a segment identical to exon h, which is a variable element found in some *D. virilis* sequences but not detected in *D. melanogaster*. The house fly Vsscl$^{NAIDM}$ sequence described is thus characterized as structurally homologous to the $a^+b^-c^-d^+e^-f^-h^+i^+$ splice variant of *D. melanogaster* and *D. virilis*. The identification of this molecular form as the predominant sodium channel sequence variant in house fly heads was unexpected because it has not been detected among the arrays of splice variants detected in whole embryos or whole adults of either *D. melanogaster* or *D. virilis*.

EXAMPLE II

SEQUENCING OF THE INSECTICIDE RESISTANT VSSC OF HOUSE FLY

The PCR amplification/sequencing strategy summarized in FIG. 2 was also employed to determine the sequence of Vsscl cDNAs from heads of the 538ge house fly strain that carries the kdr trait. The nucleotide sequence of the VSSC of the 538 ge house fly is shown in SEQ ID NO:2, and the amino acid sequence is shown in SEQ ID NO:4. The amino acid sequence of 2104 residues (SEQ ID NO:4) encoded by the Vsscl$^{538\ ge}$ cDNA contains 12 amino acid differences compared to hat of the Vsscl$^{NAIDM}$ sequence (SEQ ID NO:3) as follows: a substitution of phenylalanine for leucine at amino acid residue 1014 of SEQ ID NO:3; a substitution of isoleucine for methionine at amino acid residue 1140 of SEQ ID NO:3; a substitution of aspartic acid for glycine at amino acid residue 2023 of SEQ ID NO:3; a deletion of amino acid residues 2031–2034 of SEQ ID NO:3 (glycine-alanine-threonine-alanine); a substitution of threonine for serine at amino acid residue 2042 of SEQ ID NO:3; a substitution of alanine for valine at amino acid residue 2054 of SEQ ID NO:3; and an insertion of three amino acid residues (asparagine-glycine-glycine) after amino acid residue 2055 of SEQ ID NO:3 (between amino acid residues 2055 and 2056 of SEQ ID NO:3).

EXAMPLE III

SITE-DIRECTED MUTAGENESIS OF THE HOUSE FLY SODIUM CHANNEL

Two partial house fly sodium channel cDNAs that comprise the entire Vsscl$^{NAIDM}$ coding sequence (FIG. 2, Fragments H and I) were obtained by PCR amplification using defined-sequence primers (H1 and H2 or I1 and I2; see Table 1). Fragment H was cloned in the pALTER-1 vector (Altered Sites mutagenesis system, Promega) and used as a template for site-directed mutagenesis. Three mutated sodium channel partial cDNAs were constructed that contained the permeability-altering mutations in homology domains III and IV (see FIG. 3), either singly or in combination. Creation of these mutated sequences involves the preparation of single-stranded plasmid DNA, the annealing of mutagenic oligonucleotides to create the target mutation in Fragment H and to restore the function of one of two antibiotic resistance genes also contained in the plasmid, and re-synthesis of the complete second strand of plasmid DNA using T4 DNA polymerase. The mutagenic oligonucleotide M1, shown in SEQ ID NO:31, corresponds to nucleotides 4477–4503 of SEQ ID NO:1 with the substitution of G for A at nucleotide residue 4489 and introduces a mutation from lysine to glutamate at amino acid residue 1497 of SEC) ID NO:3. The mutagenic oligonucleotide M2, shown in SEQ ID NO:32, corresponds to nucleotides 5356–5383 of SEQ ID NO:1 with the substitution of A for C at nucleotide residue 5369 and the substitution of G for C at nucleotide residue 5370 and introduces a mutation from alanine to glutamate at amino acid residue 1790 of SEQ ID NO:3. Mutated plasmids obtained by these procedures are then propagated in *E. coli* and mutated sequences are efficiently recovered as antibiotic-resistant colonies. Mutated partial cDNA sequences obtained by this method are excised as restriction fragments and cloned into plasmids containing Fragment I, thereby yielding full-length mutated house fly $Vsscl^{NAIDM}$ cDNAs. The identity and fidelity of all mutated constructs are confirmed by DNA sequencing.

EXAMPLE IV

EXPRESSION OF CALCIUM PERMEABLE SODIUM CHANNELS IN XENOPUS OOCYTES

Native and mutated calcium permeable sodium channels were expressed in Xenopus oocytes to determine the efficacy of these mutations in altering the ion selectivity of house fly sodium channels. The retention of pharmacological specificity is essential if mutated channels are to be useful tools in the search for novel sodium channel ligands. Expression experiments are based on studies of the expression of hybrid-selected house fly sodium channel mRNA in oocytes (see FIG. 4). The procedures employed to achieve expression from mRNA synthesized in vitro from cloned cDNA are based on contemporary, well-established protocols (Goldin 1992; Stuhmer 1992). To explore the effects of specific mutations on ion selectivity, voltage-gated currents are measured in normal (sodium-containing) medium and in media with modified cation content in which a divalent cation (calcium or barium) replaces sodium as the permeant cation (Heinemann et al. 1992). These experiments establish appropriate conditions for comparative pharmacological studies employing a variety of agents that act at various ligand-binding domains of the sodium channel, including: channel blockers (tetrodotoxin); alkaloid activators (veratridine, batrachotoxin); pumiliotoxin; brevetoxins; insect-specific polypeptide scorpion toxins (AaIT, LqhαIT); and insecticides (pyrethroids, N-alkylamides, and dihydropyrazoles).

EXAMPLE V

EXPRESSION OF CALCIUM PERMEABLE SODIUM CHANNELS IN CULTURED INSECT CELLS

Expression of mutated sodium channels in cultured insect cells permits the use of such cells to assess the utility of fluorescent and luminescent probes of calcium transport and the use of these methods to screen for novel insecticidal agents. To construct transformation vectors, fragment I, the 5' end of the house fly sodium channel cDNA (see FIG. 2), was subcloned into an appropriate transformation vector (e.g., pRmHa3, described in Millar et aL. 1994) that places the house fly cDNA sequence under control of the inducible Drosophila metallothionein promoter. Fragment H (one of the three mutated sequences, obtained as restriction fragments from the site-directed mutagenesis constructs in pALTER-1) was then subcloned into the fragment I construct to achieve full-length transformation vectors. To achieve expression of mutated channels, Schneider cells are cotransformed with a mutated Vsscl construct in pRmHa3 and a second plasmid, pCoHygro (Joharsen et al. 1989), that contains a gene for hygromycin resistance under the control of the constitutive Drosophila Copia LTR promoter using conventional calcium phcsphate-DNA coprecipitation techniques followed by selection with hygromycin B (Johansen et al. 1989). Expression of sodium channels in selected cell cultures is elicited by exposure to copper sulfate (Johansen et al. 1989). Expressed calcium-permeable sodium channels are detected and quantified initially in such cells using radioligand (e.g., [$^3$H]saxitoxin) binding assays. Expressed channels are also detected in assays of $^{45}Ca^{2+}$ influx into cells and the modification of such influx by agents known to act on sodium channels. Other experiments can employ fluorescent probes of intracellular calcium and can be used to evaluate the array of sodium channel-directed agents used in experiments with oocytes (see above) to determine the breadth of ligand—sodium channel interactions that can be detected successfully in fluorescence assays. These studies can be expanded by using bioluminescence-based detection of calcium influx, by coexpression of both the mutated sodium channel gene and the commercially-available aequorin gene (Sea-Lite Corporation).

The expression of these channels in cultured cells, coupled with fluorescence- or bioluminescence-based assays of calcium transport, offers a novel and greatly improved method for target-based screening for novel sodium channel ligands. In particular, the use of calcium flux as a reporter for sodium channel function permits the use of a single method of assay to assess the action of a variety of compounds that affect sodium channel function at multiple sodium channel domains without the need for prior knowledge of the specific sodium channel binding domain that is targeted by any given compound.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Names and sequences of oligonucleotide primers.

| Name | Sequence | |
|---|---|---|
| A1 | 5'-CGGTTGGGCTTTCCTGTC-3' | SEQ ID NO:5 |
| A2 | 5'-GGGAATTCRAADATRTTCCANCCYTC-3' | SEQ ID NO:6 |
| B1 | 5'-CCCGARGAYATHGAYCYNTAYTA-3' | SEQ ID NO:7 |
| B2 | 5'-CGTATCGCCTCCTCCTCG-3' | SEQ ID NO:8 |
| C1 | 5'-GGGTCTAGATHTTYGCNATHTTYGGNATG-3' | SEQ ID NO:9 |
| C2 | 5'-GGGGAATTCNGGRTCRAAYTGYTGCCA-3' | SEQ ID NO:10 |
| D1 | 5'-GGGTCTAGARGANCARAARAARTAYTA-3' | SEQ ID NO:11 |
| D2 | 5'-TCATACTTTGGCCCAATGTC-3' | SEQ ID NO:12 |
| E1 | 5'-CCCGAATTAGAGAAGGTGCTG-3' | SEQ ID NO:13 |
| E2 | 5'-ACTATTGCTTGTGGTCGCCAC-3' | SEQ ID NO:14 |
| F1 | 5'-CATCNTTRGCNGCNTAGACNATGAC-3' | SEQ ID NO:15 |
| F2 | 5'-GATTGAATGGATCGAGCAGCC-3' | SEQ ID NO:16 |
| G1 | 5'-CGTTTCTCCTTTCATATCTAG-3' | SEQ ID NO:17 |
| G2 | 5'-GGAGBGGBGGNCKBGGNCKNGCTCA-3' | SEQ ID NO:18 |
| H1 | 5'-GAGGAATTCGAGAAACGCGACGTCAGC-3' | SEQ ID NO:27 |
| H2 | 5'-CCCGCATGCTCAGACATCTGCCGTCCTGG-3' | SEQ ID NO:28 |
| I1 | 5'-CCTCCCGGGATGACAGAAGATTCCGACTCGATATCTGAG-3' | SEQ ID NO:29 |
| I2 | 5'-TCGGCATGCCAGTCGGCCGGATAGTCGTCG-3' | SEQ ID NO:30 |

Designation cf oligonucleotide mixtures:
B = G + T + C;
D = G + A + T;
H = A + T + C;
K = G + T;
N = A + C + G + T;
R = A + G;
Y = C + T.

LIST OF REFERENCES CITED

Bayer, E. A., et al., *Meth Enzym* 62:308 (1979). Bloomquist, J. R. and Soderlund, D. M., *Mol Pharmacol* 33:543–550 (1988).

Bordo, D. and Argos, P., *J Mol Biol* 217:721–729 (1991).

Brown, G. B., *Int Rev Neurobiol* 29:77–116 (1988). Campbell, A. M., "Monoclonal Antibody Technology: Laboratory Techniques in Biochemistry and Molecular Biology", Elsevier Science Publishers, Amsterdam, The Netherlands (1984).

Capecchi, M., *Cell* 22:479–488 (1980).

Catterall, W. A., *Physiological Reviews* 72(4):S14–S48 (1992).

Chomczynski, P. and Sacchi, N., *Anal Biochem.* 162:156–159 (1987).

Daniell, L. C., et al., *J Neurochem* 41:1455–1459 (1983).

Deecher, D. C. and Soderlund, D. M., *Pestic Biochem Physiol* 39:130–137 (1991).

Eldefrawi et al., *FASEB J* 1:262–271 (1987).

Engval, E. et al., *Immunol* 109:129 (1972).

Feng, G., et al., *Cell* 82:1001–1011 (1995).

French, S. and Robson, B., *J Molecular Evolution* 19:171–175 (1983).

Frohman, M. A. and Martin G. R., *Technique* 1:165–170 (1989).

Goding, J. W., *J Immunol Meth* 13:215 (1976).

Goldin, A. L., *Meth Enzymol* 207:266–297 (1992).

Grynkiewicz, G., et al., *J Biol Chem* 260:3440–3450 (1985).

Harvey, R. J. and Darlison, M. G., *Nucl Acids Res* 19:4002 (1991).

Heinemann, S. H., et al., *Nature* 356:441–443 (1992).

Henderson, J. E., et al., *Insect Biochem Mol Biol* 24:363–371 (1994).

Johansen, H., et al., *Genes & Development* 3:882–889 (1989).

Kallen, R. G., et al., *Mol Neurobiol* 7:383–428 (1993).

Kemp, B. E. and Pearson, R. B., *Trends Biochem Sci* 15:342–346 (1990).

Klein, T. M., et al., *Nature* 327:70–73 (1987).

Knight, M. R., et al., *FEBS Lett* 282:405–408 (1991).

Knipple, D. C., et al., *Proc Natl Acad Sci USA* 91:2483–2487 (1994).

Knipple, D. C., et al., *Arch Insect Biochem Physiol* 16:45–53 (1991).

Kornfeld, R. and Kornfeld, S., *Annu Rev Biochem* 54:931–664 (1985).

Loughney, K., et al., *Cell* 58:1143–1154 (1989).

Lutz, et al., *Exp Cell Res* 175:109–124 (1988).

Mannino, R. J. and Gould-Fogerite, S., *BioTechniques* 6:682–690 (1988).

Millar, N. S., et al., *Proc R Soc Lond B* 258:307–314 (1994).

Miller, L. K., *Annu Rev Microbiol* 42:177–199 (1988).

Miller, L. K., *Bioessays* 11:91–95 (1989).

O'Dowd, D. K., et al., *J Neurosci* 15:4005–4012 (1995).

Ottea, J. A., et al., *Mol Pharmacol* 36:280–284 (1989).

Prasher, D., et al., *Biochem Biophys Res Commun* 126:1259–1268 (1985).

Rauh et al., *Trends in Pharmacol Sci* 11:325–329 (1990).

Saiki, R. K., et al., *Science* 239:487–491 (1988).

Sambrook et al. Molecular Cloning: A Laboratory Manual, 2d Edition, Cold Spring Harbor Laboratory Press, Cold Spring Harbor, N.Y. (1989).

Sang, J. H., *Adv Cell Culture* 1:125–182 (1981).

Sanger, F., et al., *Proc Natl Acad Sci USA* 74:5463–5467 (1977).

Sawicki, R. M., *Nature* 275(5679):443–444 (1978).

Sheu, Y. A., et al., *Anal Biochem* 209:343–347 (1993).

Shigekawa, K. and Dower, W. J., *BioTechniques* 6:742–751 (1988).

Smith, G. E., et al., *Mol Cell Biol* 3:2156–2165 (1983).

Soderlund, D. M., et al., *Pestic Sci* 26:359–374 (1989a).

Soderlund, D. M. and Bloomquist, J. R., *Annu Rev Entomol* 34:77–96 (1989b).

Soderlund, D. M., et al., *Comp Biochem Physiol* 94C:255–260 (1989c).

Soderlund, D. M., and Knipple, D. C., in *Molecular Action of Insecticides on Ion Channels*, eds. Clark, J. M., American Chemical Society, Washington, D.C., pp.97–108 (1994).

St. Groth, et al., *J Immunol Methods* 35:1–21 (1980).
Sternberger, L. A., et al., *J Histochem Cytochem* 18:315 (1970).
Stuhmer, W., *Meth Enzymol* 207:319–339 (1992).
Taglialatela, M., et al., *Biophys J* 61:78–82 (1992).
Taylor, W. R., *J Theor Biol* 119:205–218 (1986).
Thackeray, J. R. and Ganetzky, B., *J. Neurosci* 14:2569–2578 (1994).
Thackeray, J. R. and Ganelzky, B., *Genetics* 141:203–214 (1995).
Tsien, R. Y., *Trends Neurosci* 11:419–424 (1988).
Williamson, M. S., et al., *Mol Gen Genet* 240:17–22 (1993).

What is claimed is:

1. An isolated nucleic acid molecule encoding a voltage-sensitive sodium channel of an insect having a mutation therein which renders the sodium channel encoded by said nucleic acid molecule permeable to calcium.

2. The isolated nucleic acid molecule of claim 1 wherein said nucleic acid is deoxyribonucleic acid.

3. The isolated nucleic acid molecule of claim 1 wherein said insect is *Musca domestica*.

4. The isolated nucleic acid molecule of claim 1 wherein said insect is *Drosophila melanogaster*.

5. The isolated nucleic acid molecule of claim 1 wherein said insect is *Heliothis virescens*.

6. The isolated nucleic acid molecule of claim 1 wherein said nucleic acid is ribonucleic acid.

7. A cell comprising the nucleic acid molecule of claim 1.

8. An expression vector comprising the nucleic acid molecule of claim 1.

9. A method of producing a calcium permeable voltage-sensitive sodium channel, said method comprising:
    introducing the nucleic acid molecule of claim 1 into a cell; and
    allowing said cell to express said nucleic acid molecule resulting in the production of a calcium permeable voltage-sensitive sodium channel in said cell.

10. A method of producing a calcium permeable voltage-sensitive sodium channel, said method comprising:
    introducing the nucleic acid molecule of claim 1 and a second nucleic acid molecule encoding a tip E protein into a cell; and
    allowing said cell to coexpress said nucleic acid molecule and said second nucleic acid molecule, resulting in the production of a calcium permeable voltage-sensitive sodium channel in said cell.

11. An isolated fragment of the nucleic acid molecule of claim 1 wherein said fragment includes said mutation and wherein said fragment consists of at least 10 nucleotides.

12. The isolated nucleic acid molecule of claim 2 wherein said deoxyribonucleic acid is cDNA.

13. The isolated nucleic acid molecule of claim 3 wherein said nucleic acid molecule has a nucleotide sequence selected from the group consisting of: SEQ ID NO:1 having a mutation at one or more of nucleotides 4489–4491; SEQ ID NO:1 having a mutation at one or more of nucleotides 5368–5370; SEQ ID NO:1 having a mutation at one or more of nucleotides 4489–4491 and a mutation at one or more of nucleotides 5368–5370; SEQ ID NO:2 having a mutation at one or more of nucleotides 4489–4491; SEQ ID NO:2 having a mutation at one or more of nucleotides 5368–5370; and SEQ ID NO:2 having a mutation at one or more of nucleotides 4489–4491 and a mutation at one or more of nucleotides 5368–5370.

14. The isolated nucleic acid molecule of claim 3 wherein said nucleic acid molecule encodes an amino acid sequence selected from the group consisting of: SEQ ID NO:3 having a mutation at amino acid residue 1497; SEQ ID NO:3 having a mutation at amino acid residue 1790; SEQ ID NO:3 having a mutation at amino acid residue 1497 and a mutation at amino acid residue 1790; SEQ ID NO:4 having a mutation at amino acid residue 1497; SEQ ID NO:4 having a mutation at amino acid residue 1790; and SEQ ID NO:4 having a mutation at amino acid residue 1497 and a mutation at amino acid residue 1790.

15. The isolated nucleic acid molecule of claim 14 wherein each of said mutations comprises a substitution of glutamate for the amino acid residue.

16. The isolated nucleic acid molecule of claim 4 wherein said nucleic acid molecule has a nucleotide sequence selected from the group consisting of: SEQ ID NO:24 having a mutation a one or more of nucleotides 4432–4434; SEQ ID NO:24 having a mutation at one or more of nucleotides 5311–5313; and SEQ ID NO:24 having a mutation at one or more of nucleotides 4432–4434 and a mutation at one or more of nucleotides 5311–5313.

17. The isolated nucleic acid molecule of claim 4 wherein said nucleic acid molecule encodes an amino acid sequence selected from the group consisting of: SEQ ID NO:23 having a mutation at amino acid residue 1478; SEQ ID NO:23 having a mutation at amino acid residue 1771; and SEQ ID NO:23 having a mutation at amino acid residue 1478 and a mutation at amino acid residue 1771.

18. The isolated nucleic acid molecule of claim 17 wherein each of said mutations comprises a substitution of glutamate for the amino acid residue.

19. The isolated nucleic acid molecule of claim 5 wherein said nucleic acid molecule includes a nucleotide sequence selected from the group consisting of: SEQ ID NO:26 having a mutation at one or more of nucleotides 179–181; SEQ ID NO:26 having a mutation at one or more of nucleotides 1058–1060; and SEQ ID NO:26 having a mutation at one or more of nucleotides 179–181 and a mutation at one or more of nucleotidese 1058–1060.

20. The isolated nucleic acid molecule of claim 5 wherein said nucleic acid molecule encodes an amino acid sequence which includes a sequence selected from the group consisting of: SEQ ID NO:25 having a mutation at amino acid residue 60; SEQ ID NO:25 having a mutation at amino acid residue 353; and SEQ ID NO:25 having a mutation at amino acid residue 60 and a mutation at amino acid residue 353.

21. The isolated nicleic acid molecule of claim 20 wherein each of said mutations comprises a substitution of glutamate for the amino acid residue.

22. The isolated nucleic acid molecule of claim 6 wherein said ribonucleic acid is mRNA.

23. The cell of claim 7 wherein the cell is a Xenopus oocyte.

24. The cell of claim 7 wherein the cell is an insect cell line.

25. The cell of claim 24 wherein said insect cell line is selected from the group consisting of a *Drosophila Schneider* cell line, a Drosophila $K_c$ cell line, an Sf9 cell line, and a cell line from the eggs of *Trichoplusia ni* having all the identifying characteristics of BTI-TN-5-B1-4.

26. The expression vector of claim 8 wherein said expression vector is selected from the group consisting of a plasmid and a virus.

27. A cell comprising the expression vector of claim 8.

28. The expression vector of claim 26 wherein said virus is a baculovirus.

29. The cell of claim 27 wherein the cell is a Xenopus oocyte.

30. The cell of claim 27 wherein the cell is an insect cell line.

31. The cell of claim 30 wherein said insect cell line is selected from the group consisting of a *Drosophila Schneider* cell line, a Drosophila $K_c$ cell line, an Sf9 cell line, and a cell line from the eggs of *Trichoplusia ni* having all the identifying characteristics of BTI-TN-5-B1-4.

32. The method of claim 9 wherein the cell is a Xenopus oocyte.

33. The method of claim 9 wherein the cell is an insect cell line.

34. The method of claim 33 wherein said insect cell line is selected from the group consisting of a *Drosophila Schneider* cell, a Drosophila $K_c$ cell, an Sf9 cell, and a cell line from the eggs of *Trichoplusia ni* having all the identifying characteristics of BTI-TN-5-B1-4.

35. The method of claim 10 wherein the cell is a Xenopus oocyte.

36. The method of claim 10 wherein the cell is an insect cell line.

37. The method of claim 36 wherein said insect cell line is selected from the group consisting of a *Drosophila Schneider* cell, a Drosophila $K_c$ cell, an Sf9 cell, and a cell line from the eggs of *Trichoplusia ni* having all the identifying characteristics of BTI-TN-5-B1-4.

38. An isolated nucleic acid molecule containing the fragment of claim 11.

39. An isolated nucleic acid molecule encoding a calcium permeable voltage-sensitive sodium channel of an insect, said nucleic acid molecule encoding an amino acid sequence selected from the group consisting of: SEQ ID NO:3 having a mutation at amino acid residue 1497; SEQ ID NO:3 having a mutation at amino acid residue 1790; SEQ ID NO:3 having a mutation at am-no acid residue 1497 and a mutation at amino acid residue 1790; SEQ ID NO:4 having a mutation at amino acid residue 1497; SEQ ID NO:4 having a mutation at amino acid residue 1790; SEQ ID NO:4 having a mutation at amino acid residue 1497 and a mutation at amino acid residue 1790; SEQ ID NO:23 having a mutation at amino acid residue 1478; SEQ ID NO:23 having a mutation at amino acid residue 1771; SEQ ID NO:23 having a mutation at amino acid residue 1478 and a mutation at amino acid residue 1771; SEQ ID NO:25 having a mutation at amino acid residue 60; SEQ ID NO:25 having a mutation at amino acid residue 353; and SEQ ID NO:25 having a mutation at amino acid residue 60 and a mutation at amino acid residue 353.

* * * * *

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 6318 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
ATGACAGAAG  ATTCCGACTC  GATATCTGAG  GAAGAACGCA  GTTTGTTCCG  TCCCTTCACC      60
CGCGAATCAT  TGTTACAAAT  CGAACAACGT  ATCGCTGAAC  ATGAAAAACA  AAAGGAGCTG     120
GAAAGAAAGA  GAGCCGCCGA  AGGAGAGCAG  ATACGATATG  ATGACGAGGA  CGAAGATGAA     180
GGTCCACAGC  CGGATCCCAC  ACTTGAACAG  GGTGTGCCTA  TACCTGTTCG  AATGCAGGGC     240
AGCTTCCCGC  CGGAATTGGC  CTCCACTCCT  CTCGAGGATA  TCGATCCCTT  CTACAGTAAT     300
GTACTGACAT  TTGTAGTAAT  AAGTAAAGGA  AAGGATATTT  TTCGTTTTTC  TGCCTCAAAA     360
GCAATGTGGC  TGCTCGATCC  ATTCAATCCG  ATACGTCGTG  TAGCCATTTA  TATTTTAGTG     420
CATCCCTTGT  TTTCGTTATT  CATTATCACC  ACTATTCTAA  CTAATTGTAT  TTTAATGATA     480
ATGCCGACAA  CGCCCACGGT  CGAATCCACA  GAGGTGATAT  TCACCGGAAT  CTACACATTT     540
GAATCAGCTG  TTAAAGTGAT  GGCACGAGGT  TTCATTTTAT  GCCCGTTTAC  GTATCTTAGA     600
GATGCATGGA  ATTGGCTGGA  CTTCGTAGTA  ATAGCTTTAG  CTTATGTGAC  CATGGGCATA     660
GATTTAGGTA  ATCTCGCAGC  TTTGAGAACA  TTTAGGGTAC  TGCGAGCTCT  GAAAACCGTA     720
GCCATTGTGC  CAGGTCTAAA  AACCATTGTC  GGTGCTGTCA  TTGAATCTGT  AAAAAATCTA     780
CGCGATGTGA  TAATTTTGAC  AATGTTTTCC  CTGTCGGTGT  TCGCGCTGAT  GGGCCTACAA     840
ATCTATATGG  GTGTTCTAAC  ACAAAAGTGC  ATTAAACGAT  TCCCCCTGGA  CGGCAGTTGG     900
GGCAATCTGA  CCGATGAAAA  CTGGTTTCTA  CACAATAGCA  ACAGTTCCAA  TTGGTTTACG     960
GAGAACGATG  GCGAGTCATA  TCCGGTGTGC  GGGAATGTAT  CCGGTGCGGG  ACAATGCGGC    1020
GAGGATTACG  TCTGCCTGCA  GGGCTTCGGC  CCCAATCCCA  ACTACGACTA  CACCAGTTTC    1080
GATTCATTCG  GTTGGGCTTT  CCTGTCGGCG  TTTCGTCTCA  TGACCCAAGA  TTTCTGGGAG    1140
GATCTGTATC  AGCACGTGCT  GCAAGCAGCT  GGACCCTGGC  ACATGTTGTT  CTTTATAGTC    1200
ATCATCTTCC  TAGGTTCATT  CTATCTTGTG  AATTTGATTT  TGGCCATTGT  TGCCATGTCT    1260
TATGACGAAT  TGCAAAAGAA  GGCCGAAGAA  GAAGAGGCTG  CCGAGGAGGA  GGCGATACGA    1320
GAAGCTGAAG  AAGCGGCAGC  AGCCAAGGCG  GCCAAACTGG  AGGAGCGGGC  CAATGTAGCA    1380
GCTCAAGCGG  CTCAGGATGC  AGCGGATGCC  GCTGCGGCAG  CTCTGCATCC  CGAGATGGCA    1440
AAGAGTCCCA  CGTACTCTTG  CATTAGCTAT  GAACTGTTTG  TTGGCGGCGA  GAAGGGCAAC    1500
GATGACAACA  ACAAAGAGAA  GATGTCCATA  CGCAGCGTCG  AAGTGGAATC  GGAGTCGGTG    1560
```

```
AGCGTTATAC  AAAGACAACC  AGCACCTACC  ACAGCACCCG  CTACTAAAGT  CCGTAAAGTT  1620
AGCACGACTT  CCTTATCCTT  ACCTGGTTCA  CCATTTAACC  TACGCCGGGG  ATCACGTAGT  1680
TCACACAAGT  ACACAATACG  AAATGGGCGT  GGACGTTTTG  GTATACCAGG  TAGCGATCGC  1740
AAGCCATTGG  TACTGCAAAC  ATATCAGGAT  GCCCAGCAGC  ATTTGCCCTA  TGCCGATGAC  1800
TCGAATGCCG  TAACACCAAT  GTCCGAAGAG  AATGGTGCCA  TTATAGTACC  AGCCTACTAT  1860
TGTAATTTAG  GTTCTAGACA  TTCTTCATAT  ACCTCGCATC  AATCAAGAAT  CTCGTATACA  1920
TCACATGGTG  ATTTATTGGG  TGGCATGGCG  GCCATGGGTG  CCAGCACAAT  GACCAAAGAG  1980
AGCAAATTGC  GCAGTCGCAA  CACACGCAAT  CAATCAATCG  GTGCTGCAAC  CAATGGTGGC  2040
AGTAGTACGG  CTGGTGGTGG  CTATCCCGAT  GCCAATCACA  AGGAACAAAG  GGATTATGAA  2100
ATGGGTCAGG  ATTATACAGA  CGAAGCTGGC  AAAATAAAAC  ACCACGACAA  TCCTTTTATC  2160
GAGCCCGTCC  AAACTCAAAC  AGTGGTAGAC  ATGAAAGATG  TTATGGTCTT  AAATGATATC  2220
ATTGAACAAG  CCGCTGGTCG  GCATAGTCGT  GCTAGTGAAC  GAGGTGAGGA  CGATGACGAA  2280
GATGGTCCCA  CATTCAAGGA  CATCGCCCTC  GAATACATCC  TAAAAGGCAT  CGAAATCTTT  2340
TGTGTATGGG  ACTGTTGTTG  GGTGTGGTTA  AAATTTCAGG  AATGGGTGTC  CTTTATTGTG  2400
TTCGATCCAT  TCGTGGAGCT  CTTCATTACC  CTGTGTATTG  TGGTCAATAC  GATGTTTATG  2460
GCCATGGATC  ATCACGACAT  GAATCCGGAA  TTAGAGAAGG  TGCTGAAAAG  TGGTAACTAT  2520
TTCTTCACGG  CCACTTTTGC  AATTGAAGCC  AGCATGAAAC  TGATGGCCAT  GAGCCCGAAG  2580
TACTACTTCC  AGGAAGGCTG  GAACATTTTC  GATTTCATTA  TTGTGGCCTT  GTCTCTGCTG  2640
GAATTGGGCC  TGGAGGGTGT  CCAGGGCCTG  TCGGTGTTGA  GAAGTTTTCG  TTTGCTTCGT  2700
GTATTCAAAT  TGGCAAAATC  ATGGCCCACA  CTCAATTTAC  TCATTTCGAT  TATGGGCCGG  2760
ACAATGGGTG  CATTGGGTAA  TCTGACATTT  GTACTTTGCA  TTATCATCTT  CATCTTTGCC  2820
GTGATGGGAA  TGCAACTTTT  CGGAAAGAAC  TATATTGACC  ACAAGGATCG  CTTCAAGGAC  2880
CATGAATTAC  CGCGCTGGAA  CTTCACCGAC  TTCATGCACA  GCTTCATGAT  TGTGTTCCGA  2940
GTGCTGTGCG  GAGAGTGGAT  CGAGTCCATG  TGGGACTGCA  TGTATGTGGG  CGATGTCAGC  3000
TGTATACCCT  TCTTCTTGGC  CACGGTCGTG  ATAGGCAATC  TTGTGGTTCT  TAATCTTTTC  3060
TTAGCTTTGC  TTTTGTCCAA  CTTCGGTTCA  TCTAGTTTAT  CAGCCCCGAC  TGCCGACAAT  3120
GATACCAATA  AAATAGCAGA  GGCCTTCAAT  CGTATTGCTC  GTTTTAAGAA  CTGGGTGAAA  3180
CGTAATATTG  CCGATTGTTT  TAAGTTAATT  CGAAATAAAT  TGACAAATCA  AATAAGTGAC  3240
CAACCATCAG  AACATGGCGA  TAATGAACTG  GAGTTGGGTC  ATGACGAAAT  CATGGGCGAT  3300
GGCTTGATCA  AAAAGGGTAT  GAAGGGCGAG  ACCCAGCTGG  AGGTGGCCAT  TGGCGATGGC  3360
ATGGAGTTCA  CGATACATGG  CGATATGAAA  AACAACAAGC  CGAAGAAATC  AAAATTCATG  3420
AACAACACAA  CGATGATTGG  AAACTCAATA  AACCACCAAG  ACAATAGACT  GGAACATGAG  3480
CTAAACCATA  GAGGTTTGTC  CATACAGGAC  GATGACACTG  CCAGCATTAA  CTCATATGGT  3540
AGCCATAAGA  ATCGACCATT  CAAGGACGAG  AGCCACAAGG  GCAGCGCCGA  GACCATCGAG  3600
GGCGAGGAGA  AACGCGACGT  CAGCAAAGAG  GACCTCGGCC  TCGACGAGGA  ACTGGACGAG  3660
GAGGCCGAGG  GCGATGAGGG  CCAGCTGGAT  GGTGACATTA  TCATTCATGC  GCAAAACGAC  3720
GACGAGATAA  TCGACGACTA  TCCGGCCGAC  TGTTTCCCCG  ACTCGTACTA  CAAGAAGTTT  3780
CCGATCTTGG  CCGGCGACGA  GGACTCGCCG  TTCTGGCAAG  GATGGGGCAA  TTTACGACTG  3840
AAAACTTTTC  AATTAATTGA  AAATAAATAT  TTTGAAACCG  CAGTTATCAC  TATGATTTTA  3900
ATGAGTAGCT  TAGCTTTGGC  CTTAGAAGAT  GTTCATTTAC  CCGATCGACC  TGTCATGCAG  3960
```

```
GATATACTGT  ACTACATGGA  CAGGATATTT  ACGTGATAT   TCTTTTTGGA  GATGTTGATC    4020
AAATGGTTGG  CCCTGGGCTT  TAAGGTTTAC  TTCACCAATG  CCTGGTGTTG  GCTGGATTTC    4080
GTGATTGTCA  TGCTATCGCT  TATAAATTTG  GTTGCCGTTT  GGTCGGGCTT  AAATGATATA    4140
GCCGTGTTTA  GATCAATGCG  CACACTGCGC  GCCCTAAGGC  CATTGCGTGC  TGTCTCTAGA    4200
TGGGAGGGTA  TGAAAGTTGT  CGTGAATGCG  CTGGTTCAAG  CTATACCGTC  CATCTTCAAT    4260
GTGCTATTGG  TGTGTCTGAT  ATTTTGGCTT  ATTTTTGCCA  TTATGGGAGT  ACAGCTTTTT    4320
GCTGGAAAAT  ATTTTAAGTG  TAAAGATGGT  AATGACACTG  TGCTGAGCCA  TGAAATCATA    4380
CCGAATCGTA  ATGCCTGCAA  AAGTGAAAAC  TACACCTGGG  AAAATTCGGC  AATGAACTTC    4440
GATCATGTAG  GTAATGCGTA  TCTCTGTCTA  TTTCAAGTGG  CCACCTTTAA  GGGCTGGATC    4500
CAGATTATGA  ACGATGCCAT  TGATTCACGA  GAGGTGGACA  AGCAGCCGAT  CCGAGAAACC    4560
AATATCTACA  TGTATTTATA  TTTCGTATTC  TTCATTATAT  TTGGATCATT  TTTCACACTC    4620
AATCTGTTCA  TTGGTGTTAT  CATTGATAAT  TTAATGAAC   AAAAGAAGAA  AGCTGGTGGA    4680
TCATTAGAAA  TGTTCATGAC  AGAAGATCAG  AAAAAGTACT  ATAATGCTAT  GAAAAAGATG    4740
GGCTCTAAAA  AACCATTAAA  AGCCATTCCA  AGACCGAGGT  GGCGACCACA  AGCAATAGTA    4800
TTCGAAATAG  TTACAGATAA  AAAATTCGAT  ATAATCATTA  TGTTGTTCAT  TGGCTTAAAC    4860
ATGTTTACCA  TGACCCTCGA  TCGGTACGAC  GCCTCCGAGG  CGTACAACAA  TGTCCTCGAC    4920
AAACTCAATG  GGATATTCGT  AGTTATTTTC  AGTGGCGAAT  GTCTATTAAA  AATATTCGCT    4980
TTACGATATC  ACTATTTCAA  AGAGCCATGG  AATTTATTTG  ATGTAGTAGT  TGTCATTTTA    5040
TCCATCTTAG  GTCTTGTACT  CAGCGACATC  ATTGAGAAGT  ATTTCGTATC  GCCGACACTG    5100
CTCCGTGTGG  TGAGAGTGGC  CAAAGTGGGT  CGTGTCCTGC  GTTTAGTCAA  GGGTGCCAAG    5160
GGTATCCGGA  CGTTGCTGTT  CGCGTTAGCC  ATGTCGTTGC  CTGCCTTATT  CAACATTTGT    5220
CTGTTGCTGT  TCTTGGTGAT  GTTCATCTTT  GCTATCTTTG  GCATGTCCTT  CTTCATGCAT    5280
GTCAAAGAGA  AGAGCGGCAT  AAATGCTGTG  TATAATTTTA  AGACATTTGG  CCAAAGTATG    5340
ATATTGCTGT  TTCAGATGTC  TACCTCAGCC  GGTTGGGATG  GTGTGTTAGA  TGCCATTATC    5400
AATGAGGAAG  ATTGCGATCC  ACCCGACAAC  GACAAGGGCT  ATCCGGGCAA  TTGTGGTTCA    5460
GCGACTGTTG  GAATTACGTT  TCTCCTTTCA  TATCTAGTTA  TAAGCTTTTT  GATAGTTATT    5520
AATATGTACA  TTGCTGTCAT  TCTCGAGAAC  TATAGCCAGG  CTACGGAGGA  TGTACAGGAG    5580
GGTCTCACCG  ACGACGATTA  CGATATGTAC  TACGAGATTT  GGCAACAATT  CGATCGGAG    5640
GGCACCCAGT  ACATACGCTA  CGACCAGCTG  TCCGAGTTTC  TGGACGTGCT  GGAGCCGCCG    5700
CTGCAGATCC  ACAAGCCGAA  CAAGTACAAA  ATCATATCGA  TGGACATGCC  GATATGTCGG    5760
GGCGACATGA  TGTACTGTGT  GGATATATTG  GATGCCCTGA  CCAAGGACTT  CTTTGCGCGC    5820
AAGGGTAATC  CGATCGAGGA  GACGGGTGAA  ATTGGTGAGA  TAGCGGCGCG  ACCGGACACC    5880
GAGGGCTATG  ATCCGGTGTC  GTCAACACTG  TGGCGCCAGC  GTGAGGAGTA  CTGCGCCAAG    5940
CTGATACAGA  ATGCGTGGCG  GCGTTACAAG  AATGGCCCAC  CCAGGAGGG   TGATGAGGGC    6000
GAGGCGGCTG  GTGGCGAAGA  TGGTGCTGAA  GGCGGTGAGG  GTGAAGGAGG  CAGCGGCGGC    6060
GGCGGCGGTG  ATGATGGTGG  CTCAGCGACA  GGAGCAACGG  CGGCGGCGGG  AGCCACATCA    6120
CCCTCAGATC  CAGATGCCGG  CGAAGCAGAT  GGTGCCAGCG  TCGGCGGCCC  CCTTAGTCCG    6180
GGCTGTGTTA  GTGGCGGCAG  TAATGGCCGC  CAAACGGCCG  TACTGGTCGA  AAGCGATGGT    6240
TTTGTTACAA  AAAACGGTCA  TAAGGTTGTA  ATACACTCGA  GATCGCCGAG  CATAACATCC    6300
AGGACGGCAG  ATGTCTGA                                                     6318
```

( 2 ) INFORMATION FOR SEQ ID NO:2:

( i ) SEQUENCE CHARACTERISTICS:
        ( A ) LENGTH: 6315 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
ATGACAGAAG ATTCCGACTC GATATCTGAG GAAGAACGCA GTTTGTTCCG TCCCTTCACC        60
CGCGAATCAT TGTTACAAAT CGAACAACGT ATCGCTGAAC ATGAAAAACA AAAGGAGCTG       120
GAAAGAAAGA GAGCCGCCGA AGGAGAGCAG ATACGATATG ATGACGAGGA CGAAGATGAA       180
GGTCCACAGC CGGATCCCAC ACTTGAACAG GGTGTGCCTA TACCTGTTCG AATGCAGGGC       240
AGCTTCCCGC CGGAATTGGC CTCCACTCCT CTCGAGGATA TCGATCCCTT CTACAGTAAT       300
GTACTGACAT TTGTAGTAAT AAGTAAGGA AAGGATATTT TTCGTTTTTC TGCCTCAAAA        360
GCAATGTGGC TGCTCGATCC ATTCAATCCG ATACGTCGTG TAGCCATTTA TATTTAGTG        420
CATCCCTTGT TTTCGTTATT CATTATCACC ACTATTCTAA CTAATTGTAT TTAATGATA        480
ATGCCGACAA CGCCCACGGT CGAATCCACA GAGGTGATAT TCACCGGAAT CTACACATTT       540
GAATCAGCTG TTAAAGTGAT GGCACGAGGT TTCATTTTAT GCCCGTTTAC GTATCTTAGA       600
GATGCATGGA ATTGGCTGGA CTTCGTAGTA ATAGCTTTAG CTTATGTGAC CATGGGCATA       660
GATTTAGGTA ATCTCGCAGC TTTGAGAACA TTTAGGGTAC TGCGAGCTCT GAAAACCGTA       720
GCCATTGTGC CAGGTCTAAA AACCATTGTC GGTGCTGTCA TTGAATCTGT AAAAAATCTA       780
CGCGATGTGA TAATTTTGAC AATGTTTTCC CTGTCGGTGT TCGCGCTGAT GGGCCTACAA       840
ATCTATATGG GTGTTCTAAC ACAAAAGTGC ATTAAACGAT TCCCCCTGGA CGGCAGTTGG       900
GGCAATCTGA CCGATGAAAA CTGGTTTCTA CACAATAGCA ACAGTTCCAA TTGGTTTACG       960
GAGAACGATG GCGAGTCATA TCCGGTGTGC GGGAATGTAT CCGGTGCGGG ACAATGCGGC      1020
GAAGATTACG TCTGCCTGCA GGGCTTCGGC CCCAATCCCA ACTACGACTA CACCAGTTTC      1080
GACTCATTCG GTTGGGCTTT CCTGTCGGCG TTTCGTCTCA TGACCCAAGA TTTCTGGGAG      1140
GATCTGTATC AGCACGTGCT GCAAGCAGCT GGACCCTGGC ACATGTTGTT CTTTATAGTC      1200
ATCATCTTCC TAGGTTCATT CTATCTTGTG AATTTGATTT TGGCCATTGT TGCCATGTCT      1260
TATGACGAAT TGCAAAAGAA GGCCGAAGAA GAAGAGGCTG CCGAGGAGGA GGCGATCCGA      1320
GAAGCTGAAG AAGCGGCAGC AGCCAAGGCG GCCAAACTGG AGGAGCGGGC CAATGTAGCA      1380
GCTCAAGCGG CTCAGGATGC AGCGGATGCC GCTGCGGCAG CTCTGCATCC CGAGATGGCA      1440
AAGAGTCCCA CGTACTCTTG CATTAGCTAT GAACTGTTTG TTGGCGGCGA GAAGGGCAAC      1500
GATGACAACA ACAAGGAGAA GATGTCGATA CGCAGCGTCG AAGTGGAATC GGAGTCGGTG      1560
AGCGTTATAC AAAGACAACC AGCACCTACC ACAGCACCCG CTACTAAAGT CCGTAAAGTT      1620
AGCACGACTT CCTTATCCTT ACCTGGTTCA CCATTTAACC TACGCCGGGG ATCACGTAGT      1680
TCACACAAGT ACACAATACG AAATGGGCGT GGACGTTTTG GTATACCAGG TAGCGATCGC      1740
AAGCCATTGG TACTGCAAAC ATATCAGGAT GCCCAGCAGC ATTTGCCCTA TGCCGATGAC      1800
TCGAATGCCG TAACACCAAT GTCCGAAGAG AATGGTGCCA TTATAGTACC AGCCTACTAT      1860
TGTAATTTAG GTTCTAGACA TTCTTCATAT ACCTCGCATC AATCAGAAT CTCGTATACA       1920
TCACATGGTG ATTTATTGGG TGGCATGGCG GCCATGGGTG CCAGCACAAT GACCAAAGAG      1980
AGCAAATTGC GCAGTCGCAA CACACGCAAT CAATCAATCG GTGCTGCAAC CAATGGTGGC      2040
```

| | | | | | | |
|---|---|---|---|---|---|---|
| AGTAGTACGG | CCGGTGGTGG | CTATCCCGAT | GCCAATCACA | AGGAACAAAG | GGATTATGAA | 2100 |
| ATGGGTCAGG | ATTATACAGA | CGAAGCTGGC | AAAATAAAAC | ACCACGACAA | TCCTTTTATC | 2160 |
| GAGCCCGTCC | AAACTCAAAC | AGTGGTAGAC | ATGAAGATG | TTATGGTCTT | AAATGATATC | 2220 |
| ATTGAACAAG | CCGCTGGTCG | GCATAGTCGT | GCTAGTGAAC | GAGGTGAGGA | CGATGACGAA | 2280 |
| GATGGTCCCA | CATTCAAGGA | CATCGCCCTC | GAATATATCC | TAAAAGGCAT | CGAAATCTTT | 2340 |
| TGTGTATGGG | ACTGTTGTTG | GGTGTGGTTA | AAATTTCAGG | AATGGGTCTC | CTTTATTGTG | 2400 |
| TTCGATCCAT | TCGTGGAGCT | CTTCATTACC | CTGTGTATTG | TGGTCAATAC | AATGTTCATG | 2460 |
| GCCATGGATC | ATCACGACAT | GAATCCGGAA | TTGGAGAAGG | TGCTGAAAAG | TGGTAACTAT | 2520 |
| TTCTTCACGG | CCACTTTTGC | AATTGAGGCC | AGCATGAAAC | TGATGGCCAT | GAGCCCGAAG | 2580 |
| TACTACTTCC | AGGAAGGCTG | GAACATTTTC | GATTTCATTA | TTGTGGCCTT | GTCTCTGCTG | 2640 |
| GAATTGGGCC | TGGAGGGTGT | CCAGGGCCTG | TCGGTGTTGA | GAAGTTTTCG | TTTGCTTCGT | 2700 |
| GTATTCAAAT | TGGCAAAATC | ATGGCCCACA | CTGAATTTAC | TCATTTCGAT | TATGGGCCGG | 2760 |
| ACAATGGGTG | CATTGGGTAA | TCTGACATTT | GTACTTTGCA | TTATCATCTT | CATCTTTGCC | 2820 |
| GTGATGGGAA | TGCAACTTTT | CGGAAAGAAC | TATATTGACC | ACAAGGATCG | CTTCAAGGAC | 2880 |
| CATGAATTAC | CGCGCTGGAA | TTTCACCGAC | TTCATGCACA | GCTTCATGAT | TGTGTTCCGA | 2940 |
| GTGCTGTGCG | GAGAGTGGAT | CGAGTCCATG | TGGGACTGCA | TGTATGTGGG | CGATGTCAGC | 3000 |
| TGTATACCCT | TCTTCTTGGC | CACGGTCGTG | ATCGGCAATT | TTGTGGTTCT | TAATCTTTTC | 3060 |
| TTAGCTTTGC | TTTTGTCCAA | CTTCGGTTCA | TCTAGTTTAT | CAGCCCCGAC | TGCCGACAAT | 3120 |
| GATACCAATA | AAATAGCAGA | GGCCTTCAAT | CGTATTGCTC | GTTTTAAGAA | CTGGGTGAAA | 3180 |
| CGTAATATTG | CCGATTGTTT | TAAGTTAATT | CGAAATAAAT | TGACAAATCA | AATAAGTGAC | 3240 |
| CAACCATCAG | AACATGGCGA | TAATGAACTG | GAGTTGGGTC | ATGACGAAAT | CATGGGCGAT | 3300 |
| GGCTTGATCA | AAAAGGGTAT | GAAGGGCGAG | ACCCAGCTGG | AGGTGGCCAT | TGGCGATGGC | 3360 |
| ATGGAGTTCA | CGATACATGG | CGATATGAAA | AACAACAAGC | CAAGAAATC | AAAATTCATA | 3420 |
| AACAACACAA | CGATGATTGG | AAACTCAATA | AACCACCAAG | ACAATAGACT | GGAACATGAG | 3480 |
| CTAAACCATA | GAGGTTTGTC | CATACAGGAC | GATGACACTG | CCAGCATTAA | CTCATATGGT | 3540 |
| AGCCATAAGA | ATCGACCATT | CAAGGACGAG | AGCCACAAGG | GCAGCGCCGA | GACCATCGAG | 3600 |
| GGCGAGGAGA | AACGCGACGT | CAGCAAAGAG | GACCTCGGCC | TCGACGAGGA | ACTGGACGAG | 3660 |
| GAGGCCGAGG | GCGATGAGGG | CCAGCTGGAT | GGTGACATCA | TCATTCATGC | CCAAAACGAC | 3720 |
| GACGAGATAA | TCGACGACTA | TCCGGCCGAC | TGTTTCCCCG | ACTCGTACTA | CAAGAAGTTT | 3780 |
| CCGATCTTGG | CCGGCGACGA | GGACTCGCCG | TTCTGGCAAG | GATGGGCAA | TTTACGACTG | 3840 |
| AAAACTTTTC | AATTAATTGA | AAATAAATAT | TTTGAAACCG | CAGTTATCAC | TATGATTTTA | 3900 |
| ATGAGTAGCT | TAGCTTTGGC | CTTAGAAGAT | GTTCATTTAC | CCGATCGACC | TGTCATGCAG | 3960 |
| GATATACTGT | ACTACATGGA | CAGGATATTT | ACGGTGATAT | TCTTTTTGGA | GATGTTGATC | 4020 |
| AAATGGTTGG | CCCTGGGCTT | TAAGGTCTAC | TTCACCAATG | CCTGGTGTTG | GCTGGATTTC | 4080 |
| GTGATTGTCA | TGCTATCGCT | TATAAATTTG | GTTGCCGTTT | GGTCGGGCTT | AAATGATATA | 4140 |
| GCCGTGTTTA | GATCAATGCG | CACACTGCGC | GCCCTAAGGC | CATTGCGTGC | TGTCTCTAGA | 4200 |
| TGGGAGGGTA | TGAAAGTTGT | CGTGAATGCG | CTGGTTCAAG | CTATACCGTC | CATCTTCAAT | 4260 |
| GTGCTATTGG | TGTGTCTGAT | ATTTTGGCTT | ATTTTGCCA | TTATGGGAGT | ACAGCTTTTT | 4320 |
| GCTGGAAAAT | ATTTTAAGTG | TAAAGATGGT | AATGACACTG | TGCTGAGCCA | TGAAATCATA | 4380 |
| CCGAATCGTA | ATGCCTGCAA | AAGTGAAAAC | TACACCTGGG | AAAATTCGGC | AATGAACTTC | 4440 |

| | | | | | |
|---|---|---|---|---|---|
| GATCATGTAG | GTAATGCGTA | TCTCTGTCTA | TTTCAAGTGG | CCACCTTTAA | GGGCTGGATC | 4500
| CAGATTATGA | ACGATGCCAT | TGATTCACGA | GAGGTGGACA | AGCAGCCGAT | CCGAGAAACC | 4560
| AATATCTACA | TGTATTTATA | TTTCGTATTC | TTCATTATAT | TTGGATCATT | TTTCACACTC | 4620
| AATCTGTTCA | TTGGTGTTAT | CATTGATAAT | TTTAATGAAC | AAAAGAAGAA | AGCAGGTGGA | 4680
| TCATTAGAAA | TGTTCATGAC | AGAAGATCAG | AAAAAGTACT | ATAATGCTAT | GAAAAAGATG | 4740
| GGCTCTAAAA | AACCATTAAA | AGCCATTCCA | AGACCGAGGT | GGCGACCACA | AGCAATAGTA | 4800
| TTCGAAATAG | TTACAGATAA | AAAATTCGAT | ATAATCATTA | TGTTGTTCAT | TGGCTTAAAC | 4860
| ATGTTTACCA | TGACCCTCGA | TCGGTACGAC | GCCTCCGAGG | CGTACAACAA | TGTCCTCGAC | 4920
| AAACTCAATG | GGATATTCGT | AGTTATTTTC | AGTGGCGAAT | GTCTATTAAA | AATATTCGCT | 4980
| TTACGATATC | ACTATTTCAA | AGAGCCATGG | AATTTATTTG | ATGTAGTAGT | TGTCATTTTA | 5040
| TCCATCTTAG | GTCTTGTACT | CAGCGACATC | ATTGAGAAGT | ATTTCGTATC | GCCGACACTG | 5100
| CTCCGTGTGG | TGAGAGTGGC | CAAAGTGGGT | CGTGTCCTGC | GTTTAGTCAA | GGGTGCCAAG | 5160
| GGTATCCGGA | CGTTGCTGTT | CGCGTTAGCC | ATGTCGTTGC | CTGCCTATT | CAACATTTGT | 5220
| CTGTTGCTGT | TCTTGGTGAT | GTTCATCTTT | GCTATCTTTG | GCATGTCCTT | CTTCATGCAT | 5280
| GTCAAAGAGA | AGAGCGGCAT | AAATGCTGTG | TATAATTTTA | AGACATTTGG | CCAAAGTATG | 5340
| ATATTGCTGT | TTCAGATGTC | TACCTCAGCC | GGTTGGGATG | GTGTGTTAGA | TGCCATTATC | 5400
| AATGAGGAAG | ATTGCGATCC | ACCCGACAAC | GACAAGGGCT | ATCCGGGCAA | TTGTGGTTCA | 5460
| GCGACTGTTG | GAATTACGTT | TCTCCTTTCA | TATCTAGTTA | TAAGCTTTTT | GATAGTTATT | 5520
| AATATGTACA | TTGCTGTCAT | TCTCGAGAAC | TATAGCCAGG | CTACGGAGGA | TGTACAGGAG | 5580
| GGTCTCACCG | ACGACGACTA | TGATATGTAC | TACGAGATTT | GGCAACAATT | CGATCCGGAG | 5640
| GGTACCCAGT | ACATAAGATA | CGACCAGCTG | TCCGAGTTCC | TGGACGTGCT | GGAGCCGCCG | 5700
| CTGCAGATCC | ACAAGCCGAA | CAAGTACAAA | ATCATATCGA | TGGACATGCC | GATATGTCGG | 5760
| GGCGACATGA | TGTACTGTGT | GGATATATTG | GATGCCCTGA | CCAAGGACTT | CTTTGCGCGC | 5820
| AAGGGTAATC | CGATCGAGGA | GACGGGTGAA | ATTGGTGAGA | TTGCGGCGCG | ACCGGACACC | 5880
| GAGGGCTATG | ATCCGGTGTC | GTCGACACTG | TGGCGCCAGC | GTGAGGAGTA | CTGCGCCAAG | 5940
| CTGATACAGA | ATGCGTGGCG | GCGTTACAAG | AATGGCCCAC | CCCAGGAGGG | TGATGAGGGC | 6000
| GAGGCGGCTG | GTGGCGAAGA | TGGTGCTGAA | GGCGGTGAGG | GTGAAGGCGG | CAGCGGCGGC | 6060
| GGCGGCGATG | ATGATGGTGG | CTCAGCGACG | GCGGCGGGAG | CCACATCACC | CACAGATCCA | 6120
| GATGCCGGCG | AAGCAGATGG | TGCCAGCGCC | GGCAATGGTG | GCGGCCCCCT | TAGTCCGGGC | 6180
| TGTGTTAGTG | GCGGCAGTAA | TGGCCGCCAA | ACGGCCGTAC | TGGTCGAAAG | CGATGGTTTT | 6240
| GTTACAAAAA | ACGGTCATAA | GGTTGTAATA | CACTCGAGAT | CGCCGAGCAT | AACATCCAGG | 6300
| ACGGCAGATG | TCTGA | | | | | 6315

( 2 ) INFORMATION FOR SEQ ID NO:3:

( i ) SEQUENCE CHARACTERISTICS:
        ( A ) LENGTH: 2105 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:3:

Met Thr Glu Asp Ser Asp Ser Ile Ser Glu Glu Glu Arg Ser Leu Phe
 1          5              10            15

| | | | | | | | | | | | | | | |
|---|---|---|---|---|---|---|---|---|---|---|---|---|---|---|
|Arg|Pro|Phe|Thr|Arg|Glu|Ser|Leu|Leu|Gln|Ile|Glu|Gln|Arg|Ile|Ala|
| | | | |20| | |25| | | |30| | | |
|Glu|His|Glu|Lys|Gln|Lys|Glu|Leu|Glu|Arg|Lys|Arg|Ala|Ala|Glu|Gly|
| | |35| | | |40| | | |45| | | | |
|Glu|Gln|Ile|Arg|Tyr|Asp|Asp|Glu|Asp|Glu|Asp|Gly|Pro|Gln|Pro|
| |50| | | |55| | | |60| | | | |
|Asp|Pro|Thr|Leu|Glu|Gln|Gly|Val|Pro|Ile|Pro|Val|Arg|Met|Gln|Gly|
|65| | | | |70| | | |75| | | | |80|
|Ser|Phe|Pro|Pro|Glu|Leu|Ala|Ser|Thr|Pro|Leu|Glu|Asp|Ile|Asp|Pro|
| | | | |85| | | |90| | | | |95|
|Phe|Tyr|Ser|Asn|Val|Leu|Thr|Phe|Val|Ile|Ser|Lys|Gly|Lys|Asp|
| | | |100| | |105| | | |110| | | |
|Ile|Phe|Arg|Phe|Ser|Ala|Ser|Lys|Ala|Met|Trp|Leu|Leu|Asp|Pro|Phe|
| | |115| | | |120| | | |125| | | |
|Asn|Pro|Ile|Arg|Arg|Val|Ala|Ile|Tyr|Ile|Leu|Val|His|Pro|Leu|Phe|
| |130| | | | |135| | | |140| | | |
|Ser|Leu|Phe|Ile|Ile|Thr|Thr|Ile|Leu|Thr|Asn|Cys|Ile|Leu|Met|Ile|
|145| | | | |150| | | |155| | | |160|
|Met|Pro|Thr|Thr|Pro|Thr|Val|Glu|Ser|Thr|Glu|Val|Ile|Phe|Thr|Gly|
| | | | |165| | | |170| | | |175| |
|Ile|Tyr|Thr|Phe|Glu|Ser|Ala|Val|Lys|Val|Met|Ala|Arg|Gly|Phe|Ile|
| | | |180| | | |185| | | |190| |
|Leu|Cys|Pro|Phe|Thr|Tyr|Leu|Arg|Asp|Ala|Trp|Asn|Trp|Leu|Asp|Phe|
| | |195| | | |200| | | |205| | | |
|Val|Val|Ile|Ala|Leu|Ala|Tyr|Val|Thr|Met|Gly|Ile|Asp|Leu|Gly|Asn|
| |210| | | | |215| | | |220| | | |
|Leu|Ala|Ala|Leu|Arg|Thr|Phe|Arg|Val|Leu|Arg|Ala|Leu|Lys|Thr|Val|
|225| | | | |230| | | |235| | | |240|
|Ala|Ile|Val|Pro|Gly|Leu|Lys|Thr|Ile|Val|Gly|Ala|Val|Ile|Glu|Ser|
| | | |245| | | |250| | | |255| |
|Val|Lys|Asn|Leu|Arg|Asp|Val|Ile|Ile|Leu|Thr|Met|Phe|Ser|Leu|Ser|
| | | |260| | | |265| | | |270| | |
|Val|Phe|Ala|Leu|Met|Gly|Leu|Gln|Ile|Tyr|Met|Gly|Val|Leu|Thr|Gln|
| | |275| | | |280| | | |285| | | |
|Lys|Cys|Ile|Lys|Arg|Phe|Pro|Leu|Asp|Gly|Ser|Trp|Gly|Asn|Leu|Thr|
| |290| | | | |295| | | |300| | | |
|Asp|Glu|Asn|Trp|Phe|Leu|His|Asn|Ser|Asn|Ser|Ser|Asn|Trp|Phe|Thr|
|305| | | | |310| | | |315| | | |320|
|Glu|Asn|Asp|Gly|Glu|Ser|Tyr|Pro|Val|Cys|Gly|Asn|Val|Ser|Gly|Ala|
| | | |325| | | |330| | | |335| |
|Gly|Gln|Cys|Gly|Glu|Asp|Tyr|Val|Cys|Leu|Gln|Gly|Phe|Gly|Pro|Asn|
| | |340| | | |345| | | |350| | |
|Pro|Asn|Tyr|Asp|Tyr|Thr|Ser|Phe|Asp|Ser|Phe|Gly|Trp|Ala|Phe|Leu|
| | |355| | | |360| | | |365| | | |
|Ser|Ala|Phe|Arg|Leu|Met|Thr|Gln|Asp|Phe|Trp|Glu|Asp|Leu|Tyr|Gln|
| |370| | | | |375| | | |380| | | |
|His|Val|Leu|Gln|Ala|Ala|Gly|Pro|Trp|His|Met|Leu|Phe|Phe|Ile|Val|
|385| | | | |390| | | |395| | | |400|
|Ile|Ile|Phe|Leu|Gly|Ser|Phe|Tyr|Leu|Val|Asn|Leu|Ile|Leu|Ala|Ile|
| | | |405| | | |410| | | |415| |
|Val|Ala|Met|Ser|Tyr|Asp|Glu|Leu|Gln|Lys|Lys|Ala|Glu|Glu|Glu|
| | |420| | | |425| | | |430| | | |
|Ala|Ala|Glu|Glu|Glu|Ala|Ile|Arg|Glu|Ala|Glu|Glu|Ala|Ala|Ala|Ala|

-continued

|   |   |   | 435 |   |   |   | 440 |   |   |   | 445 |   |   |   |
|---|---|---|---|---|---|---|---|---|---|---|---|---|---|---|
| Lys | Ala | Ala | Lys | Leu | Glu | Glu | Arg | Ala | Asn | Val | Ala | Gln | Ala | Ala |
|  | 450 |  |  |  | 455 |  |  |  |  | 460 |  |  |  |  |
| Gln | Asp | Ala | Ala | Asp | Ala | Ala | Ala | Ala | Leu | His | Pro | Glu | Met | Ala |
| 465 |  |  |  | 470 |  |  |  |  | 475 |  |  |  |  | 480 |
| Lys | Ser | Pro | Thr | Tyr | Ser | Cys | Ile | Ser | Tyr | Glu | Leu | Phe | Val | Gly | Gly |
|  |  |  |  | 485 |  |  |  |  | 490 |  |  |  |  | 495 |
| Glu | Lys | Gly | Asn | Asp | Asp | Asn | Asn | Lys | Glu | Lys | Met | Ser | Ile | Arg | Ser |
|  |  |  |  | 500 |  |  |  | 505 |  |  |  |  | 510 |  |
| Val | Glu | Val | Glu | Ser | Glu | Ser | Val | Ser | Val | Ile | Gln | Arg | Gln | Pro | Ala |
|  |  | 515 |  |  |  |  | 520 |  |  |  |  | 525 |  |  |
| Pro | Thr | Thr | Ala | Pro | Ala | Thr | Lys | Val | Arg | Lys | Val | Ser | Thr | Thr | Ser |
|  | 530 |  |  |  |  | 535 |  |  |  |  | 540 |  |  |  |
| Leu | Ser | Leu | Pro | Gly | Ser | Pro | Phe | Asn | Leu | Arg | Arg | Gly | Ser | Arg | Ser |
| 545 |  |  |  |  | 550 |  |  |  |  | 555 |  |  |  | 560 |
| Ser | His | Lys | Tyr | Thr | Ile | Arg | Asn | Gly | Arg | Gly | Arg | Phe | Gly | Ile | Pro |
|  |  |  |  | 565 |  |  |  |  | 570 |  |  |  |  | 575 |
| Gly | Ser | Asp | Arg | Lys | Pro | Leu | Val | Leu | Gln | Thr | Tyr | Gln | Asp | Ala | Gln |
|  |  |  | 580 |  |  |  |  | 585 |  |  |  |  | 590 |  |
| Gln | His | Leu | Pro | Tyr | Ala | Asp | Asp | Ser | Asn | Ala | Val | Thr | Pro | Met | Ser |
|  |  | 595 |  |  |  |  | 600 |  |  |  |  | 605 |  |  |
| Glu | Glu | Asn | Gly | Ala | Ile | Ile | Val | Pro | Ala | Tyr | Tyr | Cys | Asn | Leu | Gly |
|  | 610 |  |  |  |  | 615 |  |  |  |  | 620 |  |  |  |
| Ser | Arg | His | Ser | Ser | Tyr | Thr | Ser | His | Gln | Ser | Arg | Ile | Ser | Tyr | Thr |
| 625 |  |  |  |  | 630 |  |  |  |  | 635 |  |  |  |  | 640 |
| Ser | His | Gly | Asp | Leu | Leu | Gly | Gly | Met | Ala | Ala | Met | Gly | Ala | Ser | Thr |
|  |  |  |  | 645 |  |  |  |  | 650 |  |  |  |  | 655 |
| Met | Thr | Lys | Glu | Ser | Lys | Leu | Arg | Ser | Arg | Asn | Thr | Arg | Asn | Gln | Ser |
|  |  |  | 660 |  |  |  |  | 665 |  |  |  |  | 670 |  |
| Ile | Gly | Ala | Ala | Thr | Asn | Gly | Gly | Ser | Ser | Thr | Ala | Gly | Gly | Gly | Tyr |
|  |  |  | 675 |  |  |  | 680 |  |  |  |  | 685 |  |  |
| Pro | Asp | Ala | Asn | His | Lys | Glu | Gln | Arg | Asp | Tyr | Glu | Met | Gly | Gln | Asp |
|  | 690 |  |  |  |  | 695 |  |  |  |  | 700 |  |  |  |
| Tyr | Thr | Asp | Glu | Ala | Gly | Lys | Ile | Lys | His | His | Asp | Asn | Pro | Phe | Ile |
| 705 |  |  |  |  | 710 |  |  |  |  | 715 |  |  |  |  | 720 |
| Glu | Pro | Val | Gln | Thr | Gln | Thr | Val | Val | Asp | Met | Lys | Asp | Val | Met | Val |
|  |  |  |  | 725 |  |  |  |  | 730 |  |  |  |  | 735 |
| Leu | Asn | Asp | Ile | Ile | Glu | Gln | Ala | Ala | Gly | Arg | His | Ser | Arg | Ala | Ser |
|  |  |  | 740 |  |  |  |  | 745 |  |  |  |  | 750 |  |
| Glu | Arg | Gly | Glu | Asp | Asp | Asp | Glu | Asp | Gly | Pro | Thr | Phe | Lys | Asp | Ile |
|  |  | 755 |  |  |  |  | 760 |  |  |  |  | 765 |  |  |
| Ala | Leu | Glu | Tyr | Ile | Leu | Lys | Gly | Ile | Glu | Ile | Phe | Cys | Val | Trp | Asp |
|  | 770 |  |  |  |  | 775 |  |  |  |  | 780 |  |  |  |
| Cys | Cys | Trp | Val | Trp | Leu | Lys | Phe | Gln | Glu | Trp | Val | Ser | Phe | Ile | Val |
| 785 |  |  |  |  | 790 |  |  |  |  | 795 |  |  |  |  | 800 |
| Phe | Asp | Pro | Phe | Val | Glu | Leu | Phe | Ile | Thr | Leu | Cys | Ile | Val | Val | Asn |
|  |  |  |  | 805 |  |  |  |  | 810 |  |  |  |  | 815 |
| Thr | Met | Phe | Met | Ala | Met | Asp | His | His | Asp | Met | Asn | Pro | Glu | Leu | Glu |
|  |  |  | 820 |  |  |  |  | 825 |  |  |  |  | 830 |  |
| Lys | Val | Leu | Lys | Ser | Gly | Asn | Tyr | Phe | Phe | Thr | Ala | Thr | Phe | Ala | Ile |
|  |  |  | 835 |  |  |  |  | 840 |  |  |  |  | 845 |  |
| Glu | Ala | Ser | Met | Lys | Leu | Met | Ala | Met | Ser | Pro | Lys | Tyr | Tyr | Phe | Gln |
| 850 |  |  |  |  | 855 |  |  |  |  | 860 |  |  |  |  |

```
Glu  Gly  Trp  Asn  Ile  Phe  Asp  Phe  Ile  Ile  Val  Ala  Leu  Ser  Leu  Leu
865                      870                 875                          880

Glu  Leu  Gly  Leu  Glu  Gly  Val  Gln  Gly  Leu  Ser  Val  Leu  Arg  Ser  Phe
                    885                 890                      895

Arg  Leu  Leu  Arg  Val  Phe  Lys  Leu  Lys  Ser  Trp  Pro  Thr  Leu  Asn
               900                 905                      910

Leu  Leu  Ile  Ser  Ile  Met  Gly  Arg  Thr  Met  Gly  Ala  Leu  Gly  Asn  Leu
               915                 920                      925

Thr  Phe  Val  Leu  Cys  Ile  Ile  Phe  Ile  Phe  Ala  Val  Met  Gly  Met
          930                 935                 940

Gln  Leu  Phe  Gly  Lys  Asn  Tyr  Ile  Asp  His  Lys  Asp  Arg  Phe  Lys  Asp
945                      950                 955                          960

His  Glu  Leu  Pro  Arg  Trp  Asn  Phe  Thr  Asp  Phe  Met  His  Ser  Phe  Met
                    965                 970                      975

Ile  Val  Phe  Arg  Val  Leu  Cys  Gly  Glu  Trp  Ile  Glu  Ser  Met  Trp  Asp
               980                 985                      990

Cys  Met  Tyr  Val  Gly  Asp  Val  Ser  Cys  Ile  Pro  Phe  Phe  Leu  Ala  Thr
          995                 1000                1005

Val  Val  Ile  Gly  Asn  Leu  Val  Val  Leu  Asn  Leu  Phe  Leu  Ala  Leu  Leu
     1010                1015                1020

Leu  Ser  Asn  Phe  Gly  Ser  Ser  Leu  Ser  Ala  Pro  Thr  Ala  Asp  Asn
1025                     1030                1035                     1040

Asp  Thr  Asn  Lys  Ile  Ala  Glu  Ala  Phe  Asn  Arg  Ile  Ala  Arg  Phe  Lys
                    1045                1050                     1055

Asn  Trp  Val  Lys  Arg  Asn  Ile  Ala  Asp  Cys  Phe  Lys  Leu  Ile  Arg  Asn
                    1060                1065                     1070

Lys  Leu  Thr  Asn  Gln  Ile  Ser  Asp  Gln  Pro  Ser  Glu  His  Gly  Asp  Asn
               1075                1080                     1085

Glu  Leu  Glu  Leu  Gly  His  Asp  Glu  Ile  Met  Gly  Asp  Gly  Leu  Ile  Lys
               1090                1095                     1100

Lys  Gly  Met  Lys  Gly  Glu  Thr  Gln  Leu  Glu  Val  Ala  Ile  Gly  Asp  Gly
1105                     1110                1115                          1120

Met  Glu  Phe  Thr  Ile  His  Gly  Asp  Met  Lys  Asn  Asn  Lys  Pro  Lys  Lys
                    1125                1130                     1135

Ser  Lys  Phe  Met  Asn  Asn  Thr  Thr  Met  Ile  Gly  Asn  Ser  Ile  Asn  His
                    1140                1145                     1150

Gln  Asp  Asn  Arg  Leu  Glu  His  Glu  Leu  Asn  His  Arg  Gly  Leu  Ser  Ile
               1155                1160                     1165

Gln  Asp  Asp  Asp  Thr  Ala  Ser  Ile  Asn  Ser  Tyr  Gly  Ser  His  Lys  Asn
               1170                1175                     1180

Arg  Pro  Phe  Lys  Asp  Glu  Ser  His  Lys  Gly  Ser  Ala  Glu  Thr  Ile  Glu
1185                     1190                1195                          1200

Gly  Glu  Glu  Lys  Arg  Asp  Val  Ser  Lys  Glu  Asp  Leu  Gly  Leu  Asp  Glu
                    1205                1210                     1215

Glu  Leu  Asp  Glu  Glu  Ala  Glu  Gly  Asp  Glu  Gly  Gln  Leu  Asp  Gly  Asp
               1220                1225                     1230

Ile  Ile  Ile  His  Ala  Gln  Asn  Asp  Asp  Glu  Ile  Ile  Asp  Asp  Tyr  Pro
               1235                1240                     1245

Ala  Asp  Cys  Phe  Pro  Asp  Ser  Tyr  Tyr  Lys  Lys  Phe  Pro  Ile  Leu  Ala
     1250                     1255                     1260

Gly  Asp  Glu  Asp  Ser  Pro  Phe  Trp  Gln  Gly  Trp  Gly  Asn  Leu  Arg  Leu
1265                     1270                1275                          1280

Lys  Thr  Phe  Gln  Leu  Ile  Glu  Asn  Lys  Tyr  Phe  Glu  Thr  Ala  Val  Ile
                    1285                1290                     1295
```

Thr Met Ile Leu Met Ser Ser Leu Ala Leu Ala Leu Glu Asp Val His
              1300                1305                1310

Leu Pro Asp Arg Pro Val Met Gln Asp Ile Leu Tyr Tyr Met Asp Arg
              1315                1320                1325

Ile Phe Thr Val Ile Phe Phe Leu Glu Met Leu Ile Lys Trp Leu Ala
              1330                1335                1340

Leu Gly Phe Lys Val Tyr Phe Thr Asn Ala Trp Cys Trp Leu Asp Phe
1345                1350                1355                1360

Val Ile Val Met Leu Ser Leu Ile Asn Leu Val Ala Val Trp Ser Gly
              1365                1370                1375

Leu Asn Asp Ile Ala Val Phe Arg Ser Met Arg Thr Leu Arg Ala Leu
              1380                1385                1390

Arg Pro Leu Arg Ala Val Ser Arg Trp Glu Gly Met Lys Val Val Val
              1395                1400                1405

Asn Ala Leu Val Gln Ala Ile Pro Ser Ile Phe Asn Val Leu Leu Val
              1410                1415                1420

Cys Leu Ile Phe Trp Leu Ile Phe Ala Ile Met Gly Val Gln Leu Phe
1425                1430                1435                1440

Ala Gly Lys Tyr Phe Lys Cys Lys Asp Gly Asn Asp Thr Val Leu Ser
              1445                1450                1455

His Glu Ile Ile Pro Asn Arg Asn Ala Cys Lys Ser Glu Gly Asn Tyr Thr
              1460                1465                1470

Trp Glu Asn Ser Ala Met Asn Phe Asp His Val Gly Asn Ala Tyr Leu
              1475                1480                1485

Cys Leu Phe Gln Val Ala Thr Phe Lys Gly Trp Ile Gln Ile Met Asn
              1490                1495                1500

Asp Ala Ile Asp Ser Arg Glu Val Asp Lys Gln Pro Ile Arg Glu Thr
1505                1510                1515                1520

Asn Ile Tyr Met Tyr Leu Tyr Phe Val Phe Phe Ile Ile Phe Gly Ser
              1525                1530                1535

Phe Phe Thr Leu Asn Leu Phe Ile Gly Val Ile Ile Asp Asn Phe Asn
              1540                1545                1550

Glu Gln Lys Lys Lys Ala Gly Gly Ser Leu Glu Met Phe Met Thr Glu
              1555                1560                1565

Asp Gln Lys Lys Tyr Tyr Asn Ala Met Lys Lys Met Gly Ser Lys Lys
              1570                1575                1580

Pro Leu Lys Ala Ile Pro Arg Pro Arg Trp Arg Pro Gln Ala Ile Val
1585                1590                1595                1600

Phe Glu Ile Val Thr Asp Lys Lys Phe Asp Ile Ile Ile Met Leu Phe
              1605                1610                1615

Ile Gly Leu Asn Met Phe Thr Met Thr Leu Asp Arg Tyr Asp Ala Ser
              1620                1625                1630

Glu Ala Tyr Asn Asn Val Leu Asp Lys Leu Asn Gly Ile Phe Val Val
              1635                1640                1645

Ile Phe Ser Gly Glu Cys Leu Leu Lys Ile Phe Ala Leu Arg Tyr His
              1650                1655                1660

Tyr Phe Lys Glu Pro Trp Asn Leu Phe Asp Val Val Val Val Ile Leu
1665                1670                1675                1680

Ser Ile Leu Gly Leu Val Leu Ser Asp Ile Ile Glu Lys Tyr Phe Val
              1685                1690                1695

Ser Pro Thr Leu Leu Arg Val Val Arg Val Ala Lys Val Gly Arg Val
              1700                1705                1710

Leu Arg Leu Val Lys Gly Ala Lys Gly Ile Arg Thr Leu Leu Phe Ala

```
                         1715                      1720                           1725
    Leu  Ala  Met  Ser  Leu  Pro  Ala  Leu  Phe  Asn  Ile  Cys  Leu  Leu  Leu  Phe
              1730                     1735                1740
    Leu  Val  Met  Phe  Ile  Phe  Ala  Ile  Phe  Gly  Met  Ser  Phe  Phe  Met  His
    1745                     1750                     1755                     1760
    Val  Lys  Glu  Lys  Ser  Gly  Ile  Asn  Ala  Val  Tyr  Asn  Phe  Lys  Thr  Phe
                        1765                     1770                     1775
    Gly  Gln  Ser  Met  Ile  Leu  Leu  Phe  Gln  Met  Ser  Thr  Ser  Ala  Gly  Trp
                   1780                     1785                     1790
    Asp  Gly  Val  Leu  Asp  Ala  Ile  Ile  Asn  Glu  Glu  Asp  Cys  Asp  Pro  Pro
                   1795                     1800                     1805
    Asp  Asn  Asp  Lys  Gly  Tyr  Pro  Gly  Asn  Cys  Gly  Ser  Ala  Thr  Val  Gly
              1810                     1815                     1820
    Ile  Thr  Phe  Leu  Leu  Ser  Tyr  Leu  Val  Ile  Ser  Phe  Leu  Ile  Val  Ile
    1825                     1830                     1835                     1840
    Asn  Met  Tyr  Ile  Ala  Val  Ile  Leu  Glu  Asn  Tyr  Ser  Gln  Ala  Thr  Glu
                        1845                     1850                     1855
    Asp  Val  Gln  Glu  Gly  Leu  Thr  Asp  Asp  Tyr  Asp  Met  Tyr  Tyr  Glu
                   1860                     1865                     1870
    Ile  Trp  Gln  Gln  Phe  Asp  Pro  Glu  Gly  Thr  Gln  Tyr  Ile  Arg  Tyr  Asp
              1875                     1880                     1885
    Gln  Leu  Ser  Glu  Phe  Leu  Asp  Val  Leu  Glu  Pro  Pro  Leu  Gln  Ile  His
         1890                     1895                     1900
    Lys  Pro  Asn  Lys  Tyr  Lys  Ile  Ile  Ser  Met  Asp  Met  Pro  Ile  Cys  Arg
    1905                     1910                     1915                     1920
    Gly  Asp  Met  Met  Tyr  Cys  Val  Asp  Ile  Leu  Asp  Ala  Leu  Thr  Lys  Asp
                        1925                     1930                     1935
    Phe  Phe  Ala  Arg  Lys  Gly  Asn  Pro  Ile  Glu  Glu  Thr  Gly  Glu  Ile  Gly
                   1940                     1945                     1950
    Glu  Ile  Ala  Ala  Arg  Pro  Asp  Thr  Glu  Gly  Tyr  Asp  Pro  Val  Ser  Ser
                   1955                     1960                     1965
    Thr  Leu  Trp  Arg  Gln  Arg  Glu  Glu  Tyr  Cys  Ala  Lys  Leu  Ile  Gln  Asn
         1970                     1975                     1980
    Ala  Trp  Arg  Arg  Tyr  Lys  Asn  Gly  Pro  Pro  Gln  Glu  Gly  Asp  Glu  Gly
    1985                     1990                     1995                     2000
    Glu  Ala  Ala  Gly  Gly  Glu  Asp  Gly  Ala  Glu  Gly  Glu  Gly  Glu  Gly
                        2005                     2010                     2015
    Gly  Ser  Gly  Gly  Gly  Gly  Gly  Asp  Asp  Gly  Gly  Ser  Ala  Thr  Gly  Ala
                   2020                     2025                     2030
    Thr  Ala  Ala  Ala  Gly  Ala  Thr  Ser  Pro  Ser  Asp  Pro  Asp  Ala  Gly  Glu
              2035                     2040                     2045
    Ala  Asp  Gly  Ala  Ser  Val  Gly  Gly  Pro  Leu  Ser  Pro  Gly  Cys  Val  Ser
              2050                     2055                     2060
    Gly  Gly  Ser  Asn  Gly  Arg  Gln  Thr  Ala  Val  Leu  Val  Glu  Ser  Asp  Gly
    2065                     2070                     2075                     2080
    Phe  Val  Thr  Lys  Asn  Gly  His  Lys  Val  Val  Ile  His  Ser  Arg  Ser  Pro
                        2085                     2090                     2095
    Ser  Ile  Thr  Ser  Arg  Thr  Ala  Asp  Val
                   2100                     2105
```

( 2 ) INFORMATION FOR SEQ ID NO:4:

( i ) SEQUENCE CHARACTERISTICS:
        ( A ) LENGTH: 2104 amino acids
        ( B ) TYPE: amino acid ( C ) STRANDEDNESS: Not Relevant
( D ) TOPOLOGY: linear ( i i ) MOLECULE TYPE: protein ( x i ) SEQUENCE DESCRIPTION: SEQ ID NO:4:

```
Met  Thr  Glu  Asp  Ser  Asp  Ser  Ile  Ser  Glu  Glu  Arg  Ser  Leu  Phe
 1              5                   10                       15

Arg  Pro  Phe  Thr  Arg  Glu  Ser  Leu  Leu  Gln  Ile  Glu  Gln  Arg  Ile  Ala
              20                   25                       30

Glu  His  Glu  Lys  Gln  Lys  Glu  Leu  Glu  Arg  Lys  Arg  Ala  Ala  Glu  Gly
              35                   40                       45

Glu  Gln  Ile  Arg  Tyr  Asp  Asp  Glu  Asp  Glu  Asp  Glu  Gly  Pro  Gln  Pro
         50                       55                       60

Asp  Pro  Thr  Leu  Glu  Gln  Gly  Val  Pro  Ile  Pro  Val  Arg  Met  Gln  Gly
 65                       70                       75                       80

Ser  Phe  Pro  Pro  Glu  Leu  Ala  Ser  Thr  Pro  Leu  Glu  Asp  Ile  Asp  Pro
                   85                       90                       95

Phe  Tyr  Ser  Asn  Val  Leu  Thr  Phe  Val  Val  Ile  Ser  Lys  Gly  Lys  Asp
              100                  105                      110

Ile  Phe  Arg  Phe  Ser  Ala  Ser  Lys  Ala  Met  Trp  Leu  Leu  Asp  Pro  Phe
              115                  120                      125

Asn  Pro  Ile  Arg  Arg  Val  Ala  Ile  Tyr  Ile  Leu  Val  His  Pro  Leu  Phe
     130                      135                      140

Ser  Leu  Phe  Ile  Ile  Thr  Thr  Ile  Leu  Thr  Asn  Cys  Ile  Leu  Met  Ile
145                      150                      155                      160

Met  Pro  Thr  Thr  Pro  Thr  Val  Glu  Ser  Thr  Glu  Val  Ile  Phe  Thr  Gly
                   165                      170                      175

Ile  Tyr  Thr  Phe  Glu  Ser  Ala  Val  Lys  Val  Met  Ala  Arg  Gly  Phe  Ile
              180                      185                      190

Leu  Cys  Pro  Phe  Thr  Tyr  Leu  Arg  Asp  Ala  Trp  Asn  Trp  Leu  Asp  Phe
         195                      200                      205

Val  Val  Ile  Ala  Leu  Ala  Tyr  Val  Thr  Met  Gly  Ile  Asp  Leu  Gly  Asn
     210                      215                      220

Leu  Ala  Ala  Leu  Arg  Thr  Phe  Arg  Val  Leu  Arg  Ala  Leu  Lys  Thr  Val
225                      230                      235                      240

Ala  Ile  Val  Pro  Gly  Leu  Lys  Thr  Ile  Val  Gly  Ala  Val  Ile  Glu  Ser
                   245                      250                      255

Val  Lys  Asn  Leu  Arg  Asp  Val  Ile  Ile  Leu  Thr  Met  Phe  Ser  Leu  Ser
              260                      265                      270

Val  Phe  Ala  Leu  Met  Gly  Leu  Gln  Ile  Tyr  Met  Gly  Val  Leu  Thr  Gln
         275                      280                      285

Lys  Cys  Ile  Lys  Arg  Phe  Pro  Leu  Asp  Gly  Ser  Trp  Gly  Asn  Leu  Thr
     290                      295                      300

Asp  Glu  Asn  Trp  Phe  Leu  His  Asn  Ser  Asn  Ser  Ser  Asn  Trp  Phe  Thr
305                      310                      315                      320

Glu  Asn  Asp  Gly  Glu  Ser  Tyr  Pro  Val  Cys  Gly  Asn  Val  Ser  Gly  Ala
                   325                      330                      335

Gly  Gln  Cys  Gly  Glu  Asp  Tyr  Val  Cys  Leu  Gln  Gly  Phe  Gly  Pro  Asn
              340                      345                      350

Pro  Asn  Tyr  Asp  Tyr  Thr  Ser  Phe  Asp  Ser  Phe  Gly  Trp  Ala  Phe  Leu
         355                      360                      365

Ser  Ala  Phe  Arg  Leu  Met  Thr  Gln  Asp  Phe  Trp  Glu  Asp  Leu  Tyr  Gln
     370                      375                      380

His  Val  Leu  Gln  Ala  Ala  Gly  Pro  Trp  His  Met  Leu  Phe  Phe  Ile  Val
```

-continued

```
          385                      390                      395                      400
     Ile  Ile  Phe  Leu  Gly  Ser  Phe  Tyr  Leu  Val  Asn  Leu  Ile  Leu  Ala  Ile
                         405                      410                      415
     Val  Ala  Met  Ser  Tyr  Asp  Glu  Leu  Gln  Lys  Lys  Ala  Glu  Glu  Glu  Glu
                    420                      425                      430
     Ala  Ala  Glu  Glu  Glu  Ala  Ile  Arg  Glu  Ala  Glu  Glu  Ala  Ala  Ala  Ala
                    435                      440                      445
     Lys  Ala  Ala  Lys  Leu  Glu  Glu  Arg  Ala  Asn  Val  Ala  Ala  Gln  Ala  Ala
               450                      455                      460
     Gln  Asp  Ala  Ala  Asp  Ala  Ala  Ala  Ala  Ala  Leu  His  Pro  Glu  Met  Ala
     465                      470                      475                      480
     Lys  Ser  Pro  Thr  Tyr  Ser  Cys  Ile  Ser  Tyr  Glu  Leu  Phe  Val  Gly  Gly
                         485                      490                      495
     Glu  Lys  Gly  Asn  Asp  Asp  Asn  Asn  Lys  Glu  Lys  Met  Ser  Ile  Arg  Ser
                    500                      505                      510
     Val  Glu  Val  Glu  Ser  Glu  Ser  Val  Ser  Val  Ile  Gln  Arg  Gln  Pro  Ala
                    515                      520                      525
     Pro  Thr  Thr  Ala  Pro  Ala  Thr  Lys  Val  Arg  Lys  Val  Ser  Thr  Thr  Ser
          530                      535                      540
     Leu  Ser  Leu  Pro  Gly  Ser  Pro  Phe  Asn  Leu  Arg  Arg  Gly  Ser  Arg  Ser
     545                      550                      555                      560
     Ser  His  Lys  Tyr  Thr  Ile  Arg  Asn  Gly  Arg  Gly  Arg  Phe  Gly  Ile  Pro
                         565                      570                      575
     Gly  Ser  Asp  Arg  Lys  Pro  Leu  Val  Leu  Gln  Thr  Tyr  Gln  Asp  Ala  Gln
                    580                      585                      590
     Gln  His  Leu  Pro  Tyr  Ala  Asp  Asp  Ser  Asn  Ala  Val  Thr  Pro  Met  Ser
                    595                      600                      605
     Glu  Glu  Asn  Gly  Ala  Ile  Ile  Val  Pro  Ala  Tyr  Tyr  Cys  Asn  Leu  Gly
          610                      615                      620
     Ser  Arg  His  Ser  Ser  Tyr  Thr  Ser  His  Gln  Ser  Arg  Ile  Ser  Tyr  Thr
     625                      630                      635                      640
     Ser  His  Gly  Asp  Leu  Leu  Gly  Gly  Met  Ala  Ala  Met  Gly  Ala  Ser  Thr
                         645                      650                      655
     Met  Thr  Lys  Glu  Ser  Lys  Leu  Arg  Ser  Arg  Asn  Thr  Arg  Asn  Gln  Ser
                    660                      665                      670
     Ile  Gly  Ala  Ala  Thr  Asn  Gly  Gly  Ser  Ser  Thr  Ala  Gly  Gly  Gly  Tyr
                    675                      680                      685
     Pro  Asp  Ala  Asn  His  Lys  Glu  Gln  Arg  Asp  Tyr  Glu  Met  Gly  Gln  Asp
          690                      695                      700
     Tyr  Thr  Asp  Glu  Ala  Gly  Lys  Ile  Lys  His  His  Asp  Asn  Pro  Phe  Ile
     705                      710                      715                      720
     Glu  Pro  Val  Gln  Thr  Gln  Thr  Val  Val  Asp  Met  Lys  Asp  Val  Met  Val
                         725                      730                      735
     Leu  Asn  Asp  Ile  Ile  Glu  Gln  Ala  Ala  Gly  Arg  His  Ser  Arg  Ala  Ser
                    740                      745                      750
     Glu  Arg  Gly  Glu  Asp  Asp  Asp  Glu  Asp  Gly  Pro  Thr  Phe  Lys  Asp  Ile
                    755                      760                      765
     Ala  Leu  Glu  Tyr  Ile  Leu  Lys  Gly  Ile  Glu  Ile  Phe  Cys  Val  Trp  Asp
          770                      775                      780
     Cys  Cys  Trp  Val  Trp  Leu  Lys  Phe  Gln  Glu  Trp  Val  Ser  Phe  Ile  Val
     785                      790                      795                      800
     Phe  Asp  Pro  Phe  Val  Glu  Leu  Phe  Ile  Thr  Leu  Cys  Ile  Val  Val  Asn
                         805                      810                      815
```

```
Thr  Met  Phe  Met  Ala  Met  Asp  His  His  Asp  Met  Asn  Pro  Glu  Leu  Glu
               820                 825                 830

Lys  Val  Leu  Lys  Ser  Gly  Asn  Tyr  Phe  Thr  Ala  Thr  Phe  Ala  Ile
          835                 840                 845

Glu  Ala  Ser  Met  Lys  Leu  Ala  Met  Ser  Pro  Lys  Tyr  Tyr  Phe  Gln
     850                      855                 860

Glu  Gly  Trp  Asn  Ile  Phe  Asp  Phe  Ile  Ile  Val  Ala  Leu  Ser  Leu  Leu
865                      870                 875                           880

Glu  Leu  Gly  Leu  Glu  Gly  Val  Gln  Gly  Leu  Ser  Val  Leu  Arg  Ser  Phe
                    885                      890                      895

Arg  Leu  Leu  Arg  Val  Phe  Lys  Leu  Ala  Lys  Ser  Trp  Pro  Thr  Leu  Asn
               900                 905                      910

Leu  Leu  Ile  Ser  Ile  Met  Gly  Arg  Thr  Met  Gly  Ala  Leu  Gly  Asn  Leu
               915                 920                      925

Thr  Phe  Val  Leu  Cys  Ile  Ile  Ile  Phe  Ile  Phe  Ala  Val  Met  Gly  Met
          930                 935                      940

Gln  Leu  Phe  Gly  Lys  Asn  Tyr  Ile  Asp  His  Lys  Asp  Arg  Phe  Lys  Asp
945                      950                 955                           960

His  Glu  Leu  Pro  Arg  Trp  Asn  Phe  Thr  Asp  Phe  Met  His  Ser  Phe  Met
                    965                 970                      975

Ile  Val  Phe  Arg  Val  Leu  Cys  Gly  Glu  Trp  Ile  Glu  Ser  Met  Trp  Asp
               980                 985                      990

Cys  Met  Tyr  Val  Gly  Asp  Val  Ser  Cys  Ile  Pro  Phe  Phe  Leu  Ala  Thr
          995                 1000                1005

Val  Val  Ile  Gly  Asn  Phe  Val  Val  Leu  Asn  Leu  Phe  Leu  Ala  Leu  Leu
          1010                1015                1020

Leu  Ser  Asn  Phe  Gly  Ser  Ser  Ser  Leu  Ser  Ala  Pro  Thr  Ala  Asp  Asn
1025                     1030                1035                          1040

Asp  Thr  Asn  Lys  Ile  Ala  Glu  Ala  Phe  Asn  Arg  Ile  Ala  Arg  Phe  Lys
                    1045                1050                     1055

Asn  Trp  Val  Lys  Arg  Asn  Ile  Ala  Asp  Cys  Phe  Lys  Leu  Ile  Arg  Asn
                    1060                1065                     1070

Lys  Leu  Thr  Asn  Gln  Ile  Ser  Asp  Gln  Pro  Ser  Glu  His  Gly  Asp  Asn
                    1075                1080                     1085

Glu  Leu  Glu  Leu  Gly  His  Asp  Glu  Ile  Met  Gly  Asp  Gly  Leu  Ile  Lys
          1090                1095                1100

Lys  Gly  Met  Lys  Gly  Glu  Thr  Gln  Leu  Glu  Val  Ala  Ile  Gly  Asp  Gly
1105                     1110                1115                          1120

Met  Glu  Phe  Thr  Ile  His  Gly  Asp  Met  Lys  Asn  Asn  Lys  Pro  Lys  Lys
                    1125                1130                     1135

Ser  Lys  Phe  Ile  Asn  Asn  Thr  Thr  Met  Ile  Gly  Asn  Ser  Ile  Asn  His
                    1140                1145                     1150

Gln  Asp  Asn  Arg  Leu  Glu  His  Glu  Leu  Asn  His  Arg  Gly  Leu  Ser  Ile
                    1155                1160                     1165

Gln  Asp  Asp  Asp  Thr  Ala  Ser  Ile  Asn  Ser  Tyr  Gly  Ser  His  Lys  Asn
                    1170                1175                     1180

Arg  Pro  Phe  Lys  Asp  Glu  Ser  His  Lys  Gly  Ser  Ala  Glu  Thr  Ile  Glu
1185                     1190                1195                          1200

Gly  Glu  Glu  Lys  Arg  Asp  Val  Ser  Lys  Glu  Asp  Leu  Gly  Leu  Asp  Glu
                    1205                1210                     1215

Glu  Leu  Asp  Glu  Glu  Ala  Glu  Gly  Asp  Glu  Gly  Gln  Leu  Asp  Gly  Asp
                    1220                1225                     1230

Ile  Ile  Ile  His  Ala  Gln  Asn  Asp  Asp  Glu  Ile  Ile  Asp  Asp  Tyr  Pro
                    1235                1240                     1245
```

Ala Asp Cys Phe Pro Asp Ser Tyr Tyr Lys Lys Phe Pro Ile Leu Ala
1250                     1255                    1260

Gly Asp Glu Asp Ser Pro Phe Trp Gln Gly Trp Gly Asn Leu Arg Leu
1265                    1270                    1275                    1280

Lys Thr Phe Gln Leu Ile Glu Asn Lys Tyr Phe Glu Thr Ala Val Ile
                    1285                    1290                    1295

Thr Met Ile Leu Met Ser Ser Leu Ala Leu Ala Leu Glu Asp Val His
            1300                    1305                    1310

Leu Pro Asp Arg Pro Val Met Gln Asp Ile Leu Tyr Tyr Met Asp Arg
            1315                    1320                    1325

Ile Phe Thr Val Ile Phe Phe Leu Glu Met Leu Ile Lys Trp Leu Ala
            1330                    1335                    1340

Leu Gly Phe Lys Val Tyr Phe Thr Asn Ala Trp Cys Trp Leu Asp Phe
1345                    1350                    1355                    1360

Val Ile Val Met Leu Ser Leu Ile Asn Leu Val Ala Val Trp Ser Gly
                    1365                    1370                    1375

Leu Asn Asp Ile Ala Val Phe Arg Ser Met Arg Thr Leu Arg Ala Leu
            1380                    1385                    1390

Arg Pro Leu Arg Ala Val Ser Arg Trp Glu Gly Met Lys Val Val Val
            1395                    1400                    1405

Asn Ala Leu Val Gln Ala Ile Pro Ser Ile Phe Asn Val Leu Leu Val
1410                    1415                    1420

Cys Leu Ile Phe Trp Leu Ile Phe Ala Ile Met Gly Val Gln Leu Phe
1425                    1430                    1435                    1440

Ala Gly Lys Tyr Phe Lys Cys Lys Asp Gly Asn Asp Thr Val Leu Ser
                    1445                    1450                    1455

His Glu Ile Ile Pro Asn Arg Asn Ala Cys Lys Ser Glu Asn Tyr Thr
            1460                    1465                    1470

Trp Glu Asn Ser Ala Met Asn Phe Asp His Val Gly Asn Ala Tyr Leu
            1475                    1480                    1485

Cys Leu Phe Gln Val Ala Thr Phe Lys Gly Trp Ile Gln Ile Met Asn
1490                    1495                    1500

Asp Ala Ile Asp Ser Arg Glu Val Asp Lys Gln Pro Ile Arg Glu Thr
1505                    1510                    1515                    1520

Asn Ile Tyr Met Tyr Leu Tyr Phe Val Phe Phe Ile Ile Phe Gly Ser
                    1525                    1530                    1535

Phe Phe Thr Leu Asn Leu Phe Ile Gly Val Ile Ile Asp Asn Phe Asn
            1540                    1545                    1550

Glu Gln Lys Lys Lys Ala Gly Gly Ser Leu Glu Met Phe Met Thr Glu
            1555                    1560                    1565

Asp Gln Lys Lys Tyr Tyr Asn Ala Met Lys Lys Met Gly Ser Lys Lys
1570                    1575                    1580

Pro Leu Lys Ala Ile Pro Arg Pro Arg Trp Arg Pro Gln Ala Ile Val
1585                    1590                    1595                    1600

Phe Glu Ile Val Thr Asp Lys Lys Phe Asp Ile Ile Met Leu Phe
            1605                    1610                    1615

Ile Gly Leu Asn Met Phe Thr Met Thr Leu Asp Arg Tyr Asp Ala Ser
            1620                    1625                    1630

Glu Ala Tyr Asn Asn Val Leu Asp Lys Leu Asn Gly Ile Phe Val Val
            1635                    1640                    1645

Ile Phe Ser Gly Glu Cys Leu Leu Lys Ile Phe Ala Leu Arg Tyr His
            1650                    1655                    1660

Tyr Phe Lys Glu Pro Trp Asn Leu Phe Asp Val Val Val Val Ile Leu

```
                1665                    1670                    1675                    1680

Ser  Ile  Leu  Gly  Leu  Val  Leu  Ser  Asp  Ile  Ile  Glu  Lys  Tyr  Phe  Val
                          1685                    1690                    1695

Ser  Pro  Thr  Leu  Leu  Arg  Val  Val  Arg  Val  Ala  Lys  Val  Gly  Arg  Val
                1700                    1705                    1710

Leu  Arg  Leu  Val  Lys  Gly  Ala  Lys  Gly  Ile  Arg  Thr  Leu  Leu  Phe  Ala
                          1715                    1720                    1725

Leu  Ala  Met  Ser  Leu  Pro  Ala  Leu  Phe  Asn  Ile  Cys  Leu  Leu  Leu  Phe
                1730                    1735                    1740

Leu  Val  Met  Phe  Ile  Phe  Ala  Ile  Phe  Gly  Met  Ser  Phe  Phe  Met  His
1745                     1750                    1755                    1760

Val  Lys  Glu  Lys  Ser  Gly  Ile  Asn  Ala  Val  Tyr  Asn  Phe  Lys  Thr  Phe
                          1765                    1770                    1775

Gly  Gln  Ser  Met  Ile  Leu  Leu  Phe  Gln  Met  Ser  Thr  Ser  Ala  Gly  Trp
                1780                    1785                    1790

Asp  Gly  Val  Leu  Asp  Ala  Ile  Ile  Asn  Glu  Glu  Asp  Cys  Asp  Pro  Pro
                          1795                    1800                    1805

Asp  Asn  Asp  Lys  Gly  Tyr  Pro  Gly  Asn  Cys  Gly  Ser  Ala  Thr  Val  Gly
                1810                    1815                    1820

Ile  Thr  Phe  Leu  Leu  Ser  Tyr  Leu  Val  Ile  Ser  Phe  Leu  Ile  Val  Ile
1825                     1830                    1835                    1840

Asn  Met  Tyr  Ile  Ala  Val  Ile  Leu  Glu  Asn  Tyr  Ser  Gln  Ala  Thr  Glu
                          1845                    1850                    1855

Asp  Val  Gln  Glu  Gly  Leu  Thr  Asp  Asp  Tyr  Asp  Met  Tyr  Tyr  Glu
                1860                    1865                    1870

Ile  Trp  Gln  Gln  Phe  Asp  Pro  Glu  Gly  Thr  Gln  Tyr  Ile  Arg  Tyr  Asp
                          1875                    1880                    1885

Gln  Leu  Ser  Glu  Phe  Leu  Asp  Val  Leu  Glu  Pro  Pro  Leu  Gln  Ile  His
                1890                    1895                    1900

Lys  Pro  Asn  Lys  Tyr  Lys  Ile  Ile  Ser  Met  Asp  Met  Pro  Ile  Cys  Arg
1905                     1910                    1915                    1920

Gly  Asp  Met  Met  Tyr  Cys  Val  Asp  Ile  Leu  Asp  Ala  Leu  Thr  Lys  Asp
                          1925                    1930                    1935

Phe  Phe  Ala  Arg  Lys  Gly  Asn  Pro  Ile  Glu  Glu  Thr  Gly  Glu  Ile  Gly
                1940                    1945                    1950

Glu  Ile  Ala  Ala  Arg  Pro  Asp  Thr  Glu  Gly  Tyr  Asp  Pro  Val  Ser  Ser
                1955                    1960                    1965

Thr  Leu  Trp  Arg  Gln  Arg  Glu  Glu  Tyr  Cys  Ala  Lys  Leu  Ile  Gln  Asn
                1970                    1975                    1980

Ala  Trp  Arg  Arg  Tyr  Lys  Asn  Gly  Pro  Pro  Gln  Glu  Gly  Asp  Glu  Gly
1985                     1990                    1995                    2000

Glu  Ala  Ala  Gly  Gly  Glu  Asp  Gly  Ala  Glu  Gly  Gly  Glu  Gly  Glu  Gly
                          2005                    2010                    2015

Gly  Ser  Gly  Gly  Gly  Gly  Asp  Asp  Asp  Gly  Gly  Ser  Ala  Thr  Ala  Ala
                2020                    2025                    2030

Gly  Ala  Thr  Ser  Pro  Thr  Asp  Pro  Asp  Ala  Gly  Glu  Ala  Asp  Gly  Ala
                          2035                    2040                    2045

Ser  Ala  Gly  Asn  Gly  Gly  Gly  Pro  Leu  Ser  Pro  Gly  Cys  Val  Ser  Gly
                2050                    2055                    2060

Gly  Ser  Asn  Gly  Arg  Gln  Thr  Ala  Val  Leu  Val  Glu  Ser  Asp  Gly  Phe
                          2065                    2070                    2075                    2080

Val  Thr  Lys  Asn  Gly  His  Lys  Val  Val  Ile  His  Ser  Arg  Ser  Pro  Ser
                2085                    2090                    2095
```

Ile Thr Ser Arg Thr Ala Asp Val
2100

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CGGTTGGGCT TTCCTGTC     18

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GGGAATTCRA ADATRTTCCA NCCYTC     26

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CCCGARGAYA THGAYCYNTA YTA     23

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CGTATCGCCT CCTCCTCG     18

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GGGTCTAGAT HTTYGCNATH TTYGGNATG     29

( 2 ) INFORMATION FOR SEQ ID NO:10:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:10:

GGGGAATTCN GGRTCRAAYT GYTGCCA     27

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GGGTCTAGAR GANCARAARA ARTAYTA     27

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

TCATACTTTG GCCCAATGTC     20

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

CCCGAATTAG AGAAGGTGCT G     21

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

ACTATTGCTT GTGGTCGCCA C     21

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single ( D ) TOPOLOGY: linear ( i i ) MOLECULE TYPE: cDNA ( x i ) SEQUENCE DESCRIPTION: SEQ ID NO:15:

CATCNTTRGC NGCNTAGACN ATGAC 25

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GATTGAATGG ATCGAGCAGC C 21

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

CGTTTCTCCT TTCATATCTA G 21

( 2 ) INFORMATION FOR SEQ ID NO:18:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

GGAGBGGBGG NCKBGGNCKN GCTCA 25

( 2 ) INFORMATION FOR SEQ ID NO:19:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:19:

Gln Val Xaa Thr Phe Lys Gly Trp Xaa Xaa Ile Met
        1               5                   10

( 2 ) INFORMATION FOR SEQ ID NO:20:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:20:

Xaa Ile Xaa Thr Ser Ala Gly Trp Asp Gly Xaa Leu Xaa
1               5                       10

( 2 ) INFORMATION FOR SEQ ID NO:21:

( i ) SEQUENCE CHARACTERISTICS:
      ( A ) LENGTH: 12 amino acids
      ( B ) TYPE: amino acid
      ( C ) STRANDEDNESS: Not Relevant
      ( D ) TOPOLOGY: linear ( i i ) MOLECULE TYPE: peptide ( x i ) SEQUENCE DESCRIPTION: SEQ ID NO:21:

Thr Val Ser Thr Xaa Glu Gly Trp Pro Xaa Leu Xaa
1               5                       10

( 2 ) INFORMATION FOR SEQ ID NO:22:

( i ) SEQUENCE CHARACTERISTICS:
      ( A ) LENGTH: 13 amino acids
      ( B ) TYPE: amino acid
      ( C ) STRANDEDNESS: Not Relevant
      ( D ) TOPOLOGY: linear ( i i ) MOLECULE TYPE: peptide ( x i ) SEQUENCE DESCRIPTION: SEQ ID NO:22:

Arg Xaa Ala Thr Gly Glu Ala Trp Xaa Xaa Ile Xaa Leu
1               5                       10

( 2 ) INFORMATION FOR SEQ ID NO:23:

( i ) SEQUENCE CHARACTERISTICS:
      ( A ) LENGTH: 2100 amino acids
      ( B ) TYPE: amino acid
      ( C ) STRANDEDNESS: Not Relevant
      ( D ) TOPOLOGY: linear ( i i ) MOLECULE TYPE: protein ( x i ) SEQUENCE DESCRIPTION: SEQ ID NO:23:

Met Thr Glu Asp Ser Asp Ser Ile Ser Glu Glu Arg Ser Leu Phe
1               5                       10                      15

Arg Pro Phe Thr Arg Glu Ser Leu Val Gln Ile Glu Gln Arg Ile Ala
                20                      25                      30

Ala Glu His Glu Lys Gln Lys Glu Leu Glu Arg Lys Arg Ala Glu Gly
                35                      40                      45

Glu Val Pro Arg Tyr Gly Arg Lys Lys Gln Lys Glu Ile Arg Tyr
        50                      55                      60

Asp Asp Glu Asp Glu Asp Gly Pro Gln Pro Asp Pro Thr Leu Glu
65                      70                      75                      80

Gln Gly Val Pro Ile Pro Val Arg Leu Gln Gly Ser Phe Pro Pro Glu
                        85                      90                      95

Leu Ala Ser Thr Pro Leu Glu Asp Ile Asp Pro Tyr Tyr Ser Asn Val
                100                     105                     110

Leu Thr Phe Val Val Val Ser Lys Gly Lys Asp Ile Phe Arg Phe Ser
                115                     120                     125

Ala Ser Lys Ala Met Trp Met Leu Asp Pro Phe Asn Pro Ile Arg Arg
                130                     135                     140

Val Ala Ile Tyr Ile Leu Val His Pro Leu Phe Ser Leu Phe Ile Ile
145                     150                     155                     160

```
Thr  Thr  Ile  Leu  Val  Asn  Cys  Ile  Leu  Met  Ile  Met  Pro  Thr  Thr  Pro
               165                      170                     175

Thr  Val  Glu  Ser  Thr  Glu  Val  Ile  Phe  Thr  Gly  Ile  Tyr  Thr  Phe  Glu
               180                      185                     190

Ser  Ala  Val  Lys  Val  Met  Ala  Arg  Gly  Phe  Ile  Leu  Cys  Pro  Phe  Thr
               195                      200                     205

Tyr  Leu  Arg  Asp  Ala  Trp  Asn  Trp  Leu  Asp  Phe  Val  Val  Ile  Ala  Leu
               210                      215                     220

Ala  Tyr  Val  Thr  Met  Gly  Ile  Asp  Leu  Gly  Asn  Leu  Ala  Ala  Leu  Arg
225                           230                235                          240

Thr  Phe  Arg  Val  Leu  Arg  Ala  Leu  Lys  Thr  Val  Ala  Ile  Val  Pro  Gly
               245                      250                     255

Leu  Lys  Thr  Ile  Val  Gly  Ala  Val  Ile  Glu  Ser  Val  Lys  Asn  Leu  Arg
               260                      265                     270

Asp  Val  Ile  Ile  Leu  Thr  Met  Phe  Ser  Leu  Ser  Val  Phe  Ala  Leu  Met
               275                      280                     285

Gly  Leu  Gln  Ile  Tyr  Met  Gly  Val  Leu  Thr  Glu  Lys  Cys  Ile  Lys  Lys
     290                      295                300

Phe  Pro  Leu  Asp  Gly  Ser  Trp  Gly  Asn  Leu  Thr  Asp  Glu  Asn  Trp  Asp
305                           310                315                          320

Tyr  His  Asn  Arg  Asn  Ser  Ser  Asn  Trp  Tyr  Ser  Glu  Asp  Glu  Gly  Ile
               325                      330                     335

Ser  Phe  Pro  Leu  Cys  Gly  Asn  Ile  Ser  Gly  Ala  Gly  Gln  Cys  Asp  Asp
               340                      345                     350

Asp  Tyr  Val  Cys  Leu  Gln  Gly  Phe  Gly  Pro  Asn  Pro  Asn  Tyr  Gly  Tyr
               355                      360                     365

Thr  Ser  Phe  Asp  Ser  Phe  Gly  Trp  Ala  Phe  Leu  Ser  Ala  Phe  Arg  Leu
     370                      375                380

Met  Thr  Gln  Asp  Phe  Trp  Glu  Asp  Leu  Tyr  Gln  Leu  Val  Leu  Arg  Ala
385                      390                     395                          400

Ala  Gly  Pro  Trp  His  Met  Leu  Phe  Phe  Ile  Val  Ile  Ile  Phe  Leu  Gly
                    405                      410                     415

Ser  Phe  Tyr  Leu  Val  Asn  Leu  Ile  Leu  Ala  Ile  Val  Ala  Met  Ser  Tyr
               420                      425                     430

Asp  Glu  Leu  Gln  Arg  Lys  Ala  Glu  Glu  Glu  Ala  Ala  Glu  Glu  Glu
               435                      440                     445

Ala  Ile  Arg  Glu  Ala  Glu  Glu  Ala  Ala  Ala  Ala  Lys  Ala  Ala  Lys  Leu
     450                      455                460

Glu  Glu  Arg  Ala  Asn  Ala  Gln  Ala  Gln  Ala  Ala  Ala  Asp  Ala  Ala  Ala
465                           470                475                          480

Ala  Glu  Glu  Ala  Ala  Leu  His  Pro  Glu  Met  Ala  Lys  Ser  Pro  Thr  Tyr
                    485                      490                     495

Ser  Cys  Ile  Ser  Tyr  Glu  Leu  Phe  Val  Gly  Gly  Glu  Lys  Gly  Asn  Asp
               500                      505                     510

Asp  Asn  Asn  Lys  Glu  Lys  Met  Ser  Ile  Arg  Ser  Val  Glu  Val  Glu  Ser
               515                      520                     525

Glu  Ser  Val  Ser  Val  Ile  Gln  Arg  Gln  Pro  Ala  Pro  Thr  Thr  Ala  His
     530                      535                540

Gln  Ala  Thr  Lys  Val  Arg  Lys  Val  Ser  Thr  Thr  Ser  Leu  Ser  Leu  Pro
545                           550                555                          560

Gly  Ser  Pro  Phe  Asn  Ile  Arg  Arg  Gly  Ser  Arg  Ser  Ser  His  Lys  Tyr
                    565                      570                     575

Thr  Ile  Arg  Asn  Gly  Arg  Gly  Arg  Phe  Gly  Ile  Pro  Gly  Ser  Asp  Arg
               580                      585                     590
```

| | | | | | | | | | | | | | | |
|---|---|---|---|---|---|---|---|---|---|---|---|---|---|---|
| Lys | Pro | Leu 595 | Val | Leu | Ser | Thr | Tyr 600 | Gln | Asp | Ala | Gln 605 | Gln | His | Leu | Pro |
| Tyr | Ala 610 | Asp | Asp | Ser | Asn 615 | Ala | Val | Thr | Pro | Met 620 | Ser | Glu | Glu | Asn | Gly |
| Ala 625 | Ile | Ile | Val | Pro 630 | Val | Tyr | Tyr | Gly | Asn 635 | Leu | Gly | Ser | Arg | His | Ser 640 |
| Ser | Tyr | Thr | Ser | His 645 | Gln | Ser | Arg | Ile | Ser 650 | Tyr | Thr | Ser | His | Gly 655 | Asp |
| Leu | Leu | Gly | Gly 660 | Met | Ala | Val | Met | Gly 665 | Val | Ser | Thr | Met 670 | Thr | Lys | Glu |
| Ser | Lys | Leu 675 | Arg | Asn | Arg | Asn | Thr 680 | Arg | Asn | Gln | Ser 685 | Val | Gly | Ala | Thr |
| Asn | Gly 690 | Gly | Thr | Thr | Cys 695 | Leu | Asp | Thr | Asn | His 700 | Lys | Leu | Asp | His | Arg |
| Asp 705 | Tyr | Glu | Ile | Gly | Leu 710 | Glu | Cys | Thr | Asp 715 | Glu | Ala | Gly | Lys | Ile | Lys 720 |
| His | His | Asp | Asn | Pro 725 | Phe | Ile | Glu | Pro | Val 730 | Gln | Thr | Gln | Thr | Val 735 | Val |
| Asp | Met | Lys | Asp 740 | Val | Met | Val | Leu | Asn 745 | Asp | Ile | Ile | Glu | Gln 750 | Ala | Ala |
| Gly | Arg | His 755 | Ser | Arg | Ala | Ser | Arg 760 | Gly | Glu | Asp | Asp 765 | Glu | Asp | Glu | Asp |
| Gly | Pro 770 | Thr | Phe | Lys | Asp 775 | Lys | Ala | Leu | Glu | Val 780 | Ile | Leu | Lys | Gly | Ile |
| Asp 785 | Val | Phe | Cys | Val | Trp 790 | Asp | Cys | Cys | Trp | Val 795 | Trp | Leu | Lys | Phe | Gln 800 |
| Glu | Trp | Val | Ser | Leu 805 | Ile | Val | Phe | Asp | Pro 810 | Phe | Val | Glu | Leu | Phe 815 | Ile |
| Thr | Leu | Cys | Ile 820 | Val | Val | Asn | Thr | Met 825 | Phe | Met | Ala | Met 830 | Asp | His | His |
| Asp | Met | Asn 835 | Lys | Glu | Met | Glu | Arg 840 | Val | Leu | Lys | Ser | Gly 845 | Asn | Tyr | Phe |
| Phe | Thr 850 | Ala | Thr | Phe | Ala | Ile 855 | Glu | Ala | Thr | Met | Lys 860 | Leu | Met | Ala | Met |
| Ser 865 | Pro | Lys | Tyr | Tyr | Phe 870 | Gln | Glu | Gly | Trp | Asn 875 | Ile | Phe | Asp | Phe | Ile 880 |
| Ile | Val | Ala | Leu | Ser 885 | Leu | Leu | Glu | Leu | Gly 890 | Leu | Glu | Gly | Val | Gln 895 | Gly |
| Leu | Ser | Val | Leu 900 | Arg | Ser | Phe | Arg | Leu 905 | Leu | Arg | Val | Phe | Lys 910 | Leu | Ala |
| Lys | Ser | Trp 915 | Pro | Thr | Leu | Asn | Leu 920 | Leu | Ile | Ser | Ile | Met 925 | Gly | Arg | Thr |
| Met | Gly 930 | Ala | Leu | Gly | Asn | Leu 935 | Thr | Phe | Val | Leu | Cys 940 | Ile | Ile | Ile | Phe |
| Ile 945 | Phe | Ala | Val | Met | Gly 950 | Met | Gln | Leu | Phe | Gly 955 | Lys | Asn | Tyr | His | Asp 960 |
| His | Lys | Asp | Arg | Phe 965 | Pro | Asp | Gly | Asp | Leu 970 | Pro | Arg | Trp | Asn | Phe 975 | Thr |
| Asp | Phe | Met | His 980 | Ser | Phe | Met | Ile | Val 985 | Phe | Arg | Val | Leu 990 | Cys | Gly | Glu |
| Trp | Ile | Glu 995 | Ser | Met | Trp | Asp | Cys 1000 | Met | Tyr | Val | Gly | Asp 1005 | Val | Ser | Cys |
| Ile | Pro | Phe | Phe | Leu | Ala | Thr | Val | Val | Ile | Gly | Asn | Leu | Val | Val | Leu |

|   |   |   |   |   | 1010 |   |   |   |   | 1015 |   |   |   |   | 1020 |
|---|---|---|---|---|------|---|---|---|---|------|---|---|---|---|------|

Asn Leu Phe Leu Ala Leu Leu Leu Ser Asn Phe Gly Ser Ser Ser Leu
1025            1030             1035            1040

Ser Ala Pro Thr Ala Asp Asn Asp Thr Asn Lys Ile Ala Glu Ala Phe
                1045             1050            1055

Asn Arg Ile Gly Arg Phe Lys Ser Trp Val Lys Arg Asn Ile Ala Asp
                1060             1065            1070

Cys Phe Lys Leu Ile Arg Asn Lys Leu Thr Asn Gln Ile Ser Asp Gln
                1075             1080            1085

Pro Ser Glu His Gly Asp Asn Glu Leu Glu Leu Gly His Asp Glu Ile
                1090             1095            1100

Leu Ala Asp Gly Leu Ile Lys Lys Gly Ile Lys Glu Gln Thr Gln Leu
1105            1110             1115            1120

Glu Val Ala Ile Gly Asp Gly Met Glu Phe Thr Ile His Gly Asp Met
                1125             1130            1135

Lys Asn Asn Lys Pro Lys Lys Ser Lys Tyr Leu Asn Asn Ala Thr Asp
                1140             1145            1150

Asp Asp Thr Ala Ser Ile Asn Ser Tyr Gly Ser His Lys Asn Arg Pro
                1155             1160            1165

Phe Lys Asp Glu Ser His Lys Gly Ser Ala Glu Thr Met Glu Gly Glu
                1170             1175            1180

Glu Lys Arg Asp Ala Ser Lys Glu Asp Leu Gly Leu Asp Glu Glu Leu
1185            1190             1195            1200

Asp Glu Glu Gly Glu Cys Glu Glu Gly Pro Leu Asp Gly Asp Ile Ile
                1205             1210            1215

Ile His Ala His Asp Glu Asp Ile Leu Asp Glu Tyr Pro Ala Asp Cys
                1220             1225            1230

Cys Pro Asp Ser Tyr Tyr Lys Lys Phe Pro Ile Leu Ala Gly Asp Asp
                1235             1240            1245

Asp Ser Pro Phe Trp Gln Gly Trp Gly Asn Leu Arg Leu Lys Thr Phe
1250            1255             1260

Arg Leu Ile Glu Asp Lys Tyr Phe Glu Thr Ala Val Ile Thr Met Ile
1265            1270             1275            1280

Leu Met Ser Ser Leu Ala Leu Ala Leu Glu Asp Val His Leu Pro Gln
                1285             1290            1295

Arg Pro Ile Leu Gln Asp Ile Leu Tyr Tyr Met Asp Arg Ile Phe Thr
                1300             1305            1310

Val Ile Phe Phe Leu Glu Met Leu Ile Lys Trp Leu Ala Leu Gly Phe
                1315             1320            1325

Lys Val Tyr Leu Thr Asn Ala Trp Cys Trp Leu Asp Phe Val Ile Val
1330            1335             1340

Met Val Ser Leu Ile Asn Phe Val Ala Ser Leu Val Gly Ala Gly Gly
1345            1350             1355            1360

Ile Gln Ala Phe Lys Thr Met Arg Thr Leu Arg Ala Leu Arg Pro Leu
                1365             1370            1375

Arg Ala Met Ser Arg Met Gln Gly Met Arg Val Val Val Asn Ala Leu
                1380             1385            1390

Val Gln Ala Ile Pro Ser Ile Phe Asn Val Leu Leu Val Cys Leu Ile
                1395             1400            1405

Phe Trp Leu Ile Phe Ala Ile Met Gly Val Gln Leu Phe Ala Gly Lys
                1410             1415            1420

Tyr Phe Lys Cys Glu Asp Met Asn Gly Thr Lys Leu Ser His Glu Ile
1425            1430             1435            1440

-continued

```
Ile Pro Asn Arg Asn Ala Cys Glu Ser Glu Asn Tyr Thr Trp Val Asn
            1445                1450                      1455

Ser Ala Met Asn Phe Asp His Val Gly Asn Ala Tyr Leu Cys Leu Phe
            1460                1465                1470

Gln Val Ala Thr Phe Lys Gly Trp Ile Gln Ile Met Asn Asp Ala Ile
        1475                1480                1485

Asp Ser Arg Glu Val Asp Lys Gln Pro Ile Arg Glu Thr Asn Ile Tyr
        1490                1495                1500

Met Tyr Leu Tyr Phe Val Phe Phe Ile Ile Phe Gly Ser Phe Phe Thr
1505                1510                1515                1520

Leu Asn Leu Phe Ile Gly Val Ile Ile Asp Asn Phe Asn Glu Gln Lys
                1525                1530                1535

Lys Lys Ala Gly Gly Ser Leu Glu Met Phe Met Thr Glu Asp Gln Lys
            1540                1545                1550

Lys Tyr Tyr Ser Ala Met Lys Lys Met Gly Ser Lys Lys Pro Leu Lys
        1555                1560                1565

Ala Ile Pro Arg Pro Arg Trp Arg Pro Gln Ala Ile Val Phe Glu Ile
1570                1575                1580

Val Thr Asp Lys Lys Phe Asp Ile Ile Ile Met Leu Phe Ile Gly Leu
1585                1590                1595                1600

Asn Met Phe Thr Met Thr Leu Asp Arg Tyr Asp Ala Ser Asp Thr Tyr
                1605                1610                1615

Asn Ala Val Leu Asp Tyr Leu Asn Ala Ile Phe Val Val Ile Phe Ser
            1620                1625                1630

Ser Glu Cys Leu Leu Lys Ile Phe Ala Leu Arg Tyr His Tyr Phe Ile
            1635                1640                1645

Glu Pro Trp Asn Leu Phe Asp Val Val Val Ile Leu Ser Ile Leu
        1650                1655                1660

Gly Leu Val Leu Ser Asp Ile Ile Glu Lys Tyr Phe Val Ser Pro Thr
1665                1670                1675                1680

Leu Leu Arg Val Val Arg Val Ala Lys Val Gly Arg Val Leu Arg Leu
                1685                1690                1695

Val Lys Gly Ala Lys Gly Ile Arg Thr Leu Leu Phe Ala Leu Ala Met
            1700                1705                1710

Ser Leu Pro Ala Leu Phe Asn Ile Cys Leu Leu Leu Phe Leu Val Met
        1715                1720                1725

Phe Ile Phe Ala Ile Phe Gly Met Ser Phe Phe Met His Val Lys Glu
1730                1735                1740

Lys Ser Gly Ile Asn Asp Val Tyr Asn Phe Lys Thr Phe Gly Gln Ser
1745                1750                1755                1760

Met Ile Leu Leu Phe Gln Met Ser Thr Ser Ala Gly Trp Asp Gly Val
                1765                1770                1775

Leu Asp Ala Ile Ile Asn Glu Glu Ala Cys Asp Pro Pro Asp Asn Asp
            1780                1785                1790

Lys Gly Tyr Pro Gly Asn Cys Gly Ser Ala Thr Val Gly Ile Thr Phe
        1795                1800                1805

Leu Leu Ser Tyr Leu Val Ile Ser Phe Leu Ile Val Ile Asn Met Tyr
        1810                1815                1820

Ile Ala Val Ile Leu Glu Asn Tyr Ser Gln Ala Thr Glu Asp Val Gln
1825                1830                1835                1840

Glu Gly Leu Thr Asp Asp Asp Tyr Asp Met Tyr Tyr Glu Ile Trp Gln
                1845                1850                1855

Gln Phe Asp Pro Glu Gly Thr Gln Tyr Ile Arg Tyr Asp Gln Leu Ser
            1860                1865                1870
```

| | | | | | | | | | | | | | | |
|---|---|---|---|---|---|---|---|---|---|---|---|---|---|---|
|Glu|Phe|Leu|Asp|Val|Leu|Glu|Pro|Pro|Leu|Gln|Ile|His|Lys|Pro|Asn|
| | |1875| | | |1880| | | |1885| | | | |
|Lys|Tyr|Lys|Ile|Ile|Ser|Met|Asp|Ile|Pro|Ile|Cys|Arg|Gly|Asp|Leu|
| |1890| | | | |1895| | | |1900| | | | |
|Met|Tyr|Cys|Val|Asp|Ile|Leu|Asp|Ala|Leu|Thr|Lys|Asp|Phe|Phe|Ala|
|1905| | | | |1910| | | |1915| | | | |1920|
|Arg|Lys|Gly|Asn|Pro|Ile|Glu|Glu|Thr|Gly|Glu|Ile|Gly|Glu|Ile|Ala|
| | | |1925| | | |1930| | | |1935| | | |
|Ala|Arg|Pro|Asp|Thr|Glu|Gly|Tyr|Glu|Pro|Val|Ser|Ser|Thr|Leu|Trp|
| | | |1940| | | |1945| | | |1950| | | |
|Arg|Gln|Arg|Glu|Glu|Tyr|Cys|Ala|Arg|Leu|Ile|Gln|His|Ala|Trp|Arg|
| | |1955| | | |1960| | | |1965| | | | |
|Lys|His|Lys|Ala|Arg|Gly|Glu|Gly|Gly|Ser|Phe|Glu|Pro|Asp|Thr|
| | |1970| | | |1975| | | |1980| | | | |
|Asp|His|Gly|Asp|Gly|Gly|Asp|Pro|Asp|Ala|Gly|Asp|Pro|Ala|Pro|Asp|
|1985| | | | |1990| | | |1995| | | | |2000|
|Glu|Ala|Thr|Asp|Gly|Asp|Ala|Pro|Ala|Gly|Gly|Asp|Gly|Ser|Val|Asn|
| | | |2005| | | |2010| | | |2015| | | |
|Gly|Thr|Ala|Glu|Gly|Ala|Ala|Asp|Ala|Asp|Glu|Ser|Asn|Val|Asn|Ser|
| | | |2020| | | |2025| | | |2030| | | |
|Pro|Gly|Glu|Asp|Ala|Ala|Ala|Ala|Ala|Ala|Ala|Ala|Ala|Ala|Ala|
| | | |2035| | | |2040| | | |2045| | | |
|Ala|Ala|Gly|Thr|Thr|Thr|Ala|Gly|Ser|Pro|Gly|Ala|Gly|Ser|Ala|Gly|
| | |2050| | | |2055| | | |2060| | | | |
|Arg|Gln|Thr|Ala|Val|Leu|Val|Glu|Ser|Asp|Gly|Phe|Val|Thr|Lys|Asn|
|2065| | | |2070| | | |2075| | | | |2080|
|Gly|His|Lys|Val|Val|Ile|His|Ser|Arg|Ser|Pro|Ser|Ile|Thr|Ser|Arg|
| | | |2085| | | |2090| | | |2095| | | |
|Thr|Ala|Asp|Val| | | | | | | | | | | |
| | | |2100| | | | | | | | | | | |

( 2 ) INFORMATION FOR SEQ ID NO:24:

( i ) SEQUENCE CHARACTERISTICS:
        ( A ) LENGTH: 6519 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

```
ATGACAGAAG ATTCCGACTC GATATCTGAG GAAGAACGCA GTTTGTTCCG TCCCTTTACC        60

CGCGAATCAT TGGTGCAAAT CGAACAACGC ATTGCCGCTG AACATGAAAA GCAGAAGGAG       120

CTGGAAAGAA AGAGAGCCGA GGGAGAGGTG CCGCGATATG GTCGCAAGAA AAAACAAAAA       180

GAAATCCGAT ATGATGACGA GGACGAGGAT GAAGGTCCAC AACCGGATCC TACACTTGAA       240

CAGGGTGTGC CAATACCTGT TCGATTGCAG GGCAGCTTCC CGCCGGAATT GGCCTCCACT       300

CCTCTCGAGG ATATCGATCC CTACTACAGC AATGTACTGA CATTCGTAGT TGTAAGCAAA       360

GGAAAAGATA TTTTTCGCTT TTCTGCATCA AAAGCAATGT GGATGCTCGA TCCATTCAAT       420

CCGATACGTC GTGTGGCCAT TTACATTCTA GTGCATCCAT TATTTTCCCT ATTCATCATC       480

ACCACAATTC TCGTCAACTG CATCCTGATG ATAATGCCGA CAACGCCCAC GGTTGAGTCC       540

ACTGAGGTGA TATTCACCGG AATCTACACA TTTGAATCAG CTGTTAAAGT GATGGCACGA       600

GGTTTCATTT TATGCCCGTT TACGTATCTT AGAGATGCAT GGAATTGGCT GGACTTCGTA       660
```

```
GTAATAGCTT TAGCTTATGT GACCATGGGT ATAGATTTAG GTAATCTAGC AGCCCTGCGA    720
ACGTTTAGGG TGCTGCGAGC GCTTAAAACC GTAGCCATTG TGCCAGGCTT GAAGACCATC    780
GTCGGCGCCG TCATCGAATC GGTGAAGAAT CTGCGCGATG TGATTATCCT GACCATGTTC    840
TCCCTGTCGG TGTTCGCGTT GATGGGCCTA CAGATCTATA TGGGCGTGCT CACCGAGAAG    900
TGCATCAAGA AGTTCCCGCT GGACGGTTCC TGGGGCAATC TGACCGACGA GAACTGGGAC    960
TATCACAATC GCAATAGCTC CAATTGGTAT TCCGAGGACG AGGGCATCTC ATTTCCGTTA   1020
TGCGGCAATA TATCCGGTGC GGGGCAATGC GACGACGATT ACGTGTGCCT GCAGGGGTTT   1080
GGTCCGAATC CGAATTATGG CTACACCAGC TTCGATTCGT TCGGATGGGC TTTCCTGTCC   1140
GCCTTCCGGC TGATGACACA GGACTTCTGG GAGGATCTGT ACCAGCTGGT GTTGCGCGCC   1200
GCCGGACCAT GGCACATGCT GTTCTTTATA GTCATCATCT TCCTAGGTTC ATTCTATCTT   1260
GTGAATTTGA TTTTGGCCAT TGTTGCCATG TCGTATGACG AATTGCAAAG GAAGGCCGAA   1320
GAAGAAGAGG CTGCCGAAGA GGAGGCGATA CGTGAAGCGG AAGAAGCTGC CGCCGCCAAA   1380
GCGGCCAAGC TGGAGGAGCG GGCCAATGCG CAGGCTCAGG CAGCAGCGGA TGCGGCTGCC   1440
GCCGAAGAGG CTGCACTGCA TCCGGAAATG GCCAAGAGTC CGACGTATTC TTGCATCAGC   1500
TATGAGCTAT TTGTTGGCGG CGAGAAGGGC AACGATGACA ACAACAAAGA GAAGATGTCC   1560
ATTCGGAGCG TCGAGGTGGA GTCGGAGTCG GTGAGCGTTA TACAAAGACA ACCAGCACCT   1620
ACCACAGCAC ACCAAGCTAC CAAAGTTCGT AAAGTGAGCA CGACATCCTT ATCCTTACCT   1680
GGTTCACCGT TTAACATACG CAGGGGATCA CGTAGTTCTC ACAAGTACAC GATACGGAAC   1740
GGACGTGGCC GCTTTGGTAT ACCCGGTAGC GATCGTAAGC CATTGGTATT GTAACATAT    1800
CAGGATGCCC AGCAGCACTT GCCCTATGCC GACGACTCGA ATGCCGTCAC CCCGATGTCC   1860
GAAGAGAATG GGGCCATCAT AGTGCCCGTG TACTATGGCA ATCTAGGCTC CCGACACTCA   1920
TCGTATACCT CGCATCAGTC CCGAATATCG TATACCTCAC ATGGCGATCT ACTCGGCGGC   1980
ATGGCCGTCA TGGGCGTCAG CACAATGACC AAGGAGAGCA AATTGCGCAA CCGCAACACA   2040
CGCAATCAAT CAGTGGGCGC CACCAATGGC GGCACCACCT GTCTGGACAC CAATCACAAG   2100
CTCGATCATC GCGACTACGA AATTGGCCTG GAGTGCACGG ACGAAGCTGG CAAGATTAAA   2160
CATCATGACA ATCCTTTTAT CGAGCCCGTC CAGACACAAA CGGTGGTTGA TATGAAAGAT   2220
GTGATGGTCC TGAATGACAT CATCGAACAG GCCGCTGGTC GGCACAGTCG GGCAAGCGAT   2280
CGCGGTGAGG ACGATGACGA GGATGGGCCG ACGTTCAAAG ACAAGGCACT CGAAGTGATC   2340
CTCAAAGGCA TCGATGTGTT TTGTGTGTGG GACTGTTGCT GGGTTTGGTT GAAATTTCAG   2400
GAGTGGGTAT CGCTCATCGT CTTCGATCCC TTCGTCGAGC TCTTCATCAC GCTGTGCATT   2460
GTGGTCAACA CGATGTTCAT GGCAATGGAT CACCACGATA TGAACAAGGA GATGGAACGC   2520
GTGCTCAAGA GTGGCAACTA TTTCTTCACC GCCACCTTTG CCATCGAGGC CACCATGAAG   2580
CTAATGGCCA TGAGCCCCAA GTACTATTTC CAGGAGGGCT GGAACATCTT CGACTTCATT   2640
ATCGTGGCCC TATCGCTATT GGAACTGGGA CTCGAGGGTG TCCAGGGTCT GTCCGTATTG   2700
CGTTCCTTTC GATTGCTGCG TGTATTCAAA CTGGCCAAGT CTTGGCCCAC ACTTAATTTA   2760
CTCATTTCGA TTATGGGACG CACCATGGGC GCTTTGGGTA ATCTGACATT TGTACTTTGC   2820
ATTATCATCT TCATCTTTGC GGTGATGGGA ATGCAACTGT TCGGAAAGAA TTATCATGAT   2880
CACAAGGACC GCTTTCCGGA TGGCGACCTG CCGCGCTGGA ACTTCACCGA CTTTATGCAC   2940
AGCTTCATGA TCGTGTTCCG GGTGCTCTGC GGAGAATGGA TCGAGTCCAT GTGGGACTGC   3000
ATGTACGTGG GCGATGTCTC GTGCATTCCC TTCTTCTTGG CCACCGTTGT CATCGGCAAT   3060
```

```
CTTGTGGTAC TTAACCTTTT CTTAGCCTTG CTTTTGTCCA ATTTTGGCTC ATCTAGCTTA   3120
TCAGCGCCGA CTGCCGATAA CGATACGAAT AAAATAGCCG AGGCCTTCAA TCGAATTGGC   3180
CGATTTAAAA GTTGGGTTAA GCGTAATATT GCTGATTGTT TCAAGTTAAT ACGTAACAAA   3240
TTGACAAATC AAATAAGTGA TCAACCATCA GAGCATGGTG ACAACGAACT GGAGCTGGGC   3300
CACGACGAGA TCCTCGCCGA CGGCCTCATC AAGAAGGGGA TCAAGGAGCA GACGCAACTG   3360
GAGGTGGCCA TCGGGGATGG CATGGAATTC ACGATACACG GCGACATGAA GAACAACAAG   3420
CCGAAGAAAT CCAAATATCT AAATAACGCA ACGGACGACG ACACTGCCAG CATTAACTCA   3480
TATGGTAGCC ATAAGAATCG ACCATTCAAG GACGAGAGCC ACAAGGGCAG CGCCGAGACG   3540
ATGGAGGGCG AGGAGAAGCG CGACGCCAGC AAGGAGGATT TAGGTCTCGA CGAGGAACTG   3600
GACGAGGAGG GCGAATGCGA GGAGGGCCCG CTCGACGGTG ATATCATTAT TCATGCACAC   3660
GACGAGGATA TACTCGATGA ATATCCAGCT GATTGCTGCC CCGATTCGTA CTATAAGAAA   3720
TTTCCGATCT TAGCCGGTGA CGATGACTCG CCGTTCTGGC AAGGATGGGG CAATTTACGA   3780
CTGAAAACTT TTCGATTAAT TGAGGATAAA TATTTTGAAA CAGCTGTTAT CACTATGATT   3840
TTAATGAGTA GCTTAGCTTT GGCATTAGAA GATGTACATC TGCCACAAAG ACCCATACTG   3900
CAGGATATTT TATACTATAT GGACAGAATA TTTACGGTTA TATTCTTCTT GGAAATGTTA   3960
ATCAAGTGGT TGGCGCTCGG CTTCAAAGTG TACTTGACCA ACGCGTGGTG TTGGCTCGAT   4020
TTCGTGATTG TCATGGTATC GCTTATCAAC TTCGTTGCTT CACTTGTTGG AGCTGGTGGT   4080
ATTCAAGCCT TCAAGACTAT GCGAACGTTA AGAGCACTGA GACCACTACG TGCCATGTCC   4140
CGTATGCAGG GCATGAGGGT CGTCGTTAAT GCGCTGGTAC AAGCTATACC GTCCATCTTC   4200
AATGTGCTAT TGGTGTGTCT AATATTTTGG CTAATTTTTG CCATAATGGG TGTACAGCTT   4260
TTTGCTGGAA AATATTTTAA GTGCGAGGAC ATGAATGGCA CGAAGCTCAG CCACGAGATC   4320
ATACCAAATC GCAATGCCTG CGAGAGCGAG AACTACACGT GGGTGAATTC AGCAATGAAT   4380
TTCGATCATG TAGGTAACGC GTATCTGTGC CTTTTCCAAG TGGCCACCTT CAAAGGCTGG   4440
ATACAAATCA TGAACGATGC TATCGATTCA CGAGAGGTGG ACAAGCAACC AATTCGTGAA   4500
ACGAACATCT ACATGTATTT ATATTTCGTA TTCTTCATCA TATTTGGATC ATTTTTCACA   4560
CTCAATCTGT TCATTGGTGT TATCATTGAT AATTTTAATG AGCAAAAGAA AAAAGCAGGT   4620
GGATCATTAG AAATGTTCAT GACAGAAGAT CAGAAAAAGT ACTATAGTGC TATGAAAAAG   4680
ATGGGCTCTA AAAAACCATT AAAAGCCATT CCAAGACCAA GGTGGCGACC ACAAGCAATA   4740
GTCTTTGAAA TAGTAACCGA TAAGAAATTC GATATAATCA TTATGTTATT CATTGGTCTG   4800
AACATGTTCA CCATGACCCT CGATCGTTAC GATGCGTCGG ACACGTATAA CGCGGTCCTA   4860
GACTATCTCA ATGCGATATT CGTAGTTATT TTCAGTTCCG AATGTCTATT AAAAATATTC   4920
GCTTTACGAT ATCACTATTT TATTGAGCCA TGGAATTTAT TTGATGTAGT AGTTGTCATT   4980
TTATCCATCT TAGGTCTTGT ACTTAGCGAT ATTATCGAGA AGTACTTCGT GTCGCCGACC   5040
CTGCTCCGAG TGGTGCGTGT GGCGAAAGTG GGCCGTGTCC TTCGACTGGT GAAGGGAGCC   5100
AAGGGCATTC GGACACTGCT CTTCGCGTTG GCCATGTCGC TGCCGGCCCT GTTCAACATC   5160
TGCCTGCTGC TGTTCCTGGT CATGTTCATC TTTGCCATTT TCGGCATGTC GTTCTTCATG   5220
CACGTGAAGG AGAAGAGCGG CATTAACGAC GTCTACAACT TCAAGACCTT TGGCCAGAGC   5280
ATGATCCTGC TCTTTCAGAT GTCGACGTCA GCCGGTTGGG ATGGTGTACT GGACGCCATT   5340
ATCAATGAGG AAGCATGCGA TCCACCCGAC AACGACAAAG GCTATCCGGG CAATTGTGGT   5400
TCAGCGACCG TTGGAATAAC GTTTCTCCTC TCATACCTAG TTATAAGCTT TTTGATAGTT   5460
```

```
ATTAATATGT  ACATTGCTGT  CATTCTCGAG  AACTATAGTC  AGGCCACCGA  GGACGTGCAA    5520
GAGGGTCTAA  CCGACGACGA  CTACGACATG  TACTATGAGA  TCTGGCAGCA  ATTCGATCCG    5580
GAGGGCACCC  AGTACATACG  CTATGATCAG  CTGTCCGAAT  TCCTGGACGT  ACTGGAGCCC    5640
CCGCTGCAGA  TCCACAAACC  GAACAAGTAC  AAGATCATAT  CGATGGACAT  ACCCATCTGT    5700
CGCGGTGACC  TCATGTACTG  CGTCGACATC  CTCGACGCCC  TTACGAAAGA  CTTCTTTGCG    5760
CGGAAGGGCA  ATCCGATAGA  GGAGACGGGT  GAGATTGGTG  AGATAGCGGC  CCGCCCGGAT    5820
ACGGAGGGCT  ACGAGCCCGT  CTCATCAACG  CTGTGGCGTC  AGCGTGAGGA  GTACTGCGCC    5880
CGGCTAATCC  AGCACGCCTG  GCGAAAGCAC  AAGGCGCGCG  GCGAGGGAGG  TGGGTCCTTT    5940
GAGCCGGATA  CGGATCATGG  CGATGGCGGT  GATCCGGATG  CCGGGGACCC  GGCGCCCGAT    6000
GAAGCAACGG  ACGGCGATGC  GCCCGCTGGT  GGAGATGGTA  GTGTTAACGG  TACTGCAGAA    6060
GGAGCTGCCG  ATGCCGATGA  GAGTAATGTA  AATAGTCCGG  GTGAGGATGC  AGCGGCGGCG    6120
GCAGCAGCAG  CAGCAGCAGC  GGCGGCGGCG  GGCACGACGA  CGGCGGGAAG  TCCCGGAGCG    6180
GGTAGCGCCG  GGCGACAGAC  CGCCGTTCTC  GTGGAGAGCG  ACGGGTTCGT  GACGAAGAAC    6240
GGCCACAAGG  TGGTCATCCA  CTCGCGATCG  CCGAGCATCA  CGTCGCGCAC  GGCGGATGTC    6300
TGAGCCAGGC  CTCGCCCCCC  CCTCCAAGAT  GCACGCGAGT  ATTAGCATGA  GTACGTGTTG    6360
GATGTTGCAT  GTTGCATCAG  CGATGCAGCA  GCGACAGTGA  GCTAACAACA  ACAGCAACAA    6420
GGCGAACAAC  AAGCATAATT  TTCTGCTATA  TAATGAAAGA  ACACCATACA  AACAAGCAAA    6480
CAACAACACA  AAAAAAACAA  CAAACAAACA  AGAATAAAC                             6519
```

( 2 ) INFORMATION FOR SEQ ID NO:25:

( i ) SEQUENCE CHARACTERISTICS:
        ( A ) LENGTH: 413 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:25:

```
Gln  Leu  Phe  Ala  Gly  Lys  Tyr  Phe  Lys  Cys  Val  Asp  Leu  Asn  His  Thr
 1              5                        10                       15

Thr  Leu  Ser  His  Glu  Ile  Ile  Pro  Asp  Arg  Asn  Ala  Cys  Ile  Leu  Glu
              20                        25                       30

Asn  Tyr  Thr  Trp  Glu  Asn  Ser  Pro  Met  Asn  Phe  Asp  His  Val  Gly  Lys
         35                        40                       45

Ala  Tyr  Leu  Cys  Leu  Phe  Gln  Val  Ala  Thr  Phe  Lys  Gly  Trp  Ile  Gln
    50                        55                       60

Ile  Met  Asn  Asp  Ala  Ile  Asp  Ser  Arg  Glu  Val  Gly  Arg  Gln  Pro  Ile
65                       70                       75                       80

Arg  Glu  Thr  Asn  Ile  Tyr  Met  Tyr  Leu  Tyr  Phe  Val  Phe  Phe  Ile  Ile
                        85                       90                       95

Phe  Gly  Ser  Phe  Phe  Thr  Leu  Asn  Leu  Phe  Ile  Gly  Val  Ile  Ile  Asp
                   100                      105                     110

Asn  Phe  Asn  Glu  Gln  Lys  Lys  Lys  Ala  Gly  Gly  Ser  Leu  Glu  Met  Phe
              115                      120                     125

Met  Thr  Glu  Asp  Gln  Lys  Lys  Tyr  Tyr  Asn  Ala  Met  Lys  Lys  Met  Gly
         130                     135                     140

Ser  Lys  Lys  Pro  Leu  Lys  Ala  Ile  Pro  Arg  Pro  Lys  Trp  Arg  Pro  Gln
145                      150                     155                     160
```

|     |     |     |     |     |     |     |     |     |     |     |     |     |     |     |
| --- | --- | --- | --- | --- | --- | --- | --- | --- | --- | --- | --- | --- | --- | --- |
| Ala | Ile | Val | Phe | Glu<br>165 | Ile | Val | Thr | Asp | Lys<br>170 | Lys | Phe | Asp | Met | Ile<br>175 | Ile |
| Met | Leu | Phe | Ile<br>180 | Gly | Leu | Asn | Met | Leu<br>185 | Thr | Met | Thr | Leu | Asp<br>190 | His | Tyr |
| Gln | Gln | Ser<br>195 | Glu | Thr | Phe | Ser | Thr<br>200 | Val | Leu | Asp | Tyr | Leu<br>205 | Asn | Met | Ile |
| Phe | Ile<br>210 | Val | Ile | Phe | Ser | Ser<br>215 | Glu | Cys | Leu | Leu | Lys<br>220 | Met | Phe | Ala | Leu |
| Arg<br>225 | Tyr | His | Tyr | Phe | Val<br>230 | Glu | Pro | Trp | Asn | Leu<br>235 | Phe | Asp | Phe | Val | Val<br>240 |
| Val | Asn | Phe | Ser | Ile<br>245 | Leu | Ser | Leu | Val | Leu<br>250 | Ser | Asp | Ile | Ile | Glu<br>255 | Lys |
| Tyr | Phe | Val | Ser<br>260 | Pro | Thr | Leu | Leu | Arg<br>265 | Val | Val | Arg | Val<br>270 | Ala | Lys | Val |
| Gly | Arg | Val<br>275 | Leu | Arg | Leu | Val | Lys<br>280 | Gly | Ala | Lys | Gly | Ile<br>285 | Arg | Thr | Leu |
| Leu | Phe<br>290 | Gly | Leu | Ala | Met | Ser<br>295 | Leu | Pro | Ala | Leu | Phe<br>300 | Asn | Ile | Cys | Leu |
| Leu<br>305 | Leu | Phe | Leu | Val | Met<br>310 | Phe | Ile | Phe | Ala | Ile<br>315 | Phe | Gly | Met | Ser | Phe<br>320 |
| Phe | Met | His | Val | Lys<br>325 | Asp | Lys | Gly | Gly | Leu<br>330 | Asp | Asp | Val | Tyr | Asn<br>335 | Phe |
| Lys | Thr | Phe | Val<br>340 | Gln | Ser | Met | Ile | Leu<br>345 | Leu | Phe | Gln | Met | Ser<br>350 | Thr | Ser |
| Ala | Gly | Trp<br>355 | Asp | Gly | Val | Leu | Asp<br>360 | Gly | Ile | Ile | Asn | Glu<br>365 | Glu | Glu | Cys |
| Xaa | Leu<br>370 | Pro | Asp | Asn | Glu | Arg<br>375 | Gly | Tyr | Pro | Gly | Asn<br>380 | Cys | Gly | Ser | Ala |
| Thr<br>385 | Ile | Gly | Ile | Thr | Tyr<br>390 | Leu | Leu | Ser | Tyr | Leu<br>395 | Val | Ile | Ser | Phe | Leu<br>400 |
| Ile | Val | Ile | Asn | Met<br>405 | Tyr | Ile | Ala | Val | Ile<br>410 | Leu | Glu | Asn |     |     |     |

( 2 ) INFORMATION FOR SEQ ID NO:26:

( i ) SEQUENCE CHARACTERISTICS:
        ( A ) LENGTH: 1237 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

| | | | | | |
|---|---|---|---|---|---|
| ATGTCACTGC | CAGCCTTATT | CAACATCTGT | CTGCTGCTGT | TCCTTGTGAT | GTTCATCTTC | 60 |
| GCCATCTTCG | GCATGTCGTT | CTTTATGCAC | GTCAAAGACA | AAGGTGGTCT | CGACGACGTG | 120 |
| TACAACTTCA | AGACCTTCGT | GCAGAGTATG | ATCCTGCTAT | TCAGATGTC | GACGTCGCCG | 180 |
| GCTGGGACAA | CTGTTCGCTG | GCAAATATTT | CAAGTGCGTC | GACCTCAACC | ACACGACGTT | 240 |
| GAGCCACGAA | ATCATCCCAG | ACCGGAATGC | GTGCATCTTA | GAGAACTACA | CCTGGGAGAA | 300 |
| CTCACCGATG | AACTTTGACC | ATGTCGGCAA | GGCGTATCTC | TGCCTGTTCC | AAGTGGCCAC | 360 |
| CTTCAAGGGA | TGGATACAGA | TCATGAACGA | CGCTATTGAT | TCGAGAGAAG | TGGGCCGGCA | 420 |
| ACCTATACGC | GAGACGAACA | TCTACATGTA | CCTGTACTTC | GTGTTCTTCA | TCATATTTGG | 480 |
| CTCATTCTTC | ACTCTCAACC | TATTCATCGG | TGTGATCATC | GACAACTTTA | ACGAACAGAA | 540 |
| GAAGAAAGCC | GGCGGCAGCC | TTGAGATGTT | CATGACTGAG | GACCAGAAGA | AATACTACAA | 600 |

| | | | | | | |
|---|---|---|---|---|---|---|
|TGCCATGAAG|AAAATGGGTT|CTAAAAAACC|TTTAAAAGCT|ATCCCGAGAC|CGAAGTGGCG|660|
|GCCACAAGCG|ATCGTGTTCG|AGATAGTGAC|GGACAAGAAG|TTCGACATGA|TCATCATGTT|720|
|GTTCATCGGC|CTCAACATGT|TGACGATGAC|GCTCGATCAC|TACCAGCAGT|CGGAGACCTT|780|
|CAGCACTGTC|CTCGACTACC|TCAACATGAT|ATTCATCGTG|ATATTCAGTT|CAGAGTGCCT|840|
|ATTAAAAATG|TTCGCCTTAC|GCTACCATTA|CTTTGTTGAG|CCATGGAACT|TGTTCGATTT|900|
|CGTAGTAGTC|AATTTCTCAA|TTCTTAGTTT|GGTATTGAGT|GATATTATAG|AAAAATATTT|960|
|TGTGTCACCC|ACGTTACTGA|GGGTGGTGAG|AGTAGCGAAG|GTCGGTCGTG|TGTTGCGTCT|1020|
|CGTGAAGGGT|GCGAAGGGTA|TCCGGACGTT|ATTGTTCGGG|CTGGCCACGG|CGTGCTGGAC|1080|
|GGCATCATCA|ATGAGGAGGA|GTGCGACTGC|CGGACAACGA|GCGCGGCTAC|CCGGGCAACT|1140|
|GCGGCTCTGC|ACCATCGGCA|TCACCTACCT|GCTGTCCTAC|CTCGTCATCT|CCTTCCTCAT|1200|
|CGTCATCAAC|ATGTACATCG|CCGTCATTCT|CGAGAAT| | |1237|

( 2 ) INFORMATION FOR SEQ ID NO:27:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

GAGGAATTCG AGAAACGCGA CGTCAGC        27

( 2 ) INFORMATION FOR SEQ ID NO:28:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

CCCGCATGCT CAGACATCTG CCGTCCTGG        29

( 2 ) INFORMATION FOR SEQ ID NO:29:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

CCTCCCGGGA TGACAGAAGA TTCCGACTCG ATATCTGAG        39

( 2 ) INFORMATION FOR SEQ ID NO:30:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

```
TCGGCATGCC  AGTCGGCCGG  ATAGTCGTCG                                                         3 0
```

( 2 ) INFORMATION FOR SEQ ID NO:31:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

```
GTGGCCACCT  TTGAGGGCTG  GATCCAG                                                            2 7
```

( 2 ) INFORMATION FOR SEQ ID NO:32:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

```
ATGTCTACCT  CAGAGGGTTG  GGATGGTG                                                           2 8
```